US010058612B2

(12) United States Patent
Shchepinov

(10) Patent No.: US 10,058,612 B2
(45) Date of Patent: Aug. 28, 2018

(54) IMPAIRED ENERGY PROCESSING DISORDERS AND MITOCHONDRIAL DEFICIENCY

(75) Inventor: Mikhail S. Shchepinov, Kingston Upon Thames (GB)

(73) Assignee: Retrotope, Inc., Los Altos, CA (US)

( * ) Notice: Subject to any disclaimer, the term of this patent is extended or adjusted under 35 U.S.C. 154(b) by 0 days.

(21) Appl. No.: 14/113,546

(22) PCT Filed: Apr. 24, 2012

(86) PCT No.: PCT/US2012/034833
§ 371 (c)(1),
(2), (4) Date: Oct. 23, 2013

(87) PCT Pub. No.: WO2012/148927
PCT Pub. Date: Nov. 1, 2012

(65) Prior Publication Data
US 2014/0044692 A1    Feb. 13, 2014

Related U.S. Application Data

(60) Provisional application No. 61/479,288, filed on Apr. 26, 2011.

(51) Int. Cl.
| | | |
|---|---|---|
| *A61K 45/06* | (2006.01) | |
| *A61K 31/122* | (2006.01) | |
| *A61K 31/192* | (2006.01) | |
| *A61K 31/20* | (2006.01) | |
| *A61K 31/201* | (2006.01) | |
| *A61K 31/202* | (2006.01) | |
| *A61K 31/355* | (2006.01) | |
| *A61K 31/375* | (2006.01) | |

(52) U.S. Cl.
CPC ............ *A61K 45/06* (2013.01); *A61K 31/122* (2013.01); *A61K 31/192* (2013.01); *A61K 31/20* (2013.01); *A61K 31/201* (2013.01); *A61K 31/202* (2013.01); *A61K 31/355* (2013.01); *A61K 31/375* (2013.01)

(58) Field of Classification Search
USPC ....................................................... 424/94.1
See application file for complete search history.

(56) References Cited

U.S. PATENT DOCUMENTS

| | | | |
|---|---|---|---|
| 3,520,872 A | 7/1970 | Wechter et al. | |
| 5,194,448 A | 3/1993 | Coupland et al. | |
| 5,436,269 A | 7/1995 | Yazawa | |
| 5,709,888 A | 1/1998 | Gil et al. | |
| 5,843,497 A | 12/1998 | Sundram et al. | |
| 6,111,066 A | 8/2000 | Anderson et al. | |
| 6,417,233 B1 | 7/2002 | Sears et al. | |
| 6,503,478 B2 | 1/2003 | Chaiken et al. | |
| 2001/0023259 A1 | 9/2001 | Slabas et al. | |
| 2002/0198177 A1 | 12/2002 | Horrobin | |
| 2004/0043013 A1 | 3/2004 | McCleary | |
| 2005/0164908 A1 | 7/2005 | Ginsberg et al. | |
| 2006/0035382 A1 | 2/2006 | Shinozaki et al. | |
| 2006/0205685 A1 | 9/2006 | Phiasivongsa Pasit et al. | |
| 2006/0241088 A1 | 10/2006 | Arterburn et al. | |
| 2007/0032548 A1 | 2/2007 | Ellis | |
| 2008/0234197 A1 | 9/2008 | Allam et al. | |
| 2009/0054504 A1 | 2/2009 | Bozik et al. | |
| 2009/0069354 A1 | 3/2009 | Czarnik | |
| 2009/0182022 A1 | 7/2009 | Rongen et al. | |
| 2009/0232916 A1 | 9/2009 | Shulman et al. | |
| 2009/0306015 A1 | 12/2009 | Gately et al. | |
| 2009/0326070 A1 | 12/2009 | Freeman et al. | |
| 2010/0022645 A1 | 1/2010 | Nelson | |
| 2010/0160248 A1 | 6/2010 | Shchepinov | |
| 2011/0028434 A1 | 2/2011 | Destaillats et al. | |
| 2011/0028493 A1 | 2/2011 | Matsunaga et al. | |
| 2011/0082206 A1 | 4/2011 | Miller | |
| 2011/0190195 A1 | 8/2011 | Atlas | |

FOREIGN PATENT DOCUMENTS

| | | |
|---|---|---|
| CN | 1114878 A | 1/1996 |
| EP | 0713653 A1 | 5/1996 |
| EP | 1548116 | 6/2005 |
| EP | 1834639 A1 | 9/2007 |
| EP | 1 961 311 A1 | 8/2008 |
| EP | 2641891 A1 | 9/2013 |
| FR | 2721518 | 12/1995 |
| JP | 2-237919 | 9/1990 |
| JP | H8-268885 | 10/1996 |
| JP | H9-143492 | 6/1997 |

(Continued)

OTHER PUBLICATIONS

Clarke et al. Isotope-reinforced polyunsaturated fatty acids protect yeast cells from oxidative stress. FASEB J. 2010;24:849.2.*
Wendt et al. Mass spectrometry of perdeuterated molecules of biological origin. fatty acid esters from scenedesmus obliquus. Biochemistry. 1970;9(25):4854-4866.*
Shchepinov et al. Mitigating effects of oxidation in aging and diseases. Retrotope. 2010;1-11.*
Yashodhara et al. Omega-3 fatty acids: a comprehensive review of their role in health and disease. Postgrad Med J. 2009;85:84-90.*
Reddy P.H. Mitochondrial medicine for aging and neurodegenerative diseases. Neuromolecular Med. 2008;10(4):291-315.*
Triglycerides. Medium chain triglycerides. Alternative Medicine Review. 2002;7(5):418-420.*
Adhikary et al., UVA-visible photo-excitation of guanine radical cations produces sugar radicals in DNA and model structures, Nucleic Acids Research, vol. 33, No. 17, pp. 5553-5564.
Asada et al; Stereochemistry of meso-α,ε Diaminopimelate Decarboxylase Reaction: The First Evidence for Pyriodoxal 5'-Phosphate Dependant Decarboxylation with Inversion of Configuration, Biochemistry, 1981, vol. 20, No. 24, pp. 6881-6886.

(Continued)

*Primary Examiner* — Lynn Y Fan
(74) *Attorney, Agent, or Firm* — Knobbe Martens Olson & Bear LLP

(57) ABSTRACT

Some aspects of the invention provide for a method of treating Impaired Energy Processing Disorders and Mitochondrial Deficiencies using polyunsaturated fatty acids which are modified in certain positions to attenuate oxidative damage by Reactive Oxygen Species (ROS) and/or suppress the rate of formation of reactive products and toxic compounds.

22 Claims, 25 Drawing Sheets

(56) References Cited

FOREIGN PATENT DOCUMENTS

| JP | 2010-291955 | 11/1998 |
|---|---|---|
| JP | 2000-290291 | 10/2000 |
| JP | 2001-145880 | 5/2001 |
| JP | 2001-514239 | 9/2001 |
| JP | 2001-270832 | 10/2001 |
| JP | 2001-519355 | 10/2001 |
| JP | 2002-513911 | 5/2002 |
| JP | 2002-527387 | 8/2002 |
| JP | 2002-536981 | 11/2002 |
| JP | 2004-81156 | 3/2004 |
| JP | 2004-520848 | 7/2004 |
| JP | 2004-530635 | 10/2004 |
| JP | 2005-510501 | 4/2005 |
| JP | 2006-502081 | 1/2006 |
| JP | 2006-504701 | 2/2006 |
| JP | 2006-510669 | 3/2006 |
| JP | 2008-504372 | 2/2008 |
| JP | 2009-007337 | 1/2009 |
| JP | 2009-502745 | 1/2009 |
| JP | 2009-525948 | 7/2009 |
| JP | 2010-521493 | 6/2010 |
| JP | 2013-509439 | 3/2013 |
| KR | 10-2005-0029582 | 3/2005 |
| WO | WO 9956790 | 11/1999 |
| WO | WO00/21524 | 4/2000 |
| WO | WO01/17374 A1 | 3/2001 |
| WO | WO02/096221 | 5/2002 |
| WO | WO03/035095 | 5/2003 |
| WO | WO 2003/051348 | 6/2003 |
| WO | WO03/064576 A2 | 8/2003 |
| WO | WO 2004/028536 | 4/2004 |
| WO | WO 2004/029254 | 4/2004 |
| WO | WO 2004/052227 | 6/2004 |
| WO | WO2005/037848 A2 | 4/2005 |
| WO | WO 2007/049098 | 5/2007 |
| WO | WO 2007/102030 | 9/2007 |
| WO | WO2008/143642 A2 | 11/2008 |
| WO | WO2009/017833 | 2/2009 |
| WO | WO2009/097331 A1 | 8/2009 |
| WO | WO2009/123316 | 8/2009 |
| WO | WO 2009/114809 | 9/2009 |
| WO | WO 2009/114814 | 9/2009 |
| WO | WO2009/151125 A1 | 12/2009 |
| WO | WO2010/010365 A1 | 1/2010 |
| WO | WO2010/014585 | 2/2010 |
| WO | WO2010/068867 | 6/2010 |
| WO | WO2010/106211 | 9/2010 |
| WO | WO 2010/132347 A2 | 11/2010 |
| WO | WO 2010/143053 A1 | 12/2010 |
| WO | WO2011/053870 | 5/2011 |
| WO | WO 2011/053870 | 5/2011 |
| WO | WO2011/097273 A1 | 8/2011 |
| WO | WO 2012/148926 | 11/2012 |
| WO | WO 2012/148927 | 11/2012 |
| WO | WO 2012/148929 | 11/2012 |
| WO | WO 2012/148930 | 11/2012 |
| WO | WO 2012/174262 A2 | 12/2012 |

OTHER PUBLICATIONS

Bada et al; Isotopic Fractionation During Peptide Bond Hydrolysis, Geochimica et Cosmoschimica Acta, 1989, vol. 53, pp. 3337-3341.

Balasubramanian et al; DNA strand breaking by the hydroxyl radical is governed by the accessible surface areas of the hydrogen atoms of the DNA backbone. Proc. Natl. Acad. Sci. USA, Aug. 1998, vol. 95 pp. 9738-9743.

Brandl et al; The biosynthesis of 3-(trans-2-Nitrocyclopropyl)alanine, a Constituent of the Signal Metabolite Hormaomycin; European Journal of Organic Chemistry, published online Dec. 20, 2004, vol. 2005, No. 1, pp. 123-135.

Brenna et al; High-Precision Continuous-Flow Isotope Ratio Mass Spectrometry; Mass Spectrometry Review; vol. 16; pp. 227-258; 1997.

Brenna et al; α-Linolenic acid supplementation and conversionton to n-3 long-chain polyunsaturated fatty acids in humans; Prostaglandins, Leukotrienes and Essential Fatty Acids; vol. 80; pp. 85-91; 2009.

Brenna, J.T.; Efficiency of conversion of a-linolenic acid to long chain n-3 fatty acids in man; Lipid Metabolism; pp. 127-132; 2002.

Brenna, J.T.; Use of stable isotopes to study fatty acid and lipoprotein metabolism in man; Prostaglandins, Leukotrienes and Essential Fatty Acids; vol. 57 (4 & 5); pp. 467-472; 1997.

Burdzy et al; Synthesis of stable-isotope enriched 5-methylpyrimidines and their use as probes of base reactivity in DNA, Nucleic Acids Research, 2002, vol. 30, No. 18, pp. 4068-4074.

Chen et al., One-Pot Selective Deuteriation of 5'-Dimethoxytritylated Deoxynucleotide Derivatives; Bioorgainc & Medicinal Chemistry Letters, vol. 4, No. 6, pp. 789-794, 1994.

Chiriac et al; Synthesis of [1,3,6,7-15N, 8-13C] adenine; Journal of Labelled Compounds and Radiopharmaceuticals; Apr. 1999 (published online May 4, 1999); vol. 42, issue 4, pp. 377-385.

Cho et al; Cooperativity and anti-cooperativity between ligand binding and the dimerization of ristocetin A: asymmetry of a homodimer complex and implications for signal transduction; Chemistry & Biology; Mar. 1996; vol. 3, issue 3, pp. 207-215.

Crombie et al. Synthesis of [14, 14-2H2]-linolenic acid and its use to confirm the pathway to 12-oxophytodienoic acid (12-oxoPDA) in plants: a conspectus of the epoxycarbonium ion derived family of metabolites from linoleic and linolenic acid hydroperoxides. Journal of the Chemical Society, Perkin Transactions 1, No. 3, 1991.

Dalle-Donne et al; Protein carbonylation in human diseases; Trends in Molecular Medicine; Apr. 2003, vol. 9, No. 4, pp. 169-176.

Demidov, V.; Heavy isotopes to avert ageing?; Trends in Biotechnology; Aug. 2007, vol. 25, No. 9, pp. 371-375.

Dyall et al, Neurological Benefits of Omega-3 Fatty Acids, Neuromolecular Medicine, vol. 10, No. 4, Jun. 10, 2008.

Emken et al; Effect of Dietary Docosahexaenoic Acid on Desaturation and Uptake in vivo of Isotope-Labeled Oleic, Linoleic, and Linolenic Acids by Male Subjects; Lipids; vol. 34, No. 8; pp. 785-791; 1999.

Emken et al; Metabolism of cis-12-octadecenoic acid and trans-9, trans-12-octadecadienoic acid and their influence on lipogenic enzyme activities in mouse liver; Biochimica et Biophysica Acta; vol. 919; pp. 111-121; 1987.

Esaki et al; Synthesis of base-selectively deuterium-labelled nucleosides by the Pd/C-Catalyzed H-D Exchange Reaction in Deuterium Oxide; Heterocycles; 2005; vol. 66, pp. 361-369.

Evans et al, ENDOR, triple resonance and ESR studies of spin-trapped radicals in autoxidized linoleic acid and its deuterated derivatives. Biochimica et Biophysica Acta—Lipids and Lipid Metabolism, Elsevier Science BV, Amsterdam, NL, vol. 835, No. 3, Jul. 31, 1985.

Extended European Search Report and Written Opinion dated Jun. 5, 2013 for EP Patent Application No. 10827578.5.

Extended European Search Report dated Jul. 12, 2011 for EP Application No. 09721095.9.

Finglas et al., Use of and Oral/intravenous Dual-Label Stable-Isotope Protocol to Determine Folic Acid Bioavailability from Fortified Cereal Grain Foods in Women; The Journal of Nutrition; American Society for Nutritional Sciences; pp. 936-939, 2002.

Foldesi et al; The Synthesis of Deuterionucleosides; Nucleosides, Nucleotides and Nucleic Acids; 2000, vol. 19, No. 10-12, pp. 1615-1656.

Geboes et al, Validation of a new test meal for a protein digestion breath test in humans, The Journal of Nutrition, vol. 134, No. 4, pp. 806-810, Apr. 2004.

Harman, Deham; The Free Radical Theory of Aging; Antioxidants & Redox Signaling; vol. 5, No. 5, pp. 557-561, Oct. 2003.

Harman, Denham; Aging and Oxidative Stress; Journal of International Federation of Clinical Chemistry (JIFCC), vol. 10, No. 1; pp. 24-26; Mar. 1998.

Hill et al. Isotope-reinforced polyunsaturated fatty acids protect yeast cells from oxidative stress. Free Radical Biology & Medicine, Jan. 1, 2011, vol. 50, pp. 130-138.

(56) References Cited

OTHER PUBLICATIONS

Hill et al; Small amounts of isotope-reinforced polyunsaturated fatty acids suppress lipid autoxidation; Free Radical Biology and Medicine, vol. 53, pp. 893-906; 2012.
Hulme et al; Chemistry and the Worm: Caenorhabditis elegans as a Platform for Integrating Chemical and Biological Research; Chemical Biology; Angewandte Chemie International Edition; vol. 50; pp. 4774-4807, 2011.
Hussein, N., Long-chain conversion of [13C] linoleic acid and -linolenic acid in response to marked changes in their dietary intake in men, The Journal of Lipid Research, vol. 46, No. 2, Dec. 1, 2004.
Ikeya et al; Evaluation of stereo-array isotope labeling (SAIL) patterns for automated structural analysis of proteins with CYANA, Magnetic Resonance in Chemistry, Jul. 2006, vol. 44, spec. No. S152-S157.
International Search Report and Written Opinion dated Sep. 10, 2010 for PCT/US2009/037173.
International Search Report and Written Opinion dated Dec. 23, 2010 for PCT/US10/54866.
International Search Report and Written Opinion dated Nov. 29, 2012 for PCT/US2012/034832.
International Search Report and Written Opinion dated Nov. 29, 2012 for PCT/US2012/034833.
International Search Report and Written Opinion dated Nov. 29, 2012 for PCT/US2012/034835.
International Search Report and Written Opinion dated Nov. 29, 2012 for PCT/US2012/034836.
International Search Report and Written Opinion dated Jun. 3, 2009 for PCT/US2009/037161.
International Search Report dated Jun. 12, 2007 for PCT/GB2007/050112.
Jacquot et al, Isotope Sensitive Branching and Kinetic Isotope Effects in the Reaction of Deuterated Arachidonic Acids with Human 12- and 15-Lipoxygenases +, Biochemistry, vol. 47, No. 27, Jun. 12, 2008.
Johnson et al, Potential role of dietary n-3 fatty acids in the prevention of dementia and macular degeneration, The American Journal of Clinical Nutrition, vol. 83, No. 6, Jun. 2006.
Kelland et al; Stereochemistry of Lysine Formation by meso-Diaminopimelate Decarboxylase from Wheat Germ: Use of 1H-13C NMR Shift Correlation to Detect Stereospecific Deuterium Labeling, Biochemistry, Jun. 1985, vol. 24, No. 13, pp. 3263-2367.
Kelly et al; Assessing the authenticity of single seed vegetable oils using fatty acid stable carbon isotope ratios (13C/12C); Food Chemistry; 1997; vol. 59, No. 2, pp. 181-186; Elsevier Science Ltd.
Kishore et al; Partial 13C Isotopic Enrichment of Nucleoside Monophosphates: Useful Reporters for NMR Structural Studies; Nucleic Acids Research; Oct. 2005, vol. 33, No. 18.
Knapp et al; Temperature-dependent isotope effects in soybean lipoxygenase-1: Correlating hydrogen tunneling with protein dynamics; JACS Articles; J. Am. Chem. Soc.; vol. 124; pp. 3865-3874; published online Mar. 20, 2002.
Kushner et al; Pharmacological uses and perspectives of heavy water and deuterated compounds; Canadian Journal of Physiology and Pharmacology; Feb. 1999; vol. 77, pp. 79-88.
Lefkowitz et al; Where Does the Developing Brain Obtain Its Docosahexaenoic Acid? Relative Contributions of Dietary α-Linolenic Acid, Docosahexaenoic Acid, and Body Stores in the Developing Rat; Pediatric Research; vol. 57, No. 1; pp. 157-165; 2005.
Levenson et al; The Healing of Rat Skin Wounds; Annals of Surgery, vol. 161, No. 2; pp. 293-308; Feb. 1965.
Lichtenstein et al; Comparison of deuterated leucine, valine and lysine in the measurement of human apolipoprotein A-I and B-100 kinetics; Journal of Lipid Research; 1990; vol. 31, No. 9, pp. 1693-1702.
Lin et al; Whole body distribution of deuterated linoleic and α-linolenic acids and their metabolites in the rat; Journal of Lipid Research; vol. 48; pp. 2709-2724; 2007.
Mazza et al, Omega-3 fatty acids and antioxidants in neurological and psychiatric diseases: An overview, Progress in Neuro-Psychopharmacology & Biological Psychiatry, Oxford, GB, vol. 31, No. 1, Dec. 22, 2006.
Nass et al; Caenorhabditis elegans in Parkinson's Disease Drug Discovery: Addressing an Unmet Medical Need; Molecular Interventions; vol. 8, Issue 6; pp. 284-293; Dec. 2008.
Notice of reasons for Rejection dated Aug. 24, 2011 for Japanese Patent Application No. 2008-557833.
Oba et al; A simple rout to L-[5,5,6,6-D4] lysine starting from L-pyroglutamic acid, Japanese Journal of Deuterium Science, 2006, vol. 12, No. 1, pp. 1-5.
Raap et al; Enantioseletive syntheses of isotopically labeled a-amino acids. Preparation of (ε-13C)-L-α-aminoadipic acid and five isotopomers of L-lysine with 13C, 15N, and 2H in the δ- and ε-positions; Recueil de Travaux Chimiques de Pays-Bas, 1990, vol. 109, No. 4, pp. 277-286.
Rapoport et al ; Delivery and turnover of plasma-derived essential PUFAs in mammalian brain ; Journal of Lipid Research; May 2001; vol. 42; pp. 678-685.
Ren et al; Simultaneous metabolic labeling of cells with multiple amino acids: localization and dynamics of histone acetylation and methylation, Proteomics: Clinical Applications; Jan. 2007; vol. 1, No. 1, pp. 130-142.
Rohwedder et al; Measurement of the Metabolic Interconversion of Deuterium-Labeled Fatty Acids by Gas Chromatography/Mass Spectrometry; Lipids; vol. 25, No. 7; pp. 401-405; 1990.
Rosen et al; Effect of Deuterium Oxide on Wound Healing, Collagen and Metabolism of Rats; New England Journal of Medicine; vol. 270, No. 22; pp. 1142-1149; May 28, 1964.
Salem et al; Arachidonic and docosahexaenoic acids are biosynthesized from their 18-carbon precursors in human infants; Proc. Natl. Acad. Sci.; vol. 93; pp. 49-54; Jan. 1996.
Scholl et al; Synthesis of 5,5,6,6-D4-L-lystine-aflatoxin B1 for use as a mass spectrometric internal standard; Journal of Labelled Compounds & Radiopharmaceuticals; Oct. 2004; vol. 47, No. 11, pp. 807-815.
Shchepinov et al, Isotopic reinforcement of essential polyunsaturated fatty acids diminishes nigrostriatal degeneration in a mouse model of Parkinson's disease, Toxicology Letter, Elsevier Biomedical Press, Amsterdam, NL, vol. 207, No. 2, pp. 97-103, Aug. 10, 2011.
Shchepinov et al. Isotope effect, essential diet components, and prospects of aging retardation. Russian Journal of General Chemistry, 2010, vol. 80, No. 7, pp. 1514-1522.
Shchepinov, Mikhail; Reactive Oxygen Species, Isotope Effect, Essential Nutrients, and Enhanced Longevity; Rejuvenation Research; 2007; vol. 10, No. 1, pp. 47-59.
Svedruzic et al; The Mechanism of Target Base Attack in DNA Cytosine Carbon 5 Methylation; Biochemistry; Aug. 2004; vol. 43, No. 36, pp. 11460-11473.
Tang et al; Kinetic and biochemical analysis of the mechanism of action of lysine 5, 6-aminomutase; Archives of Biochemistry and Biophysics; Oct. 2003; vol. 418, No. 1, pp. 49-54.
The Aldrich Catalog Handbook of Fine Chemicals 2003-2004, p. 141, catalog No. 48, 998-0.
Toyama et al; Assignments and hydrogen bond sensitivities of UV resonance Raman bands of the C8-deuterated guanine ring; Journal of Raman Spectroscopy; Sep. 2002; vol. 33, issue 9, pp. 699-708.
Tucker et al; The synthesis of 11,11-Dideuterolinoleic Acid; Journal of Labelled Compounds; vol. VII, No. 1, Jan.-Mar. 1970.
Viswanathan et al., Deuterium Nuclear Magnetic Resonance Study of the Interaction of Substrates and Inhibitors with Soybean Lipoxygenase; The Journal of Biological Chemistry; vol. 256, No. 14, Issue of Jul. 25, 1981; pp. 7155-7160.
Wade, David; Deuterium isotope effects on noncovalent interactions between molecules; Chemico-Biological Interactions; Oct. 1998; vol. 117, No. 3, pp. 191-217.
Wheeler et al., The Synthesis of the 2H, 3H, and 14C-Isotopomers of 2'-Deoxy-2', 2'-Difourocytidine Hydrochloride, and Anti-Tumor Compound; Journal of Labelled Compounds and Radiopharmaceuticals; vol. XXIX, No. 5., 1991.
Written Opinion dated Sep. 8, 2008 for PCT/GB2007/050112.

(56) References Cited

OTHER PUBLICATIONS

Yamauchi et al., Observation of the Pathway from Lysine to the Isoprenoidal Lipid of Halophilic Archaea, Halobacterium halobium and Natrinema pallidum, Using regiospecifically Deuterated Lysine; Bull. Chem. Soc. Jpn., vol. 74 (2001), pp. 2199-2205.
Wilczynska-Kwiatek A et al., "Asthma, allergy, mood disorders, and nutrition", European Journal of Medical research, Biomed Central Ltd. London, UK, vol. 14, No. Suppl 4, Dec. 7, 2009, pp. 248-254.
Mikhail S Shchepinov et al., "Isotopic reinforcement of essential polyunsaturated fatty acids diminishes nigrostriatal degeneration in a mouse model of Parkinson's disease", Toxicology Letters, Elsevier Biomedical Press, Amsterdam, NL, vol. 207, No. 2, Jul. 18, 2011, pp. 97-103.
Serhiyenko V et al., "Simvastatin and Omega-Polyunsaturated Fatty Acids in the Treatment of Cardiomyopathy in Type 2 Diabetes Mellitus Patients", Atherosclerosis Supplements, Elsevier, Amsterdam, NL, vol. 9, No. 1, May 1, 2008, p. 203.
The extended European search report for European Patent Application No. 12776313 dated Sep. 17, 2014.
Sumbalova et al., Brain energy metabolism in experimental chronic diabetes: effect of long-term administration of coenzyme Q10 and w-3 polyunsaturated fatty acids, Biologia Bratislava, 60(17): 105-108, 2005.
DiMauro, Mitochondrial Respiratory-Chain Diseases, N Engl J Med, 348:2656-68, 2003.
Rustin et al., Effect of idebenone on cardiomyopathy in Friedreich's ataxia: a preliminary study, The Lancet, 354:477-479, 1999.
Gueraud et al., Chemistry and biochemistry of lipid peroxidation products, Free Radical Research, vol. 44, No. 10, pp. 1098-1124, Oct. 2010.
Riediger et al., A Systemic Review of the Roles of n-3 Fatty Acids in Health and Disease, Journal of the American Dietetic Association, pp. 668-679, Apr. 2009.
Nelson et al., "Reduction of beta-Amyloid Levels by Novel Protein Kinase C epsilon Activators", Journal of Biological Chemistry, vol. 284, No. 50, Dec. 2009, pp. 34514-34521.
Extended European Search Report for European Application No. 12776294 dated Sep. 25, 2014 by European Patent Office.
Nobuo Tamiya and Takehiko Shimanouchi; Infra-red absorption spectra of deuterated aspartic acids; Spectrochimica Acta, vol. 18, No. 7, pp. 895-905; Jul. 1, 1962.
Office Action for U.S. Appl. No. 14/551,450 dated Apr. 15, 2015 by U.S. Patent and Trademark Office.
Townend et al., "Dietary Macronutrient Intake and Five-year Incident Cataract: The Blue Mountains Eye Study", American Journal of Ophthalmology, Elsevier, Amsterdam, NL, vol. 143, No. 6, May 22, 2007, pp. 932-939.
The extended European search report for European Patent Application No. 12776521 dated Sep. 17, 2014.
Lambert D. Rationale and applications of lipids as prodrug carriers. European Journal of Pharmaceutical Sciences. 2000;11 (Suppl.2): S 15-S27.
Hepatocellular. Hepatocellular carcinoma. Medscape Reference. 2014;1-5.
Lei et al., Dietary omega-3 Polyunsaturated Fatty Acids Enhance Adiponectin Expression and Protect Against Pressure Overload-Induced Left Ventricular Hypertrophy and Dysfunction, Journal of Cardial Failure, Churchill Livingstone, Naperville, IL, US, vol. 13m No. 6, Aug. 1, 2007, p. S79.
Extended European Search Report for European Application No. 12777440 dated Sep. 17, 2014 by European Patent Office.
Neurochem. Res., 2007, vol. 32, pp. 2184-2193.
IOVS, 2003, vol. 44, No. 8, pp. 3663-3668.
The American Journal of Human Genetics, May 15, 2009, vol. 84, pp. 558-566.
Free Radical Biology & Medicine, Oct. 16, 20008, vol. 44, pp. 1259-1272.
Journal of Gastroenterology and Hepatology, 2002, vol. 17, Suppl., pp. S186-S190.
Japanese Journal of Clinical Medicine (Separate Volume) Syndrome classified as New Fields Series 13 Liver/Biliary Tract-based Syndrome (second edition) I Liver edition (the first volume) Sep. 20, 2010 p. 196 to 201.
Separate Volume/Advances in Medical Science Oxidative Stress Ver.2 Oct. 5, 2006, p. 23 to 27.
Giordano, F.J., The Journal of Clinical Investigation, (Mar. 2005) vol. 115, No. 3, p. 500-508.
Keiji Yoneya et al., Japanese Journal of Clinical Medicine(Oct. 1, 1998)vol. 56, No. 10 p. 51-56(2509-2514).
Journal of Biliary Tract & Pancreas, 2005, vol. 26, No. 4, p. 351-357.
Dentistry Dictionary reduced-size edition. Oct. 10, 1989, the first edition, p. 2216-2217.
Office Action for Japanese Patent Application No. 2014-508488 dated Dec. 4, 2015.
Office Action for Japanese Patent Application No. 2014-508487 dated Dec. 3, 2015.
Office Action for U.S. Appl. No. 12/916,347 dated Oct. 22, 2015.
Office Action for U.S. Appl. No. 12/916,347 dated Jul. 12, 2013.
S.C. Barber et al., *Biochimica et Biophysica Acta* 1762 (2006) 1051-1067.
Simpson et al., Neurology. May 25, 2004;62(10):1758-65.
Pedersen et al., Annals of Neurology (Nov. 1998), vol. 44, Issue 5, pp. 819-824.
Mitsumoto et al., Amyotroph Lateral Scler. (2008); 9(3): 177-183.
Veldink et al., *J Neurol Neurosvrg Psychiatry*. (2007) 78:367-371.
Australian Government, IP Australia, Examination Report No. 2 for Standard Patent Application, dated May 1, 2017, for Australia Application No. 2012249918.
Australian Government, IP Australia, Examination Report No. 3 for Standard Patent Application, dated May 16, 2017, for Australia Application No. 2012249918.
Australian Government, IP Australia, Notice of Acceptance for Patent Application, dated May 31, 2017, for Application No. 2012249918.
Office Action dated Apr. 13, 2018 for Canadian Application No. 2,834,342.

* cited by examiner

IMPAIRED ENERGY PROCESSING DISORDERS AND MITOCHONDRIAL DEFICIENCY

CROSS-REFERENCE TO RELATED APPLICATIONS

This application is a U.S. National Phase Application of PCT International Application Number PCT/US2012/034833, filed on Apr. 24, 2012, designating the United States of America and published in the English language, which is an International Application of and claims the benefit of priority to U.S. Provisional Application No. 61/479,288, filed Apr. 26, 2011; which are hereby expressly incorporated by reference in their entireties.

BACKGROUND

Field

Isotopically modified polyunsaturated fatty acids ("PUFAs") and other modified PUFAs for treating certain diseases, particularly impaired energy processing disorders and mitochondrial deficiencies.

Description of the Related Art

Oxidative stress is implicated in a wide variety of diseases such as mitochondrial diseases, neurodegenerative diseases, inborn error's of metabolism, diabetes, diseases of the eye, kidney diseases, liver diseases, and cardiac diseases. Specifically, such diseases include but are not limited to impaired energy processing disorders and mitochondrial deficiencies.

While the number of diseases associated with oxidative stress are numerous and diverse, it is well established that oxidative stress is caused by disturbances to the normal redox state within cells. An imbalance between routine production and detoxification of reactive oxygen species ("ROS") such as peroxides and free radicals can result in oxidative damage to cellular structures and machinery. Under normal conditions, potentially important sources of ROSs in aerobic organisms is the leakage of activated oxygen from mitochondria during normal oxidative respiration. Additionally, it is known that macrophages and enzymatic reactions also contribute to the generation of ROSs within cells. Because cells and their internal organelles are lipid membrane-bound, ROSs can readily contact membrane constituents and cause lipid oxidation. Ultimately, such oxidative damage can be relayed to other biomolecules within the cell, such as DNA and proteins, through direct and indirect contact with activated oxygen, oxidized membrane constituents, or other oxidized cellular components. Thus, one can readily envision how oxidative damage may propagate throughout a cell give the mobility of internal constituents and the interconnectedness of cellular pathways.

Lipid-forming fatty acids are well-known as one of the major components of living cells. As such, they participate in numerous metabolic pathways, and play an important role in a variety of pathologies. Polyunsaturated Fatty Acids ("PUFAs") are an important sub-class of fatty acids. An essential nutrient is a food component that directly, or via conversion, serves an essential biological function and which is not produced endogenously or in large enough amounts to cover the requirements. For homeothermic animals, the two rigorously essential PUFAs are linoleic (cis,cis-9,12-Octadecadienoic acid; (9Z,12Z)-9,12-Octadecadienoic acid; "LA"; 18:2; n-6) and alpha-linolenic (cis,cis,cis-9,12,15-Octadecatrienoic acid; (9Z,12Z,15Z)-9,12,15-Octadecatrienoic acid; "ALA"; 18:3; n-3) acids, formerly known as vitamin F (Cunnane S C. Progress in Lipid Research 2003; 42:544-568). LA, by further enzymatic desaturation and elongation, is converted into higher n-6 PUFAs such as arachidonic (AA; 20:4; n-6) acid; whereas ALA gives rise to a higher n-3 series, including, but not limited to, eicosapentaenoic acid (EPA; 20:5; n-3) and docosahexaenoic (DHA; 22:6; n-3) acid (Goyens P L. et al. Am. J. Clin. Nutr. 2006; 84:44-53). Because of the essential nature of certain PUFAs or PUFA precursors, there are many known instances of their deficiency and these are often linked to medical conditions. Furthermore, many PUFA supplements are available over-the-counter, with proven efficiency against certain ailments (See, for example, U.S. Pat. Nos. 7,271,315 and 7,381,558).

PUFAs endow mitochondrial membranes with appropriate fluidity necessary for optimal oxidative phosphorylation performance. PUFAs also play an important role in initiation and propagation of the oxidative stress. PUFAs react with ROS through a chain reaction that amplifies an original event (Sun M, Salomon R G, J. Am. Chem. Soc. 2004; 126:5699-5708). However, non-enzymatic formation of high levels of lipid hydroperoxides is known to result in several detrimental changes. Indeed, Coenzyme Q10 has been linked to increased PUFA toxicity via PUFA peroxidation and the toxicity of the resulting products (Do T Q et al, PNAS USA 1996; 93:7534-7539). Such oxidized products negatively affect the fluidity and permeability of their membranes; they lead to oxidation of membrane proteins; and they can be converted into a large number of highly reactive carbonyl compounds. The latter include reactive species such as acrolein, malonic dialdehyde, glyoxal, methylglyoxal, etc. (Negre-Salvayre A, et al. Brit. J. Pharmacol. 2008; 153:6-20). But the most prominent products of PUFA oxidation are alpha, beta-unsaturated aldehydes such as 4-hydroxynon-2-enal (4-HNE; formed from n-6 PUFAs like LA or AA), 4-hydroxyhex-2-enal (4-HHE; formed from n-3 PUFAs like ALA or DHA), and corresponding ketoaldehydes (Esterfbauer H, et al. Free Rad. Biol. Med. 1991; 11:81-128; Long E K, Picklo M J. Free Rad. Biol. Med. 2010; 49:1-8). These reactive carbonyls cross-link (bio) molecules through Michael addition or Schiff base formation pathways, and have been implicated in a large number of pathological processes (such as those introduced above), age-related and oxidative stress-related conditions, and aging. Importantly, in some cases, PUFAs appear to oxidize at specific sites because methylene groups of 1,4-diene systems (the bis-allylic position) are substantially less stable to ROS, and to enzymes such as cyclogenases and lipoxygenases, than allylic methylenes.

We have now discovered that oxidation resistant PUFAs, PUFA mimetics, PUFA pro-drugs and/or fats containing oxidation resistant PUFAs and PUFA mimetics that are useful for mitigating and/or treating impaired energy processing disorders and mitochondrial deficiencies.

SUMMARY

Some embodiments provide a method of treating or inhibiting the progression of impaired energy processing disorders or mitochondrial deficiencies, comprising administering an effective amount of a polyunsaturated substance to a patient having an impaired energy processing disorder or mitochondrial deficiency and in need of treatment, wherein the polyunsaturated substance is chemically modified such that one or more bonds are stabilized against oxidation, wherein the polyunsaturated substance or a polyunsaturated metabolite thereof comprising said one or more stabilized bonds is incorporated into the patient's body following administration.

In some embodiments, the polyunsaturated substance is a nutrition element. In other embodiments, the nutrition element is a fatty acid, a fatty acid mimetic, and/or a fatty acid pro-drug. In other embodiments, the nutrition element is a triglyceride, a diglyceride, and/or a monoglyceride comprising a fatty acid, a fatty acid mimetic, and/or a fatty acid pro-drug. In some embodiments, the fatty acid, fatty acid mimetic, or fatty acid pro-drug is stabilized at one or more bis-allylic positions. In other embodiments, the stabilization comprises at least one $^{13}C$ atom or at least one deuterium atom at a bis-allylic position. In some embodiments, the stabilization comprises at least two deuterium atoms at one or more bis-allylic position. In other embodiments, the stabilization utilizes an amount of isotopes that is above the naturally-occurring abundance level. In some embodiments, the stabilization utilizes an amount of isotopes that is significantly above the naturally-occurring abundance level of the isotope.

In some embodiments, the fatty acid, fatty acid mimetic, or fatty acid pro-drug has an isotopic purity of from about 20%-99%. In other embodiments, the isotopically stabilized fatty acids, fatty acid mimetics, or fatty acid pro-drugs are administered to a patient along with non-stabilized fatty acids, fatty acid mimetics, or fatty acid pro-drugs. In some embodiments, the isotopically stabilized fatty acids, fatty acid mimetics, or fatty acid pro-drugs comprise between about 1% and 100%, between about 5% and 75%, between about 10% and 30%, or about 20% or more of the total amount of fatty acids, fatty acid mimetics, or fatty acid pro-drugs administered to the patient. In some embodiments, the patient ingests the fatty acid, fatty acid mimetic, or fatty acid pro-drug. In some embodiments, a cell or tissue of the patient maintains a sufficient concentration of the fatty acid, fatty acid mimetic, fatty acid pro-drug, triglyceride, diglyceride, and/or monoglyceride to prevent autooxidation of the naturally occurring polyunsaturated fatty acid, mimetic, or ester pro-drug. In some embodiments, the stabilization utilizes an amount of isotope that is significantly above the naturally-occurring abundance level of said isotope.

In some embodiments, the method utilizes a fatty acid, fatty acid mimetic, or fatty acid pro-drug that is an omega-3 fatty acid and/or an omega-6 fatty acid. In other embodiments, the fatty acid selected from the group consisting of 11,11-D2-linolenic acid, 14,14-D2-linolenic acid, 11,11,14,14-D4-linolenic acid, 11,11-D2-linoleic acid, 14,14-D2-linoleic acid, 11,11,14,14-D4-linoleic acid, II-D-linolenic acid, 14-D-linolenic acid, 11,14-D2-linolenic acid, II-D-linoleic acid, 14-D-linoleic acid, and 11,14-D2-linoleic acid. In other embodiments, the fatty acids are further stabilized at a pro-bis-allylic position. In some embodiments, the fatty acid is alpha linolenic acid, linoleic acid, gamma linolenic acid, dihomo gamma linolenic acid, arachidonic acid, and/or docosatetraenoic acid. In some embodiments, the fatty acid is incorporated into the mitochondrial membrane. In other embodiments, the fatty acid pro-drug is an ester. In some embodiments, the ester is a triglyceride, diglyceride, or monoglyceride.

Some embodiments further comprise co-administering an antioxidant. In some embodiments, the antioxidant is Coenzyme Q, idebenone, mitoquinone, or mitoquinol. In some embodiments, the antioxidant is a mitochondrially-targeted antioxidant. In some embodiments, the antioxidant is a vitamin, vitamin mimetic, or vitamin pro-drug. In other embodiments, the antioxidant is a vitamin E, vitamin E mimetic, vitamin E pro-drug, vitamin C, vitamin C mimetic, and/or vitamin C pro-drug.

DETAILED DESCRIPTION OF THE PREFERRED EMBODIMENT

Figures 1A, 1B:
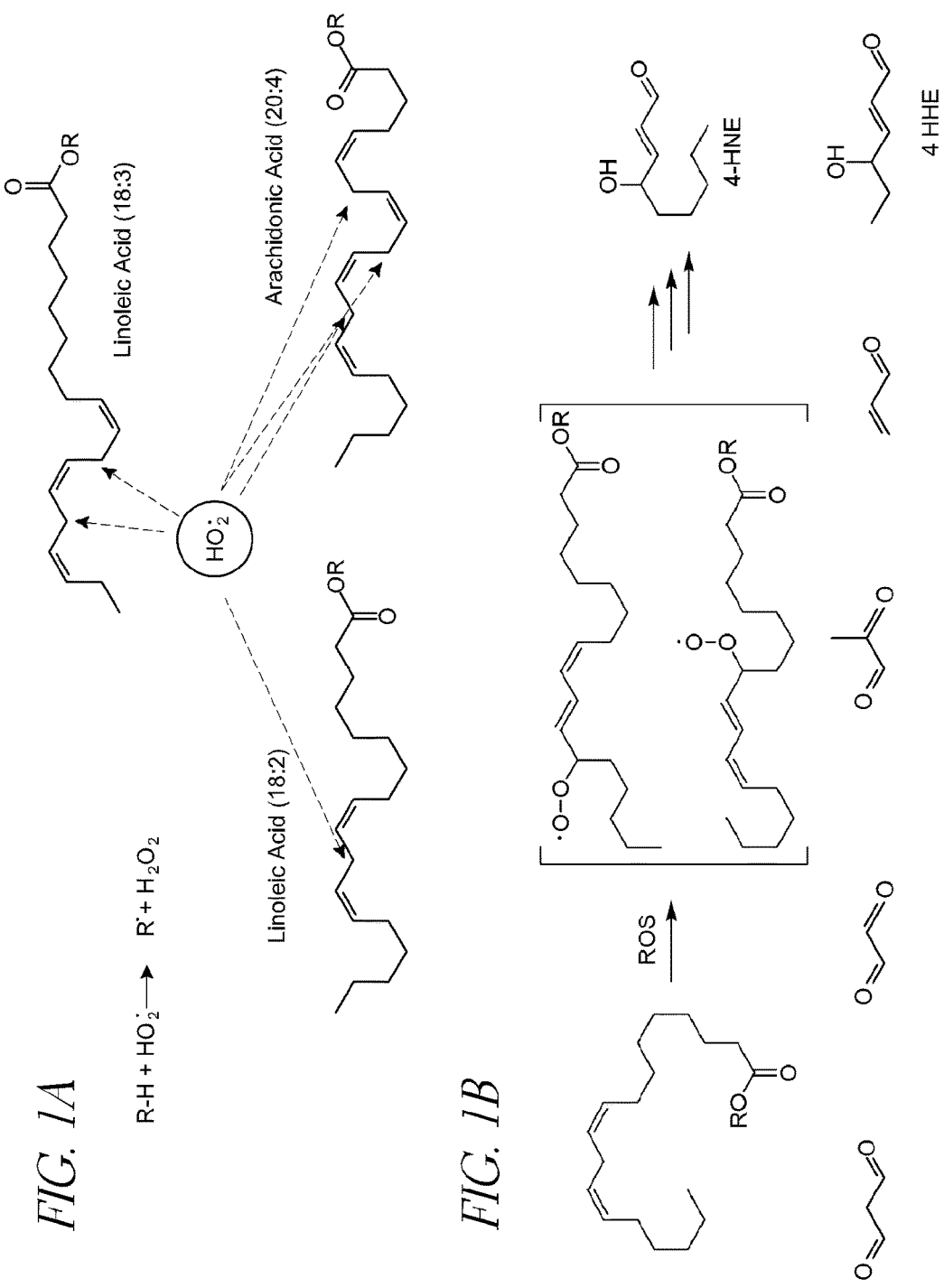
FIGS. 1A and 1B. (1A) ROS-driven oxidation of PUFAs; (1B) formation of toxic carbonyl compounds.

As used herein, abbreviations are defined as follows:
αLnn Alpha-linolenic acid
4-HHE or HHE 4-Hydroxyhex-2-enal
4-HNE or HNE 4-Hydroxynon-2-enal
AA Arachidonic acid
AcOH Acetic acid
ALA Alpha-linolenic acid
AMVN 2,2'-Azobis(2,4-dimethylvaleronitrile)
BD Bipolar Disorder
D Deuterated
D1 Mono-deuterated
D2 Di-deuterated
D2-LA Di-deuterated linoleic acid
D3 Tri-deuterated
D4 Tetra-deuterated
D5 Penta-deuterated
D6 Hexa-deuterated
DAD Diabetes mellitus and deafness
DHA Docosahexaenoic (22:6; n–3) acid
DMF Dimethylformamide
DS Down's Syndrome
EPA Eicosapentaenoic (20:5; n–3) acid
EtOAc Ethyl acetate
EtOH Ethanol
FA Friedreich's ataxia
FAME Fatty acid methyl ester
HPMC 6-Hydroxy-2,2,5,7,8-pentamethylbenzochroman
H-PUFA Non-deuterated polyunsaturated fatty acid
IP Intraperitoneal
IR Infrared
KIE Kinetic isotope effect
LA Linoleic acid
LDL Low-density lipoprotein
LHON Leber's hereditary optic neuropathy
MELAS Mitochondrial myopathy, encephalopathy, lactic acidosis, and stroke syndrome
MERRF Myoclonus Epilepsy Associated with Ragged-Red Fibers syndrome
MIDD Maternally inherited diabetes and deafness
MNGIE Mitochondrial neuro gastrointestinal encephalomyopathy
MVEC Microvascular endothelial cells
NARP Neuropathy, ataxia, retinitis pigmentosa, and ptosis
NINCDS Neurological and Communicative Disorders and Stroke
Ox-Phos Oxidative phosphorylation
PUFA(s) Polyunsaturated fatty acid(s)
R$_{IN}$ Rate of initiation
ROS Reactive oxygen species
R$_{OX}$ Rate of oxidation
RPE Retinal pigment epithelium
SNOMED Systematized Nomenclature of Medicine
TDMS Toxicology Data Management System
TH Tyrosine hydroxylase
THF Tetrahydrofuran
TLC Thin layer chromatography
V-SMOW Vienna standard mean ocean water
WT Wild type
X-ALD X-linked Adrenoleukodystrophy
YPD Medium containing 1% Bacto-yeast extract, 2% Bacto-peptone, 2% dextrose Impaired Energy Processing Disorders and Mitochondrial Deficiency Mitochondrial disorders can be caused by genetic mutations (both in mitochondrial and nuclear DNA) as well as by environmental factors. Mitochondrial deficiency or mitochondrial respiration deficiency diseases include diseases and disorders caused by oxidation of mitochondrial membrane elements, such as mitochondrial respiration deficiency, which occurs in the mitochondrial membrane. Membrane functionality is important to overall mitochondrial function. Oxidative phosphorylation (Ox-Phos) pathways are located in the inner mitochondrial membrane rich which is rich in linoleic acid-containing phospholipid cardiolipin. Any imbalance in ROS processing may thus result in increased autoxidation of this and other membrane PUFAs, giving rise to increased levels of reactive carbonyl compounds. Some of these can initiate, up-, and down-regulate numerous processes such as activation/deactivation of uncoupling protein-2 (UCP-2), apoptosis, etc. A substantial number of diseases are linked to mitochondrial dysfunction. These diseases include, but are not limited to: Co-enzyme Q deficiency; Diabetes mellitus and deafness (DAD), and Maternally Inherited Diabetes and Deafness (MIDD); Friedreich's ataxia (FA); Leber's congenital amaurosis; Leber's hereditary optic neuropathy (LHON); Leigh syndrome; Mitochondrial myopathy, encephalopathy, lactic acidosis, and stroke (MELAS) syndrome; Mitochondrial neurogastrointestinal encephalomyopathy (MNGIE); Myoclonus Epilepsy Associated with Ragged-Red Fibers (MERRF) syndrome; Myoneurogenetic gastrointestinal encephalopathy (MNGIE) and neuropathy; Neuropathy, ataxia, retinitis pigmentosa, and ptosis (NARP); optic neuropathies and opthalmoplegias; Wolff-Parkinson-White syndrome and other cardiomyopathies; X-linked Adrenoleukodystrophy (X-ALD), as well as diseases of musculoskeletal system (lipid myopathies, chronic fatigue, fibromyalgia syndrome); kidney (Fanconi's syndrome and glomerulonephropathies); blood (Pearson's syndrome), and brain (migraines, seizures, and strokes). See Santos et al. *Antioxidants & Redox Signaling* (2010), 13:5, 651-690; Meier et al. *J. Neurol.* (2011) PMID: 21779958; Marobbio et al. *Mitochondrion* (2011) PMID: 21782979; Orsucci et al. *Curr. Med. Chem.* (2011) 18:26, 4053-64; Lynch et al. *Arch. Neurol.* (2010) 67:8, 941-947; Schultz et al. *J. Neurol.* (2009) 256 Suppl. 1:42-5; Drinkard et al. *Arch. Phys. Med. Rehabil.* (2010) 91:7, 1044-1050; Berger et al. *Brain Pathol.* (2010) 20:4, 845-856; Singh et al. *Brain Pathol.* (2010) 20:4, 838-844; Lopez-Erauskin et al. *Ann Neurol.* (2011) 70, 84-92. These and other mitochondrial diseases have increased ROS levels and as a corollary, sustain increased damage to cellular components such as lipids (McKenzie M et al, *Neurochem Res* 2004; 29:589-600). For example, early oxidative damage in spinal cord and other tissues has been observed using lipid and amino acid peroxidation biomarkers underlying neurodegeneration in X-ALD (Fourcade S. et al., *Human Mol Genetics* 2008; 17:1762-1773).

More specifically, Coenzyme Q deficiency is associated with many diseases, including nervous system diseases (dyskinesias, ataxias); musculoskeletal diseases (muscle weakness, neuromuscular diseases); metabolic diseases etc. Q10 plays an important role in controlling the oxidative stress. Q10- has been shown to be linked to increased PUFA toxicity, through PUFA peroxidation and toxicity of the formed products (Do T Q et al, *PNAS USA* 1996; 93:7534-7539). Numerous diagnostic tests are known in the art to identify subjects having a Coenzyme Q10 deficiency. In FA, the deficiency in a mitochondrial protein frataxin leads to iron accumulation within the mitochondria and a consequent increase in oxidative stress, through both Haber-Weiss—Fenton-type processes and a breakdown in the respiratory chain. (Bradley J L et al, *Hum. Mol. Genet.* 2000; 9:275-282). Lipid peroxidation is increased in FA, and reducing the level of this peroxidation has a strong protective effect (Navarro J A et al, *Hum. Mol. Genet.* 2010; 19:2828-2840). DAD and MIDD are characterised by a substantially elevated oxidative stress level (Aladaq I et al, *J. Laryngol. Otol.* 2009; 123:957-963). These, and many other mitochondrial diseases, are often characterised by accumulation of both mitochondria and lipid droplets, leading to increased lipid peroxidation (Narbonne H et al, *Diabetes Metab.* 2004; 30:61-66). Conditions like LHON and Leber's syndrome result from the mutations in a gene encoding for a subunit of the mitochondrial NADH dehydrogenase, compromising the performance of Complex I and leading to increased ROS generation (Wallace D C *Science* 1999; 283:1482-1488). MERRF is associated with both elevated oxidative stress level and abnormal lipid storage (Wu S B et al, *Mol. Neurobiol.* 2010; 41:256-266). MNGIE and NARP are another two similar examples (Wallace D C *Science* 1999; 283:1482-1488). X-ALD, which can be slowed by a combination of Lorenzo's oil and a low fat diet, is linked to both overproduction of ROS and a deficit in ROS scavenging (Al-Omar M A. *J. Herb. Pharmacother.* 2006; 6:125-134).

Mental Disorders Implicating Oxidative Stress

Down's Syndrome (DS)

DS (trisomy of chromosome 21) is associated with premature aging and mental retardation similar to Alzheimer's disease. The incidence of autoimmune diseases and cataracts is also elevated, pointing to increased oxidative stress in individuals with DS (Jovanovic S V, et al. *Free Rad. Biol. Med.* 1998; 25:1044-1048). Chromosome 21 codes for Cu/Zn SOD and amyloid beta-peptide, so the DS is characterised by the overflow of these gene products and metabolites, notably an increased ratio of SOD to catalase, accompanied by excessive $H_2O_2$ (Sinet P M. *Ann. NY Acad. Sci.* 1982; 396:83-94). In individuals with DS, the markers of protein and lipid oxidation (MDA, HNE, etc), and advanced glycation and lipoxidation end-products, are significantly increased (Busciglio J, Yankner B A. *Nature* 1995; 378:776-779; Odetti P, et al. *Biochem. Biophys. Res. Comm.* 1998; 243:849-851). Mitochondrial dysfunction has also been linked with the etiology of Down's Syndrome dementia. Coskun et al. *Journal of Alzheimer's Disease* (2010) 20, S293-S310. The importance of oxidative stress in DS led to widespread attempts to reduce the side-effect of oxidation by employing antioxidants; but recent randomised trials found no evidence of efficiency of antioxidant supplements (Ellis J M, et al. *Brit. Med. J.* 2008; 336:594-597). Subjects with Down Syndrome may be identified by standard chromosomal testing.

Schizophrenia and Bipolar Disorder (BD)

PUFAs are known to influence neurodevelopment and some psychiatric disorders, such as schizophrenia. DHA, eicosapentaenoic acid (EPA) and AA are of particular importance in this regard. In schizophrenia, there is a positive correlation between EPA supplementation and the improvement of some symptoms, (Luzon-Toro B, et al. *Neurol. Psychiatr. Brain Res.* 2004; 11:149-160). There is a significant increase in oxidative stress and HNE levels in both Schizophrenia and BD (Wang J F, et al. *Bipolar Disorders* 2009; 11:523-529). Synaptic dysfunction is known to be an early pathogenic event in neuropathologies such as AD, ALS, PD, etc. (LoPachin R M et al *Neurotoxicol.* 2008; 29:871-882). Although the molecular mechanism of this synaptotoxicity is not known, published evidence suggests that these diseases are characterized by a common pathophysiological cascade involving oxidative stress, PUFA peroxidation (FIG. 1) and the subsequent liberation of α,β-unsaturated carbonyl derivatives such as acrolein and 4-HNE.

Autism

Autism is a family of developmental disorders of unknown origin. The disorder is characterized by behavioral, developmental, neuropathological and sensory abnormalities, and is usually diagnosed between the ages of 2 and 10 with peak prevalence rates observed in children aged 5-8 years. The inability to combat oxidative stress has been suggested as a facilitator of the autistic disease state (Bowers et al. "Glutathione pathway gene variation and risk of autism spectrum disorders"; *J. Neurodev. Disord.;* 2011; March 5th e-pub.) Indeed, increased vulnerability to oxidative stress has been considered one unifying concept of the disorder (Ratajczak. "Theoretical Aspectes of Autism: Biomarkers—A Review" *J. Immunotoxicol.* 2011; 8(1):80-94). Furthermore, abnormal mitochondrial metabolism has also been identified as a common molecular underpinning of the disorder (Lintas et al. "Genome-wide expression studies in Autism spectrum disorder, Rett syndrome, and Down Syndrome" Neurobiol Dis. 2010 Dec. 2 e-pub). Studies also indicate that autistic patients have significantly different fatty acid levels, including PUFA levels, compared to age-matching controls (El-Ansary et al. "Plasma fatty acids as diagnostic markers in autistic patients from Saudi Arabia." *Lipids in Health and Disease* 2011, 10:62, published online 21 Apr. 2011).

Huntington's Disease

Huntington's disease (HD) is a neurodegenerative disease characterized by selective neuronal degeneration that leads to progressive disability from movement disorder, psychiatric, and cognitive impairment. HD results from a cytosine-adenine-guanine (CAG) repeat expansion in the huntingtin gene, resulting in a mutant protein that causes neuronal dysfunction and eventual cell death by implicating transcriptional impairment, excitotoxicity, oxidative damage, inflammation, apoptosis, and mitochondrial dysfunction. Oxidative stress-related damage occurs to lipids, along with proteins and deoxyribonucleic acid (DNA). Impaired expression and function of peroxisome proliferator-activated receptor gamma coactivator-1α (PGC-1α) is also implicated in the disease. A deficiency of PGC-1α increases vulnerability to oxidative stress as well as striatal degeneration. Further supporting the importance of oxidative-stress in the disease, antioxidants are effective in slowing disease progression in transgenic mouse models of HD. Moreover, ROS and the damaged caused by such species is recognized as a major contributor to neuronal loss in HD. See Johri et al., Biocehmica et Biophysica Acta (2011), doi:10.1016/j/bbadis.2011.11.014; Patten et al., *Journal of Alzheimer's Disease* (2010) 20: S357-S367.

Some aspects of this invention arise from: (1) an understanding that while essential PUFAs are vital for proper functioning of lipid membranes, and in particular of the mitochondrial membranes, their inherent drawback, i.e., the propensity to be oxidized by ROS with detrimental outcome, is implicated in Impaired Energy Processing Disorders and Mitochondrial Deficiencies; (2) antioxidants cannot prevent PUFA peroxidation due to stochastic nature of the process and the stability of PUFA peroxidation products (reactive carbonyls) to antioxidant treatment, and (3) the ROS-driven damage of oxidation-prone sites within PUFAs may be overcome by using an approach that makes them less amenable to such oxidations, without compromising any of their beneficial physical properties. Some aspects of this invention describe the use of the isotope effect to achieve this, only at sites in essential PUFAs and PUFA precursors that matter most for oxidation, while other aspects contemplate other sites in addition to those that matter most for oxidation.

Isotopically labeled embodiments should have minimal or non-existent effects on important biological processes. For example, the natural abundance of isotopes present in biological substrates implies that low levels of isotopically labeled compounds should have negligible effects on biological processes. Additionally, hydrogen atoms are incorporated into biological substrates from water, and is it known that the consumption of $D_2O$, or heavy water, does not pose a health threat to humans. See, e.g., "Physiological effect of heavy water." *Elements and isotopes: formation, transformation, distribution.* Dordrecht: Kluwer Acad. Publ. (2003) pp. 111-112 (indicating that a 70 kg person might drink 4.8 liters of heavy water without serious consequences). Moreover, many isotopically labeled compounds are approved by the U.S. Food & Drug Administration for diagnostic and treatment purposes.

It will be appreciated by those skilful in the art that the same effect can be achieved by protecting oxidation-prone positions within PUFAs using other chemical approaches. Certain PUFA mimetics, while possessing structural similarity with natural PUFAs, will nevertheless be stable to ROS-driven oxidation due to structural reinforcement.

Compositions:

In some embodiments, an isotopically modified polyunsaturated fatty acid or a mimetic refers to a compound having structural similarity to a naturally occurring PUFA that is stabilized chemically or by reinforcement with one or more isotopes, for example $^{13}C$ and/or deuterium. Generally, if deuterium is used for reinforcement, one or both hydrogens on a methylene group may be reinforced.

Some aspects of this invention provide compounds that are analogues of essential PUFAs with one, several, or all bis-allylic positions substituted with heavy isotopes. In some embodiments, the $CH_2$ groups, which will become the bis-allylic position in a PUFA upon enzymatic conversion, are substituted with one or two heavy isotopes. Such compounds are useful for the prevention or treatment of diseases in which PUFA oxidation is a factor or can contribute to disease progression.

The bis-allylic position generally refers to the position of the polyunsaturated fatty acid or mimetic thereof that corresponds to the methylene groups of 1,4-diene systems. The pro-bis-allylic position refers to the methylene group that becomes the bis-allylic position upon enzymatic desaturation.

In some embodiments, the chemical identity of PUFAs, i.e., the chemical structure without regard to the isotope substitutions or substitutions that mimic isotope substitutions, remains the same upon ingestion. For instance, the chemical identity of essential PUFAs, that is, PUFAs that mammals such as humans do not generally synthesize, may remain identical upon ingestion. In some cases, however, PUFAs may be further extended/desaturated in mammals, thus changing their chemical identity upon ingestion. Similarly with mimetics, the chemical identity may remain unchanged or may be subject to similar extension/desaturation. In some embodiments, PUFAs that are extended, and optionally desaturated, upon ingestion and further metabolism may be referred to as higher homologs.

In some embodiments, naturally-occurring abundance level refers to the level of isotopes, for example $^{13}C$ and/or deuterium that may be incorporated into PUFAs that would be relative to the natural abundance of the isotope in nature. For example, $^{13}C$ has a natural abundance of roughly 1% $^{13}C$ atoms in total carbon atoms. Thus, the relative percentage of carbon having greater than the natural abundance of $^{13}C$ in PUFAs may have greater than the natural abundance level of roughly 1% of its total carbon atoms reinforced with $^{13}C$, such as 2%, but preferably about 5%, 10%, 15%, 20%, 25%, 30%, 35%, 40%, 45%, 50%, 65%, 60%, 65%, 70%, 75%, 80%, 85%, 90%, 95%, or 100% of $^{13}C$ with respect to one or more carbon atoms in each PUFA molecule. In other embodiments, the percentage of total carbon atoms reinforced with $^{13}C$ is at least 5%, 10%, 15%, 20%, 25%, 30%, 35%, 40%, 45%, 50%, 65%, 60%, 65%, 70%, 75%, 80%, 85%, 90%, 95%, or 100%.

Regarding hydrogen, in some embodiments, deuterium has a natural abundance of roughly 0.0156% of all naturally occurring hydrogen in the oceans on earth. Thus, a PUFA having greater that the natural abundance of deuterium may have greater than this level or greater than the natural abundance level of roughly 0.0156% of its hydrogen atoms reinforced with deuterium, such as 0.02%, but preferably about 5%, 10%, 15%, 20%, 25%, 30%, 35%, 40%, 45%, 50%, 65%, 60%, 65%, 70%, 75%, 80%, 85%, 90%, 95%, or 100% of deuterium with respect to one or more hydrogen atoms in each PUFA molecule. In other embodiments, the percentage of total hydrogen atoms reinforced with deuterium is at least 5%, 10%, 15%, 20%, 25%, 30%, 35%, 40%, 45%, 50%, 65%, 60%, 65%, 70%, 75%, 80%, 85%, 90%, 95%, or 100%.

In some aspects, a composition of PUFAs contains both isotopically modified PUFAs and isotopically unmodified PUFAs. The isotopic purity is a comparison between a) the relative number of molecules of isotopically modified PUFAs, and b) the total molecules of both isotopically modified PUFAs and PUFAs with no heavy atoms. In some embodiments, the isotopic purity refers to PUFAs that are otherwise the same except for the heavy atoms.

In some embodiments, isotopic purity refers to the percentage of molecules of an isotopically modified PUFAs in the composition relative to the total number of molecules of the isotopically modified PUFAs plus PUFAs with no heavy atoms. For example, the isotopic purity may be about 5%, 10%, 15%, 20%, 25%, 30%, 35%, 40%, 45%, 50%, 65%, 60%, 65%, 70%, 75%, 80%, 85%, 90%, 95%, or 100% of the molecules of isotopically modified PUFAs relative to the total number of molecules of both the isotopically modified PUFAs plus PUFAs with no heavy atoms. In other embodiments, the isotopic purity is at least 5%, 10%, 15%, 20%, 25%, 30%, 35%, 40%, 45%, 50%, 65%, 60%, 65%, 70%, 75%, 80%, 85%, 90%, 95%, or 100%. In some embodiments, isotopic purity of the PUFAs may be from about 10%-100%, 10%-95%, 10%-90%, 10%-85%, 10%-80%, 10%-75%, 10%-70%, 10%-65%, 10%-60%, 10%-55%, 10%-50%, 10%-45%, 10%-40%, 10%-35%, 10%-30%, 10%-25%, or 10%-20% of the total number of molecules of the PUFAs in the composition. In other embodiments, isotopic purity of the PUFAs may be from about 15%-100%, 15%-95%, 15%-90%, 15%-85%, 15%-80%, 15%-75%, 15%-70%, 15%-65%, 15%-60%, 15%-55%, 15%-50%, 15%-45%, 15%-40%, 15%-35%, 15%-30%, 15%-25%, or 15%-20% of the total number of molecules of the PUFAs in the composition. In some embodiments, isotopic purity of the PUFAs may be from about 20%-100%, 20%-95%, 20%-90%, 20%-85%, 20%-80%, 20%-75%, 20%-70%, 20%-65%, 20%-60%, 20%-55%, 20%-50%, 20%-45%, 20%-40%, 20%-35%, 20%-30%, or 20%-25% of the total number of molecules of the PUFAs in the composition. Two molecules of an isotopically modified PUFA out of a total of 100 total molecules of isotopically modified PUFAs plus PUFAs with no heavy atoms will have 2% isotopic purity, regardless of the number of heavy atoms the two isotopically modified molecules contain.

In some aspects, an isotopically modified PUFA molecule may contain one deuterium atom, such as when one of the two hydrogens in a methylene group is replaced by deuterium, and thus may be referred to as a "D1" PUFA. Similarly, an isotopically modified PUFA molecule may contain two deuterium atoms, such as when the two hydrogens in a methylene group are both replaced by deuterium, and thus may be referred to as a "D2" PUFA. Similarly, an isotopically modified PUFA molecule may contain three deuterium atoms and may be referred to as a "D3" PUFA. Similarly, an isotopically modified PUFA molecule may contain four deuterium atoms and may be referred to as a "D4" PUFA. In some embodiments, an isotopically modified PUFA molecule may contain five deuterium atoms or six deuterium atoms and may be referred to as a "D5" or "D6" PUFA, respectively.

The number of heavy atoms in a molecule, or the isotopic load, may vary. For example, a molecule with a relatively low isotopic load may contain about 1, 2, 3, 4, 5, or 6 deuterium atoms. A molecule with a moderate isotopic load may contain about 10, 11, 12, 13, 14, 15, 16, 17, 18, 19, or 20 deuterium atoms. In a molecule with a very high load, every hydrogen may be replaced with a deuterium. Thus, the isotopic load refers to the percentage of heavy atoms in each PUFA molecule. For example, the isotopic load may be about 5%, 10%, 15%, 20%, 25%, 30%, 35%, 40%, 45%, 50%, 65%, 60%, 65%, 70%, 75%, 80%, 85%, 90%, 95%, or 100% of the number of the same type of atoms in comparison to a PUFA with no heavy atoms of the same type (e.g. hydrogen would be the "same type" as deuterium). In some embodiments, the isotopic load is at least 5%, 10%, 15%, 20%, 25%, 30%, 35%, 40%, 45%, 50%, 65%, 60%, 65%, 70%, 75%, 80%, 85%, 90%, 95%, or 100%. Unintended side effects are expected to be reduced where there is high isotopic purity in a PUFA composition but low isotopic load in a given molecule. For example, the metabolic pathways will likely be less affected by using a PUFA composition with high isotopic purity but low isotopic load.

One will readily appreciate that when one of the two hydrogens of a methylene group is replaced with a deuterium atom, the resultant compound may possess a stereocenter. In some embodiments, it may be desirable to use racemic compounds. In other embodiments, it may be desirable to use enantiomerically pure compounds. In additional embodiments, it may be desirable to use diastereomerically pure compounds. In some embodiments, it may be desirable to use mixtures of compounds having enantiomeric excesses and/or diastereomeric excesses of about 5%, 10%, 15%, 20%, 25%, 30%, 35%, 40%, 45%, 50%, 65%, 60%, 65%, 70%, 75%, 80%, 85%, 90%, 95%, or 100%. In other embodiments, the enantiomeric excesses and/or diastereomeric excesses is at least 5%, 10%, 15%, 20%, 25%, 30%, 35%, 40%, 45%, 50%, 65%, 60%, 65%, 70%, 75%, 80%, 85%, 90%, 95%, or 100%. In some embodiments, it may be preferable to utilize stereochemically pure enantiomers and/or diastereomers of embodiments—such as when contact with chiral molecules is being targeted for attenuating oxidative damage. However, in many circumstances, non-chiral molecules are being targeted for attenuating oxidative damage. In such circumstances, embodiments may be utilized without concern for their stereochemical purity. Moreover, in some embodiments, mixtures of enantiomers and diastereomers may be used even when the compounds are targeting chiral molecules for attenuating oxidative damage.

In some aspects, isotopically modified PUFAs impart an amount of heavy atoms in a particular tissue. Thus, in some aspects, the amount of heavy molecules will be a particular percentage of the same type of molecules in a tissue. For example, the number of heavy molecules may be about 1%-100% of the total amount of the same type of molecules. In some aspects, 10-50% the molecules are substituted with the same type of heavy molecules.

In some embodiments, a compound with the same chemical bonding structure as an essential PUFA but with a different isotopic composition at particular positions will have significantly and usefully different chemical properties from the unsubstituted compound. The particular positions with respect to oxidation, including oxidation by ROS, comprise bis-allylic positions of essential polyunsaturated fatty acids and their derivatives, as shown in FIG. 1. The essential PUFAs isotopically reinforced at bis-allylic positions shown below will be more stable to the oxidation. Accordingly, some aspects of the invention provide for particular methods of using compounds of Formula (1) or salts thereof, whereas the sites can be further reinforced with carbon-13. $R^1$=alkyl, H, or cation; m=1-10; n=1-5, where at each bis-allylic position, one or both Y atoms are deuterium atoms, for example,

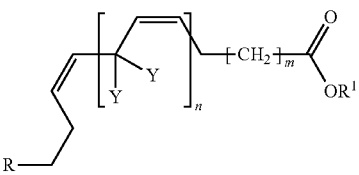

(1)

R = H, C$_3$H$_7$; R$^1$ = H, alkyl, or cation; Y = H or D 11,11-Dideutero-cis,cis-9,12-Octadecadienoic acid (11,11-Dideutero-(9Z,12Z)-9,12-Octadecadienoic acid; D2-LA); and 11,11,14,14-Tetradeutero-cis,cis,cis-9,12,15-Octadecatrienoic acid (11,11,14,14-Tetradeutero-(9Z,12Z,15Z)-9,12,15-Octadecatrienoic acid; D4-ALA). In some embodiments, said positions, in addition to deuteration, can be further reinforced by carbon-13, each at levels of isotope abundance above the naturally-occurring abundance level. All other carbon-hydrogen bonds in the PUFA molecule may optionally contain deuterium and/or carbon-13 at or above the natural abundance level.

Essential PUFAs are biochemically converted into higher homologues by desaturation and elongation. Therefore, some sites which are not bis-allylic in the precursor PUFAs will become bis-allylic upon biochemical transformation. Such sites then become sensitive to oxidation, including oxidation by ROS. In a further embodiment, such pro-bis-allylic sites, in addition to existing bis-allylic sites are reinforced by isotope substitution as shown below. Accordingly, this aspect of the invention provides for the use of compounds of Formula (2) or salt thereof, where at each bis-allylic position, and at each pro-bis-allylic position, one or more of X or Y atoms may be deuterium atoms. R1=alkyl, cation, or H; m=1-10; n=1-5; p=1-10.

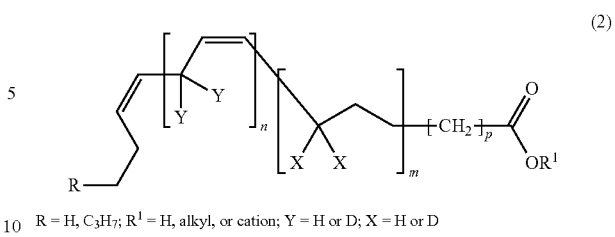

(2)

R = H, C$_3$H$_7$; R$^1$ = H, alkyl, or cation; Y = H or D; X = H or D

Said positions, in addition to deuteration, can be further reinforced by carbon-13, each at levels of isotope abundance above the naturally-occurring abundance level. All other carbon-hydrogen bonds in the PUFA molecule may contain optionally deuterium and/or carbon-13 at or above the natural abundance level.

Oxidation of PUFAs at different bis-allylic sites gives rise to different sets of oxidation products. For example, 4-HNE is formed from n-6 PUFAs whereas 4-HHE is formed from n-3 PUFAs (Negre-Salvayre A, et al. *Brit. J. Pharmacol.* 2008; 153:6-20). The products of such oxidation possess different regulatory, toxic, signaling, etc. properties. It is therefore desirable to control the relative extent of such oxidations. Accordingly, some aspects of the invention provide for the use of compounds of Formula (3), or salt thereof, differentially reinforced with heavy stable isotopes at selected bis-allylic or pro-bis-allylic positions, to control the relative yield of oxidation at different sites, as shown below, such that any of the pairs of $Y^1$-$Y^n$ and/or $X^1$-$X^m$ at the bis-allylic or pro-bis-allylic positions of PUFAs may contain deuterium atoms. R1=alkyl, cation, or H; m=1-10; n=1-6; p=1-10

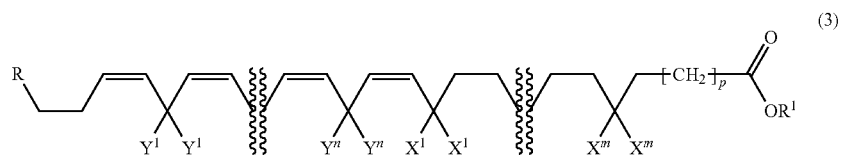

(3)

R = H, C$_3$H$_7$; R$^1$ = H, alkyl, or cation; Y = H or D; X = H or D

Said positions, in addition to deuteration, can be further reinforced by carbon-13. All other carbon-hydrogen bonds in the PUFA molecule may contain deuterium at, or above the natural abundance level. It will be appreciated that the break lines in the structure shown above represents a PUFA with a varying number of double bonds, a varying number of total carbons, and a varying combination of isotope reinforced bis-allylic and pro-bis-allylic sites.

Exact structures of compounds illustrated above are shown below that provide for both isotope reinforced n-3 (omega-3) and n-6 (omega-6) essential polyunsaturated fatty acids, and the PUFAs made from them biochemically by desaturation/elongation. Any one of these compounds may be used to slow oxidation. In the following compounds, the PUFAs are isotopically reinforced at oxidation sensitive sites and/or sites that may become oxidation sensitive upon biochemical desaturation/elongation. $R^1$ may be H, alkyl, or cation; $R^2$ may be H or D; * represents either $^{12}$C or $^{13}$C.

D-Linoleic acids include:

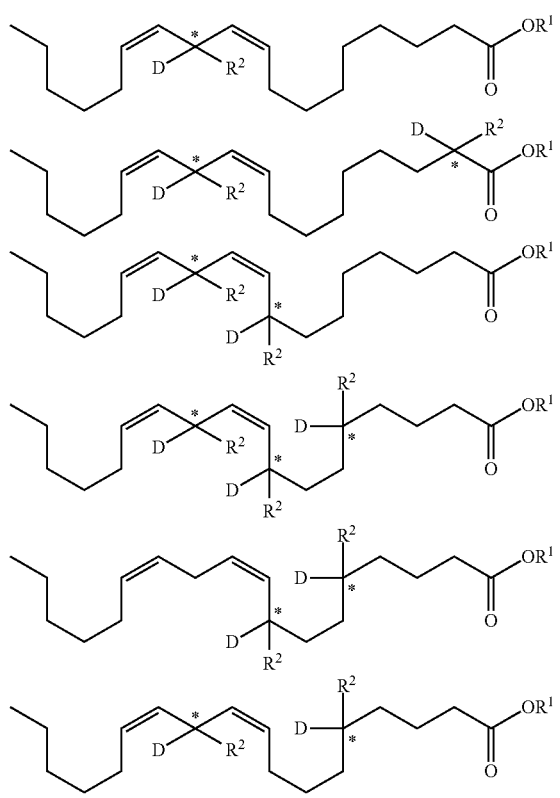

The per-deuterated linoleic acid below may be produced by microbiological methods, for example by growing in media containing deuterium and/or carbon-13.

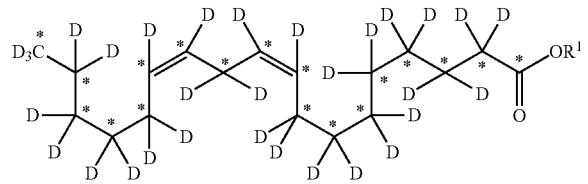

D-Arachidonic Acids Include:

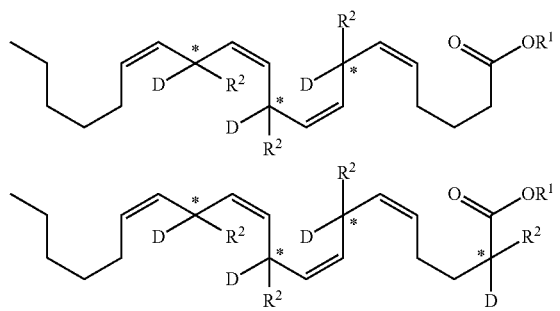

The per-deuterated arachidonic acid below may be produced by microbiological methods, such as by growing in media containing deuterium and/or carbon-13.

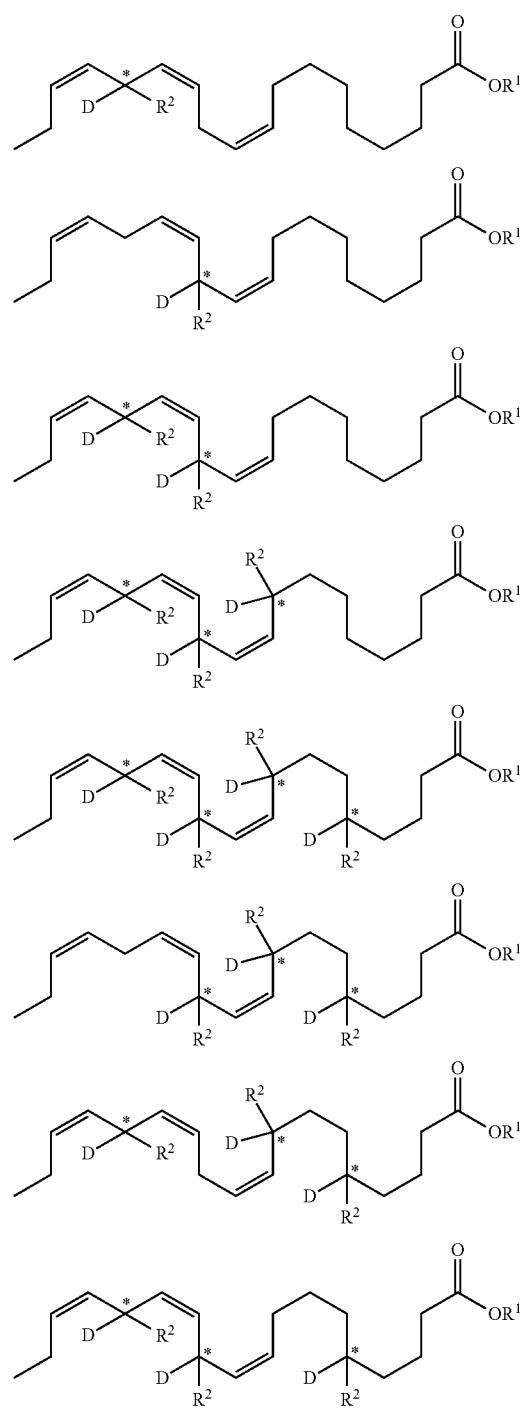

D-Linolenic acids include:

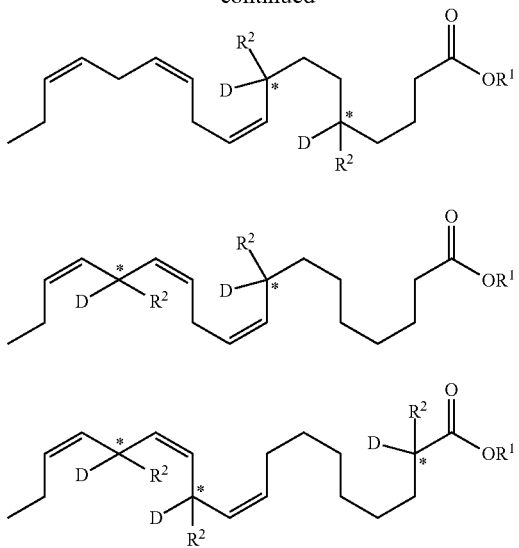

Per-deuterated linolenic acid below may be produced by microbiological methods, such as growing in media containing deuterium and/or carbon-13.

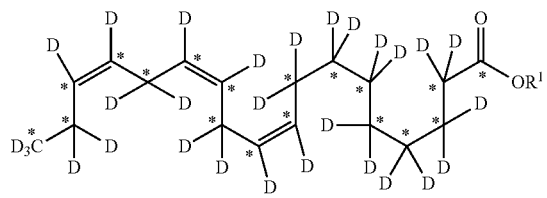

In some aspects of the invention, any PUFAs, whether essential or not, that are capable of being taken up from diet and used in the body, can be utilized. In the case of essential or non-essential PUFAs or precursors, the supplemented stabilized materials can compete with other dietary uptake and bio-manufacture to reduce the available disease-causing species concentrations.

In some aspects of the invention, the PUFAs isotopically reinforced at oxidation sensitive positions as described by way of the structures above are heavy isotope enriched at said positions as compared to the natural abundance of the appropriate isotope, deuterium and/or carbon-13.

In some embodiments, the disclosed compounds are enriched to 99% isotope purity or more. In some embodiments, the heavy isotope enrichment at said positions is between 50%-99% deuterium and/or carbon-13.

In some embodiments, the modified fatty acids, when dosed via diet as drugs or supplements, may be dosed as pro-drugs, including, but not limited to, non-toxic and pharmaceutically suitable esters of the parent fatty acid or mimetic, such as an ethyl ester or glyceryl ester. This ester assists in tolerance of the drug in the gut, assists in digestion, and relies on the high levels of esterases in the intestines to de-esterify the ester pro-drugs into the active acid form of the drug which adsorbs. Hence, in some embodiments, the invention encompasses the pro-drug esters of the modified fatty acids herein. Examples of this type of drug in the market, nutrition, and clinical trials literature, including Glaxo's Lovaza, (mixtures of omega 3 fatty acid esters, EPA, DHA, and alpha-linolenic acid), Abbott's Omacor (omega-3-fatty acid esters), and most fish oil supplements (DHA and EPA esters). In some aspects, incorporation of the ester pro-drugs into tissues or cells refers to the incorporation of the modified parent PUFA as it would be used as a bodily constituent.

In some embodiments, stabilized compositions mimic natural occurring fatty acids without changing their elemental composition. For example, the substituent may retain the chemical valence shell. Some embodiments include naturally occurring fatty acids, mimetics, and their ester pro-drugs, that are modified chemically to be effective at preventing specific disease mechanisms, but are modified in a way (such as isotopic substitution) that does not change the elemental composition of the material. For example, deuterium is a form of the same element hydrogen. In some aspects, these compounds maintain elemental composition and are stabilized against oxidation. Some compounds that are stabilized against oxidation are stabilized at oxidation sensitive loci. Some compounds are stabilized against oxidation via heavy isotope substitution, then at bis-allylic carbon hydrogen bonds, etc.

In a further embodiment, oxidation-prone bis-allylic sites of PUFAs can be protected against hydrogen abstraction by moving bis-allylic hydrogen-activating double bonds further apart, thus eliminating the bis-allylic positions while retaining certain PUFA fluidity as shown below. These PUFA mimetics have no bis-allylic positions.

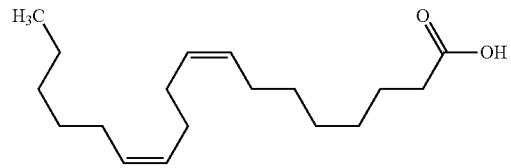

Octadeca-8,12-dienoic acid

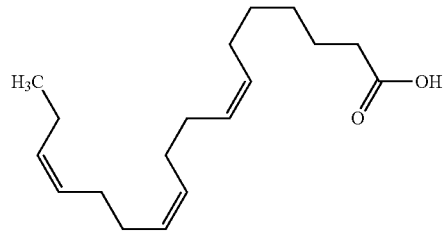

Octadeca-7,11,15-trienoic acid

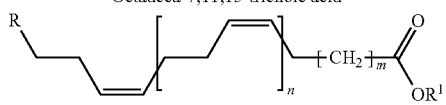

R = H, C$_3$H$_7$; R$^1$ = H; alkyl; n = 1-4; m = 1-12

In a further embodiment, oxidation-prone bis-allylic sites of PUFAs can be protected against hydrogen abstraction by using heteroatoms with valence II, thus eliminating the bis-allylic hydrogens as shown below. These PUFA mimetics also have no bis-allylic hydrogens.

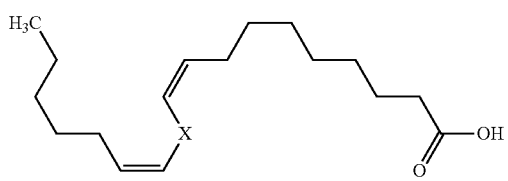

X = S: 10-Hept-1-enylsulfanyl-dec-9-enoic acid
X = O: 10-Hept-1-enyloxy-dec-9-enoic acid

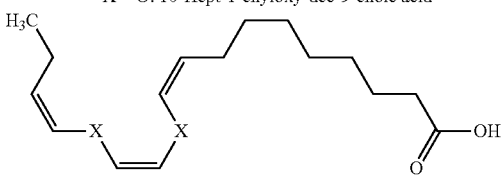

X = S: 10-(2-But-1-enylsulfanyl-vinylsulfanyl)-dec-9-enoic acid
X = O: 10-(2-But-1-enyloxy-vinyloxy)-dec-9-enoic acid

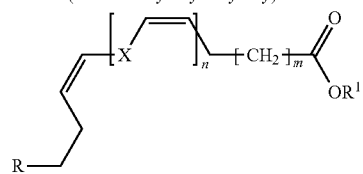

R = H, C$_3$H$_7$; R$^1$ = H; alkyl; X = O;
S; n = 1-5; m = 1-12

In a further embodiment, PUFA mimetics, i.e. compounds structurally similar to natural PUFAs but unable to get oxidized because of the structural differences, can be employed for the above mentioned purposes. Oxidation-prone bis-allylic sites of PUFAs can be protected against hydrogen abstraction by di-methylation or halogenation as shown below. The hydrogen atoms on the methyl groups may optionally be halogens, such as fluorine, or deuterium. These PUFA mimetics are dimethylated at bis-allylic sites.

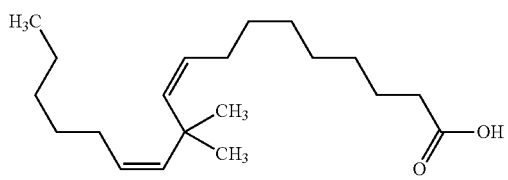

11,11-Dimethyl-octadeca-9,12-dienoic acid

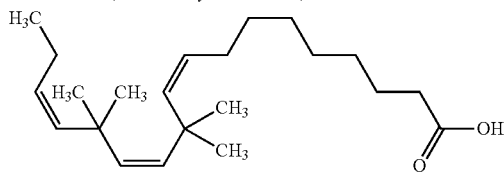

11,11,14,14-Tetramethyl-octadeca-9,12,15-trienoic acid

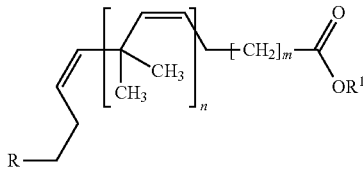

R = H, C$_3$H$_7$; R$^1$ = H; alkyl;
n = 1-5; m = 1-12

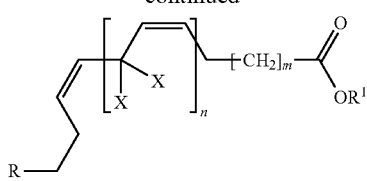

R = H, C$_3$H$_7$; R$^1$ = H; alkyl;
n = 1-5; m = 1-12;
X = F, Cl., Br, or I

In a further embodiment, oxidation-prone bis-allylic sites of PUFAs can be protected against hydrogen abstraction by alkylation as shown below. These PUFA mimetics are dialkylated at bis-allylic sites.

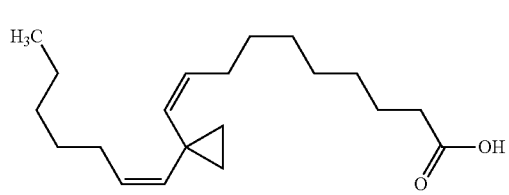

10-(1-Hept-1-enyl-cyclopropyl)-dec-9-enoic acid

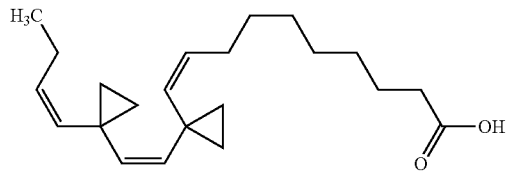

10-{1-[2-(1-But-1-enyl-cyclopropyl)-vinyl]-cyclopropyl}-dec-9-enoic acid

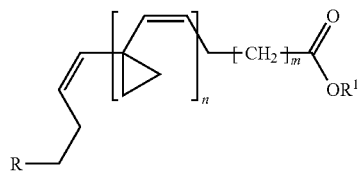

R = H, C$_3$H$_7$; R$^1$ = H; alkyl;
n = 1-5; m = 1-12

In a further embodiment, cyclopropyl groups can be used instead of double bonds, thus rendering the acids certain fluidity while eliminating the bis-allylic sites as shown below. These PUFA mimetics have cyclopropyl groups instead of double bonds.

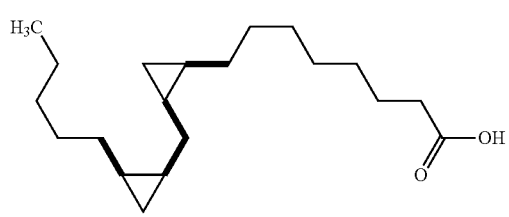

8-[2-(2-Pentyl-cyclopropylmethyl)-cyclopropyl]-octanoic acid

-continued

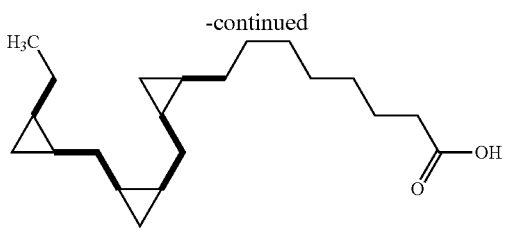

8-{2-[2-(2-Ethyl-cyclopropylmethyl)-cyclopropylmethyl]-cyclopropyl}-octanoic acid

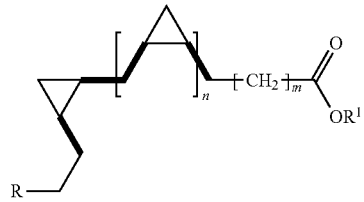

R = H, C$_3$H$_7$; R$^1$ = H; alkyl;
n = 1-5; m = 1-12

In a further embodiment, 1,2-substituted cyclobutyl groups in appropriate conformation can be used instead of double bonds, thus rendering the acids certain fluidity while eliminating the bis-allylic sites as shown below. These PUFA mimetics have 1,2-cyclobutyl groups instead of double bonds.

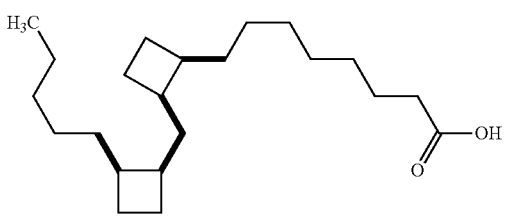

8-[2-(2-Pentyl-cyclobutylmethyl)-cyclobutyl]-octanoic acid

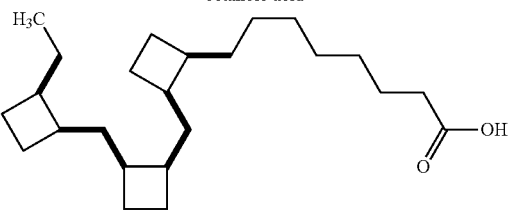

8-{2-[2-(2-Ethyl-cyclobutylmethyl)-cyclobutylmethyl]-cyclobutyl}-octanoic acid

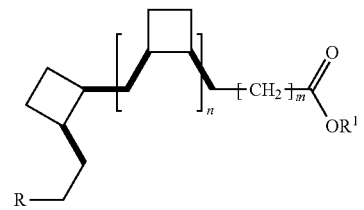

R = H, C$_3$H$_7$; R$^1$ = H; alkyl;
n = 1-5; m = 1-12

In a modification of the previous embodiment of mimetics with 1,2-cyclobutyl groups instead of double bonds, 1,3-substituted cyclobutyl groups in appropriate conformation can be used instead of double bonds, thus rendering the acids certain fluidity while eliminating the bis-allylic sites. The following PUFA mimetics have 1,3-cyclobutyl groups instead of double bonds.

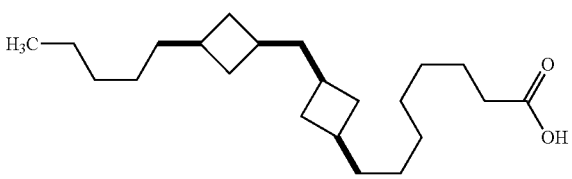

8-[3-(3-Pentyl-cyclobutylmethyl)-cyclobutyl]-octanoic acid

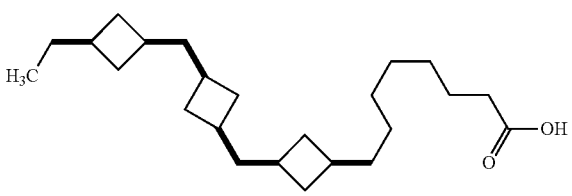

8-{3-[3-(3-Ethyl-cyclobutylmethyl)-cyclobutylmethyl]-cyclobutyl}-octanoic acid

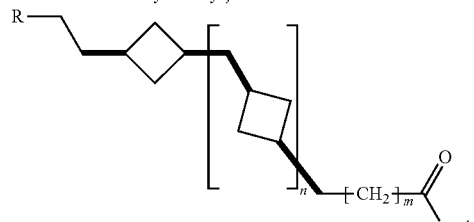

R = H, C$_3$H$_7$; R$^1$ = H; alkyl; n = 1-5; m = 1-12

It is a well known principle in medicinal chemistry that certain functional groups are isosteric and/or bioisosteric with certain other functional groups. Bioisosteres are substituents or groups with similar physical or chemical properties which produce broadly similar biological properties to a chemical compound. For example, well known isosteres and/or bioisosteres for hydrogen include halogens such as fluorine; isosteres and/or bioisosteres of alkenes include alkynes, phenyl rings, cyclopropyl rings, cyclobutyl rings, cyclopentyl rings, cyclohexyl rings, thioethers, and the like; isosteres and/or bioisosteres of carbonyls include sulfoxides, sulfones, thiocarbonyls, and the like; isosteres and/or bioisosteres of esters include amides, sulfonic acid esters, sulfonamides, sulfinyl acid esters, sulfinylamindes, and the like. Consequently, PUFA mimetics also include compounds having isosteric and/or bioisosteric functional groups.

It is contemplated that it may be useful to formulate PUFAs and/or PUFA mimetics as a pro-drug for use in the invention. A pro-drug is a pharmacological substance may itself have biological activity, but upon administration the pro-drug is metabolized into a form that also exerts biological activity. Many different types of pro-drugs are known and they can be classified into two major types based upon their cellular sites of metabolism. Type I pro-drugs are those that are metabolized intracellularly, while Type II are those that are metabolized extracellularly. It is well-known that carboxylic acids may be converted to esters and various other functional groups to enhance pharmacokinetics such as absorption, distribution, metabolism, and excretion. Esters are a well-known pro-drug form of carboxylic acids formed by the condensation of an alcohol (or its chemical equivalent) with a carboxylic acid (or its chemical equivalent). In some embodiments, alcohols (or their chemical equivalent) for incorporation into pro-drugs of PUFAs include pharmaceutically acceptable alcohols or chemicals that upon metabolism yield pharmaceutically acceptable alcohols. Such alcohols include, but are not limited to, propylene glycol, ethanol, isopropanol, 2-(2-ethoxyethoxy)ethanol (Transcutol®, Gattefosse, Westwood, N.J. 07675), benzyl alcohol, glycerol, polyethylene glycol 200, polyethylene glycol 300, or polyethylene glycol 400; polyoxyethylene castor oil derivatives (for example, polyoxyethyleneglyceroltriricinoleate or polyoxyl 35 castor oil (Cremophor®EL, BASF Corp.), polyoxyethyleneglycerol oxystearate (Cremophor®RH 40 (polyethyleneglycol 40 hydrogenated castor oil) or Cremophor®RH 60 (polyethyleneglycol 60 hydrogenated castor oil), BASF Corp.)); saturated polyglycolized glycerides (for example, Gelucire® 35/10, Gelucire® 44/14, Gelucire® 46/07, Gelucire® 50/13 or Gelucire® 53/10, available from Gattefosse, Westwood, N.J. 07675); polyoxyethylene alkyl ethers (for example, cetomacrogol 1000); polyoxyethylene stearates (for example, PEG-6 stearate, PEG-8 stearate, polyoxyl 40 stearate NF, polyoxyethyl 50 stearate NF, PEG-12 stearate, PEG-20 stearate, PEG-100 stearate, PEG-12 distearate, PEG-32 distearate, or PEG-150 distearate); ethyl oleate, isopropyl palmitate, isopropyl myristate; dimethyl isosorbide; N-methylpyrrolidinone; parafin; cholesterol; lecithin; suppository bases; pharmaceutically acceptable waxes (for example, carnauba wax, yellow wax, white wax, microcrystalline wax, or emulsifying wax); pharmaceutically acceptable silicon fluids; soribitan fatty acid esters (including sorbitan laurate, sorbitan oleate, sorbitan palmitate, or sorbitan stearate); pharmaceutically acceptable saturated fats or pharmaceutically acceptable saturated oils (for example, hydrogenated castor oil (glyceryl-tris-12-hydroxystearate), cetyl esters wax (a mixture of primarily C14-C18 saturated esters of C14-C18 saturated fatty acids having a melting range of about 43°-47° C.), or glyceryl monostearate).

In some embodiments, the fatty acid pro-drug is represented by the ester P—B, wherein the radical P is a PUFA and the radical B is a biologically acceptable molecule. Thus, cleavage of the ester P—B affords a PUFA and a biologically acceptable molecule. Such cleavage may be induced by acids, bases, oxidizing agents, and/or reducing agents. Examples of biologically acceptable molecules include, but are not limited to, nutritional materials, peptides, amino acids, proteins, carbohydrates (including monosaccharides, disaccharides, polysaccharides, glycosaminoglycans, and oligosaccharides), nucleotides, nucleosides, lipids (including mono-, di- and tri-substituted glycerols, glycerophospholipids, sphingolipids, and steroids).

In some embodiments, alcohols (or their chemical equivalent) for incorporation into pro-drugs of PUFAs include alcohols with 1 to 50 carbon atoms ("$C_{1-50}$ alcohols"), $C_{1-45}$ alcohols, $C_{1-40}$ alcohols, $C_{1-35}$ alcohols, $C_{1-30}$ alcohols, $C_{1-25}$ alcohols, $C_{1-20}$ alcohols, $C_{1-15}$ alcohols, $C_{1-10}$ alcohols, $C_{1-6}$ alcohols (whenever it appears herein, a numerical range such as "1-50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). Such alcohols may be branched, unbranched, saturated, unsaturated, polyunsaturated and/or include one or more heteroatoms such as nitrogen, oxygen, sulfur, phosphorus, boron, silicone, fluorine, chlorine, bromine, or iodine. Exemplary alcohols include methyl, ethyl, propyl, iso-propyl, n-butyl, isobutyl, sec-butyl, tert-butyl, pentyl, hexyl, perfluoromethyl, perchloromethyl, perfluoro-tert-butyl, perchloro-tert-butyl, and benzyl alcohols as well as ether alcohols such as polyethylene glycols. In some embodiments, the alcohol contains a charged species. Such species may be anionic or cationic. In some embodiments, the species is a positively charged phosphorus atom. In other embodiments, the positively charged phosphorus atom is a phosphonium cation. In other embodiments the charged species is a primary, secondary, tertiary, or quaternary ammonium cation.

In some embodiments, alcohols (or their chemical equivalent) for incorporation into pro-drugs of PUFAs include polyalcohols such as diols, triols, tetra-ols, penta-ols, etc. Examples of polyalcohols include ethylene glycol, propylene glycol, 1,3-butylene glycol, polyethylene glycol, methylpropanediol, ethoxydiglycol, hexylene glycol, dipropylene glycol glycerol, and carbohydrates. Esters formed from polyalcohols and PUFAs may be mono-esters, di-esters, tri-esters, etc. In some embodiments, multiply esterified polyalcohols are esterified with the same PUFAs. In other embodiments, multiply esterified polyalcohols are esterified with different PUFAs. In some embodiments, the different PUFAs are stabilized in the same manner. In other embodiments, the different PUFAs are stabilized in different manners (such as deuterium substitution in one PUFA and $^{13}C$ substitution in another PUFA). In some embodiments, one or more PUFAs is an omega-3 fatty acid and one or more PUFAs is an omega-6 fatty acid.

It is also contemplated that it may be useful to formulate PUFAs and/or PUFA mimetics and/or PUFA pro-drugs as salts for use in the invention. For example, the use of salt formation as a means of tailoring the properties of pharmaceutical compounds is well known. See Stahl et al., Handbook of pharmaceutical salts: Properties, selection and use (2002) Weinheim/Zurich: Wiley-VCH/VHCA; Gould, Salt selection for basic drugs, Int. J. Pharm. (1986), 33:201-217. Salt formation can be used to increase or decrease solubility, to improve stability or toxicity, and to reduce hygroscopicity of a drug product.

Formulation of PUFAs and/or PUFA mimetics and/or PUFA pro-drugs as salts includes, but is not limited to, the use of basic inorganic salt forming agents, basic organic salt forming agents, and salt forming agents containing both acidic and basic functional groups. Various useful inorganic bases for forming salts include, but are not limited to, alkali metal salts such as salts of lithium, sodium, potassium rubidium, cesium, and francium, and alkaline earth metal salts such as berylium, magnesium, calcium, strontium, barium, and radium, and metals such as aluminum. These inorganic bases may further include counterions such as carbonates, hydrogen carbonates, sulfates, hydrogen sulfates, sulfites, hydrogen sulfites, phosphates, hydrogen phosphates, dihydrogen phosphates, phosphites, hydrogen phosphites, hydroxides, oxides, sulfides, alkoxides such as methoxide, ethoxide, and t-butoxide, and the like. Various useful organic bases for forming salts include, but are not limited to, amino acids, basic amino acids such as arginine, lysine, ornithine and the like, ammonia, alkylamines such as methylamine, ethylamine, dimethylamine, diethylamine, trimethylamine, triethylamine and the like, heterocyclic amines such as pyridine, picoline and the like, alkanolamines such as ethanolamine, diethanolamine, triethanolamine and the like, diethylaminoethanol, dimethylaminoethanol, N-methylglucamine, dicyclohexylamine, N,N'-dibenzylethylenediamine, ethylenediamine, piperazine, choline, trolamine, imidazole, diolamine, betaine, tromethamine, meglumine, chloroprocain, procaine, and the like.

Salt formulations of PUFAs and/or PUFA mimetics and/or PUFA pro-drugs include, but are not limited to, pharmaceutically acceptable basic inorganic salts, basic organic salts, and/or organic compounds having both acidic and basic functional groups. Pharmaceutically acceptable salts are well known in the art and include many of the above-recited inorganic and organic bases. Pharmaceutically acceptable salts further include salts and salt-forming agents found in drugs approved by the Food and Drug Administration and foreign regulatory agencies. Pharmaceutically acceptable organic cations for incorporation include, but are not limited to, benzathine, chloroprocaine, choline, diethanolamine, ethylenediamine, meglumine, procaine, benethamine, clemizole, diethylamine, piperazine, and tromethamine. Pharmaceutically acceptable metallic cations for incorporation include, but are not limited to, aluminum, calcium, lithium, magnesium, potassium, sodium, zinc, barium, and bismuth. Additional salt-forming agents include, but are not limited to, arginine, betaine, carnitine, diethylamine, L-glutamine, 2-(4-imidazolyl)ethylamine, isobutanolamine, lysine, N-methylpiperazine, morpholine, and theobromine.

Moreover, several lists of pharmaceutically approved counterions exists. See Bighley et al., Salt forms of drugs and absorption. 1996 In: Swarbrick J. et al. eds. Encyclopaedia of pharmaceutical technology, Vol. 13 New York: Marcel Dekker, Inc. pp 453-499; Gould, P. L., Int. J. Pharm. 1986, 33, 201-217; Berge, J. Pharm. Sci. 1977, 66, 1-19; Heinrich Stahl P., Wermuch C. G. (editors), Handbook of Pharmaceutical Salts, IUPAC, 2002; Stahl et al., Handbook of pharmaceutical salts: Properties, selection and use (2002) Weinheim/Zurich: Wiley-VCH/VHCA, all of which are incorporated herein by reference.

It may be unnecessary to substitute all isotopically unmodified PUFAs, such as non-deuterated PUFAs, with isotopically modified PUFAs such as deuterated PUFAs. In some embodiments, is preferable to have sufficient isotopically modified PUFAs such as D-PUFAs in the membrane to prevent unmodified PUFAs such as H-PUFAs from sustaining a chain reaction of self-oxidation. During self-oxidation, when one PUFA oxidizes, and there is a non-oxidized PUFA in the vicinity, the non-oxidized PUFA can get oxidized by the oxidized PUFA. This may also be referred to as autooxidation. In some instances, if there is a low concentration, for example "dilute" H-PUFAs in the membrane with D-PUFAs, this oxidation cycle may be broken due to the distance separating H-PUFAs. In some embodiments, the concentration of isotopically modified PUFAs is present in a sufficient amount to maintain autooxidation chain reaction. To break the autooxidation chain reaction, for example, 1-60%, 5-50%, or 15-35% of the total molecules of the same type are in the membrane. This may be measured by IRMS (isotope ratio mass spectrometry).

A further aspect of the invention provides a dietary, supplementary or pharmaceutical composition of the active compounds. In some embodiments, the dietary, supplementary, or pharmaceutical composition may comprise a salt of the active compound.

Various useful inorganic bases for forming salts include, but are not limited to, alkali metal salts such as salts of lithium, sodium, potassium rubidium, cesium, and francium, and alkaline earth metal salts such as berylium, magnesium, calcium, strontium, barium, and radium, and metals such as aluminum. These inorganic bases may further include counterions such as carbonates, hydrogen carbonates, sulfates, hydrogen sulfates, sulfites, hydrogen sulfites, phosphates, hydrogen phosphates, dihydrogen phosphates, phosphites, hydrogen phosphites, hydroxides, oxides, sulfides, alkoxides such as methoxide, ethoxide, and t-butoxide, and the like.

Various useful organic bases for forming salts include, but are not limited to, amino acids; basic amino acids such as arginine, lysine, ornithine and the like; ammonia; ammonium hydroxide; alkylamines such as methylamine, ethylamine, dimethylamine, diethylamine, trimethylamine, triethylamine and the like; heterocyclic amines such as pyridine, picoline and the like; alkanolamines such as ethanolamine, diethanolamine, triethanolamine and the like, diethylaminoethanol, dimethylaminoethanol; N-methylglucamine; dicyclohexylamine; N,N'-dibenzylethylenediamine; ethylenediamine; piperazine; choline; trolamine; imidazole; diolamine; betaine; tromethamine; meglumine; chloroprocain; procaine; and the like.

Salts of active compounds may include, but are not limited to, pharmaceutically acceptable salts. Pharmaceutically acceptable salts are well known in the art and include many of the above-listed salt-forming agents. Pharmaceutically acceptable salts further include salts and salt-forming agents of the type present in drugs approved by the Food and Drug Administration and foreign regulatory agencies.

Pharmaceutically acceptable organic cations for incorporation into a salt of an active compound include, but are not limited to, benzathine, chloroprocaine, choline, diethanolamine, ethylenediamine, meglumine, procaine, benethamine, clemizole, diethylamine, piperazine, and tromethamine.

Pharmaceutically acceptable metallic cations for incorporation into a salt of an active compound include, but are not limited to, aluminum, calcium, lithium, magnesium, potassium, sodium, zinc, barium, and bismuth.

Additional salt-forming agents having potential usefulness as forming salts include, but are not limited to, acetylaminoacetic acid, N-acetyl-L-asparagine, N-acetylcystine, arginine, betaine, carnitine, L-glutamine, 2-(4-imidazolyl)ethylamine, isobutanolamine, lysine, N-methylpiperazine, and morpholine.

Moreover, several lists of pharmaceutically approved counterions exists. See Bighley et al., Salt forms of drugs and absorption. 1996 In: Swarbrick J. et al. eds. Encyclopaedia of pharmaceutical technology, Vol. 13 New York: Marcel Dekker, Inc. pp 453-499; Gould, P. L., Int. J. Pharm. 1986, 33, 201-217; Berge, J. Pharm. Sci. 1977, 66, 1-19; Heinrich Stahl P., Wermuch C. G. (editors), Handbook of Pharmaceutical Salts, IUPAC, 2002; Stahl et al., Handbook of pharmaceutical salts: Properties, selection and use (2002) Weinheim/Zurich: Wiley-VCH/VHCA, all of which are incorporated herein by reference.

Co-Administration

In some embodiments, the compounds disclosed herein are administered in combination. For example, in some embodiments, two, three, four, and/or five or more stabilized compounds are administered together. In some embodiments, stabilized compounds are administered in approximately similar amounts. In other embodiments, stabilized compounds are administered in differing amounts. For example, any one of two or more compounds in a mixture may represent about 1% to about 99% of a mixture, about 5% to about 95% of a mixture, about 10% to about 90% of a mixture, about 15% to about 85% of a mixture, about 20% to about 80% of a mixture, about 25% to about 75% of a mixture, about 30% to about 70% of a mixture, about 35% to about 65% of a mixture, about 40% to about 60% of a mixture, about 40% to about 60% of a mixture, about 45% to about 55% of a mixture, and/or about 50% of a mixture. In other embodiments, any one of two or more compounds in a mixture may represent about: 5%, 10%, 15%, 20%, 25%, 30%, 35%, 40%, 45%, 50%, 65%, 60%, 65%, 70%, 75%, 80%, 85%, 90%, 95%, or 100% of a mixture.

Although antioxidants cannot cancel the negative effects of PUFA peroxidation due to the stochastic nature of the process and the stability of PUFA peroxidation products (reactive carbonyls) to antioxidant treatment, co-administration of antioxidants with compositions resistant to oxidation, such as those described herein, may prove beneficial for treating oxidative stress-related disorders.

Certain antioxidants contemplated as useful for co-administration include the following: vitamins, such as vitamin C and vitamin E; glutathione, lipoic acid, uric acid, carotenes, lycopene, lutein, anthocyanins, oxalic acid, phytic acid, tannins, coenzyme Q, melatonin, tocopherols, tocotrienols, polyphenols including resveratrol, flavonoids, selenium, eugenol, idebenone, mitoquinone, mitoquinol, ubiquinone, Szeto-Schiller peptides, and mitochondrial-targeted antioxidants. When not explicitly mentioned, quinone derivatives of the aforementioned antioxidants are also contemplated as useful for co-administration.

In some embodiments, stabilized compounds are administered with compounds that upregulate antioxidant genes. In other embodiments, stabilized compounds are administered with compounds that affect signaling pathways, such as the Keap1/Nrf2/ARE signaling pathway, thereby resulting in the production of anti-inflammatory and/or antioxidant proteins, such as heme oxygenase-1 (HO-1). In some embodiments, stabilized compounds are administered with antioxidant inflammation modulators. Antioxidant inflammation modulators suppress pro-oxidant and/or pro-inflammatory transcription factors. In some embodiments, antioxidant inflammation modulators are activators of the transcription factor Nrf2. Nrf2 activation promotes the antioxidant, detoxification, and anti-inflammatory genes upregulation. In other embodiments, antioxidant inflammation modulators suppress NF-κB. In some embodiments, antioxidant inflammation modulators suppress STAT3. In other embodiments, stabilized compounds are administered with compounds that affect histone deacetylase activity. In some embodiments, stabilized compounds are administered with compounds that bind to antioxidant response elements (ARE). In other embodiments, stabilized compounds are administered with bardoxolone methyl (2-cyano-3,12-dioxooleane-1,9(11)-dien-28-oic acid methyl ester) as the antioxidant inflammation modulator. In some embodiments, the antioxidant inflammation modulator is 2-cyano-3,12-dioxooleane-1,9(11)-dien-28-oic acid, or a pharmaceutically acceptable ester thereof. In other embodiments, the antioxidant inflammation modulator is an amide of 2-cyano-3,12-dioxooleane-1,9(11)-dien-28-oic acid. In some embodiments, the antioxidant inflammation modulator is a triterpenoid. In other embodiments, the antioxidant inflammation modulator is selected from the following compounds:

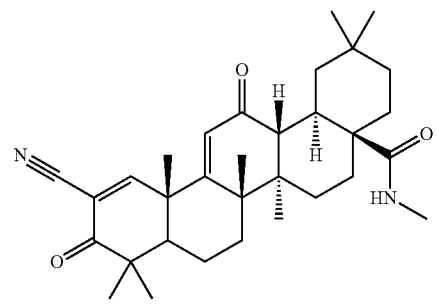

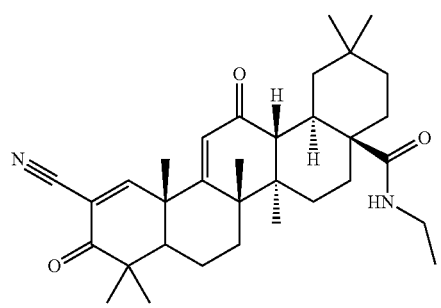

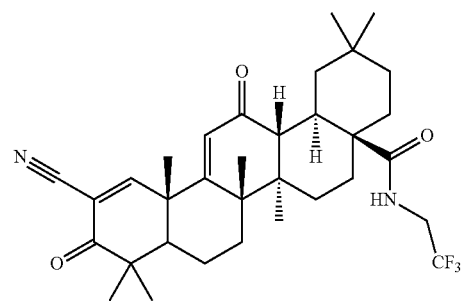

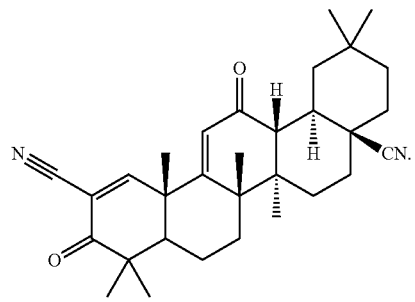

Additional antioxidants believed to be useful in co-administration therapies include those compounds disclosed in U.S. Pat. Nos. 6,331,532; 7,179,928; 7,232,809; 7,888,334; 7,888,335; 7,432,305; 7,470,798; and 7,514,461; and U.S. Patent Application Nos. 20020052342; 20030069208; 20040106579; 20050043553; 20050245487; 20060229278; 20070238709; 20070270381; 20080161267; 20080275005; 20090258841; 20100029706; and 20110046219; in which the compounds disclosed therein are incorporated by reference. These compounds are mitochondrially-targeted compounds and include, but are not limited to:

Compounds of Formulas I or II

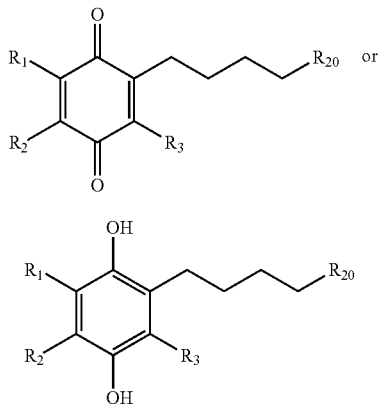

Formula I

Formula II wherein $R_1$ and $R_2$ are independently selected from —$C_1$-$C_4$ alkyl, —$C_1$-$C_4$ haloalkyl, —CN, —F, —Cl, —Br, and —I; $R_3$ is selected from —$C_1$-$C_4$ alkyl, —$C_1$-$C_4$ haloakyl, —CN, —F, —Cl, and —I, and $R_{20}$ is independently selected from —$C_1$-$C_{20}$ alkyl, —$C_1$-$C_{20}$ alkenyl, —$C_1$-$C_{20}$ alkynyl, and —$C_1$-$C_{20}$ containing at least one double bond and at least one triple bond.

Compounds such as: 3-(6-Hydroxy-2-methyl-3,4,7,8,9,10-hexahydro-7,10-methano-2H-benzo[h]chromen-2-yl)-propionic acid methyl ester; 3-(6-Hydroxy-2-methyl-3,4,7,8,9,10-hexahydro-7,10-methano-2H-benzo[h]chroman-2-yl)-propionic acid; 2,2,-Dimethyl-3,4,7,8,9,10-hexahydro-7,10-methano-2H-benzo[h]chromen-6-ol; 3-(6-Hydroxy-2-methyl-3,4,7,8,9,10-hexahydro-7,10-propano-2H-benzo[h]chromen-2-yl)-propionic acid methyl ester; 2-Methyl-2-[3-(thiazol-2-ylsulfanyl)-propyl]-3,4,7,8,9,10-hexahydro-7,10-methano-2H-benzo[h]chromen-6-ol; [3-(6-Hydroxy-2-methyl-3,4,7,8,9,10-hexahydro-7,10-methano-2H-benzo[h]chromen-2-yl)-propyl]-phosphonic acid dimethyl ester; [3-(6-Hydroxy-2-methyl-3,4,7,8,9,10-methano-2H-benzo[h]chromen-2-yl)-propyl]-phosphonic acid; 3-(6-Hydroxy-2-methyl-3,4,7,8,9,10-hexahydro-7,10-methano-2H-benzo[h]chromen-2-yl)-propionic acid methyl ester; 4-(6-Hydroxy-2-methyl-3,4,7,8,9,10-hexahydro-7,10-methano-2H-benzo[h]chromen-2-yl)-butane-1-sulfonic acid dimethylamide; 2-(3-Hydroxy-propyl)-2-methyl-3,4,7,8,9,10-hexahydro-7,10-methano-2H-benzo[h]chromen-6-ol; 2-(3-Chloro-propyl)-2-methyl-3,4,7,8,9,10-hexahydro-7,10-methano-2H-benzo[h]chromen-6-ol 2,2-Dimethyl-3,4,7,8,9,10-hexahydro-7,10-methano-2H-benzo[h]chromen-6-ol; -(2-Chloro-ethyl)-2-methyl-3,4,7,8,9,10-hexahydro-7,10-methano-2H-benzo[h]chromen-6-ol; 2-Methyl-2-thiazol-2-yl-3,4,7,8,9,10-hexahydro-7,10-methano-2H-benzo[h]chromen-6-ol; 2,2-Dimethyl-3,4,7,8,9,10-hexahydro-7,10-ethano-2H-benzo[h]chromen-6-ol; 3-(6-Hydroxy-2-methyl-3,4,7,8,9,10-hexahydro-7,10-ethano-2H-benzo[h]chromen-2-yl)-propionic acid; 2-(3-Chloro-propyl)-2-methyl-3,4,7,8,9,10-hexahydro-7,10-ethano-2H-benzo[h]chromen-6-ol; 4-(6-Hydroxy-2,2-dimethyl-3,4,7,8,9,10-hexahydro-7,10-methano-2H-benzo[h]chromen-5-ylmethylene)-2-methyl-5-propyl-2,4-dihydro-pyrazol-3-one.

Compounds such as: 2,2,7,8-Tetramethyl-5-phenyl-chroman-6-ol; 4-(6-Hydroxy-2,2,7,8-tetramethyl-chroman-5-yl)-benzoic acid methyl ester; 4-(6-Hydroxy-2,2,7,8-tetramethyl-chroman-5-yl)-benzoic acid; 2,2,7,8-Tetramethyl-5-pyridin-4-yl-chroman-6-ol; 2,2,7,8-Tetramethyl-5-pyridin-3-yl-chroman-6-ol; 5-(4-Methanesulfonyl-phenyl)-2,2,7,8-tetramethyl-chroman-6-ol; 5-(4-Dimethylamino-phenyl)-2,2,7,8-tetramethyl-chroman-6-ol; 5-(4-Chloro-phenyl)-2,2,7,8-tetramethyl-chroman-6-ol; 4-(6-Hydroxy-2,2,7,8-tetramethyl-chroman-5-yl)-benzene sulfonamide; 5-(4-Methoxy-phenyl)-2,2,7,8-tetramethyl-chroman-6-ol; (6-Hydroxy-2,2,7,8-tetramethyl-chroman-5-ylmethyl)-1-hydroxyurea; 2,2,7,8-Tetramethyl-5-(3-nitro-phenyl)-chroman-6-ol; 2,2,7,8-Tetramethyl-5-(4-trifluoromethyl-phenyl)-chroman-6-ol; 5-(4-tert-Butyl-phenyl)-2,2,7,8-tetramethyl-chroman-6-ol; 2,2,7,8-Tetramethyl-5-(3,4,5-trimethoxy-phenyl)-chroman-6-ol; 4-(6-Hydroxy-2,2,7,8-tetramethyl-chroman-5-yl)-benzonitrile; 5-(2,5-Dimethoxy-3,4-dimethyl-phenyl)-2,2,7,8-tetramethyl-chroman-6-ol; 5-(6-Hydroxy-2,2,7,8-tetramethyl-chroman-5-yl)-benzene-1,2,3-triol; 5-(6-Hydroxy-2,2,7,8-tetramethyl-chroman-5-yl)-2,3-dimethyl-benzene-1,4-diol; 5-(2-Chloro-phenyl)-2,2,7,8-tetramethyl-chroman-6-ol; 5-Furan-2-yl-2,2,7,8-tetramethyl-chroman-6-ol; 5-Allylsulfanylmethyl-2,2,8-trimethyl-7-(3-methyl-butyl)-chroman-6-ol; 5-Cyclopentylsulfanylmethyl-2,2,7,8-tetramethyl-chroman-6-ol; 5-Hexylsulfanylmethyl-2,2,7,8-tetramethyl-chroman-6-ol; 5-Allylsulfanylmethyl-2,2,7,8-tetramethyl-chroman-6-ol; 5-(4,6-Dimethyl-pyrimidin-2-ysulfanylmethyl)-2,2,7,8-tetramethyl-chroman-6-ol; 1-[3-(6-Hydroxy-2,2,7,8-tetramethyl-chroman-5-yl-methylsulfanyl)-2-methyl-propionyl]-pyrrolidine-2-carboxylic acid; 4-(6-Hydroxy-2,2,7,8-tetramethyl-chroman-5-ylmethylene)-5-methyl-2-phenyl-2,4-dihydro-pyrazol-3-one; 4-(6-Hydroxy-2,2,7,8-tetramethyl-chroman-5-yl-methylene)-3-phenyl-4H-isoxazol-5-one; 4-[4-(6-Hydroxy-2,2,7,8-tetramethyl-chroman-5-yl-methylene)-3-methyl-5-oxo-4,5-dihydro-pyrazol-1-yl]-benzoic acid; 4-(6-Hydroxy-2,2,7,8-tetramethyl-chroman-5-yl-methylene)-2-methyl-5-propyl-2,4-dihydro-pyrazol-3-one; 5-Hydroxy-3-(6-hydroxy-2,2,7,8-tetramethyl-chroman-5-yl-methylene)-3H-benzofuran-2-one; 2,5,7,8-Tetramethyl-2-thiophen-2-yl-chroman-6-ol; 2-(2,5-Dimethyl-thiophen-3-yl)-2,5,7,8-tetramethy l-chroman-6-ol; 2-(2,5-Dimethyl-thiophen-3-yl)-2,7,8-trimethyl-chroman-6-ol; 8-Chloro-2-(2,5-dimethyl-thiophen-3-yl)-2,5,7-trimethyl-chroman-6-ol; 5-Chloro-2,7,8-trimethyl-2-thiophen-2-yl-chroman-6-ol; 5-[3-(6-Methoxymethoxy-2,7,8-trimethyl-chroman-2-yl)-propylidene]-thiazolidine-2,4-dione; 5-[3-(6-Hydroxy-2,7,8-trimethyl-chroman-2-yl)-propylidene]-thiazolidine-2,4-dione; 3-[6-Hydroxy-2,7,8-trimethyl-2-(4,8,12-trimethyl-tridecyl)-chroman-5-yl-methylsulfanyl]-2-methyl-propionic acid; 2,7,8-Trimethyl-5-(5-methyl-1H-benzoimidazol-2-yl-sulfanylmethyl)-2-(4,8,12-trimethyl-tridecyl)-chroman-6-ol; 2-[6-Hydroxy-2,7,8-trimethyl-2-(4,8,12-trimethyl-tridecyl)-chroman-5-ylmethylsulfanyl]-ethanesulfonic acid; 5-(4,6-Dimethyl-pyrimidin-2-ylsulfanylmethyl)-2,7,8-trimethyl-2-(4,8,12-trimethyl-tridecyl)-chroman-6-ol; 4-[2-(4,8-Dimethyl-tridecyl)-6-hydroxy-2,7,8-trimethyl-chroman-5-ylmethylsulfanyl]-benzoic acid; 1-{3-[6-Hydroxy-2,7,8-trimethyl-2-(4,8,12-trimethyl-tridecyl)-chroman-5-ylmethylsulfanyl]-2-methyl-propionyl}-pyrrolidine-2-carboxylic acid; 2-(2,2-Dichloro-vinyl)-2,5,7,8-tetramethyl-chroman-6-ol; 2-(2,2-Dibromo-vinyl)-2,5,7,8-tetramethyl-chroman-6-ol; 5-(5-Chloro-3-methyl-pent-2-enyl)-2,2,7,8-tetramethyl-chroman-6-ol; 5-Chloro-2-(2,5-dimethyl-thiophen-3-yl)-2,7,8-trimethyl-chroman-6-ol; 2-(3-Chloro-propyl)-5,7-dimethyl-2-thiophen-2-yl-chroman-6-ol; 5-Chloro-2-(2,5-dimethyl-thiazol-4-yl)-2,7,8-trimethyl-chroman-6-ol; 5-Chloro-2-(2,5-dimethyl-thiazol-4-yl)-2,7, 8-trimethyl-2H-chromen-6-ol; and 5-Chloro-2-(2,5-dimethyl-thiazol-4-yl)-2,7,8-trimethyl-chroman-6-ol.

Compounds such as: dimebolin (2,8-dimethyl-5-(2-(6-methylpyridin-3-yl)ethyl)-2,3,4,5-tetrahydro-1H-pyrido[4,3-b]indole), 8-chloro-2-methyl-5-(2-(6-methylpyridin-3-yl) ethyl)-2,3,4,5-tetrahydro-1H-pyrido[4,3-b]indole, mebhydroline (5-benzyl-2-methyl-2,3,4,5-tetrahydro-1H-pyrido[4,3-b]indole), 2,8-dimethyl-1,3,4,4a,5,9b-hexahydro-1H-pyrido[4,3-b]indole, 8-fluoro-2-(3-(pyridin-3-yl) propyl)-2,3,4,5-tetrahydro-1H-pyrido[4,3-b]indole, and 8-methyl-1,3,4,4a,5,9b-tetrahydro-1H-pyrido[4,3-b]indole.

Compounds such as: 2-(3-hydroxy-3-methylbutyl)-3,5-dimethyl-6-(4-(trifluoromethyl)phenyl)cyclohexa-2,5-diene-1,4-dione; 2-(3-hydroxy-3-methylbutyl)-6-(4-methoxyphenyl)-3,5-dimethylcyclohexa-2,5-diene-1,4-dione; 4-(5-(3-hydroxy-3-methylbutyl)-2,4-dimethyl-3,6-dioxocyclohexa-1,4-dienyl)benzonitrile; 2-(3-hydroxy-3-methylbutyl)-3,5-dimethyl-6-(naphthalen-2-yl)cyclohexa-2,5-diene-1,4-dione; 2-(3,4-difluorophenyl)-6-(3-hydroxy-3-methylbutyl)-3,5-dimethylcyclohexa-2,5-diene-1,4-dione; 2-(4-fluorophenyl)-6-(3-hydroxy-3-methylbutyl)-3,5-dimethylcyclohexa-2,5-diene-1,4-dione; 2-(4-chlorophenyl)-6-(3-hydroxy-3-methylbutyl)-3,5-dimethylcyclohexa-2,5-diene-1,4-dione; 2-(2,3-dihydrobenzofuran-2-yl)-6-(3-hydroxy-3-methylbutyl)-3,5-dimethylcyclohexa-2,5-diene-1,4-dione; 2-(3-hydroxy-3-methylbutyl)-5,6-dimethyl-3-phenethylcyclohexa-2,5-diene-1,4-dione; 2-(3-hydroxy-3-methylbutyl)-5,6-dimethyl-3-phenylcyclohexa-2,5-diene-1,4-dione; 2-benzyl-3-(3-hydroxy-3-methylbutyl)-5,6-dimethylcyclohexa-2,5-diene-1,4-dione; 2-(3-hydroxy-3-methylbutyl)-5,6-dimethyl-3-(3-phenylpropyl)cyclohexa-2,5-diene-1,4-dione; 2-(1-hydroxy-2-phenylethyl)-3-(3-hydroxy-3-methylbutyl)-5,6-dimethylcyclohexa-2,5-diene-1,4-dione; 2-(3-hydroxy-3-methylbutyl)-3-(4-methoxyphenyl)-5,6-dimethyl-cyclohexa-2,5-diene-1,4-dione; 2-(3-hydroxy-3-methylbutyl)-5,6-dimethyl-3-(4-(trifluoromethyl)-phenyl)cyclohexa-2,5-diene-1,4-dione; 2-(3-hydroxy-3-methylbutyl)-5,6-dimethyl-3-(naphthalen-2-yl)cyclohexa-2,5-diene-1,4-dione; 2-(benzofuran-2-yl)-3-(3-hydroxy-3-methylbutyl)-5,6-dimethylcyclohexa-2,5-diene-1,4-dione; 2-(4-chlorophenyl)-3-(3-hydroxy-3-methylbutyl)-5,6-dimethylcyclohexa-2,5-diene-1,4-dione; 2-(4-ethylphenyl)-3-(3-hydroxy-3-methylbutyl)-5,6-dimethylcyclohexa-2,5-diene-1,4-dione; 2-(3-hydroxy-3-methylbutyl)-5,6-dimethyl-3-(3-(trifluoromethyl)phenyl)-cyclohexa-2,5-diene-1,4-dione; 2-(4-tert-butylphenyl)-3-(3-hydroxy-3-methylbutyl)-5,6-dimethyl-cyclohexa-2,5-diene-1,4-dione; 2-(4-fluorophenyl)-3-(3-hydroxy-3-methylbutyl)-5,6-dimethylcyclohexa-2,5-diene-1,4-dione; 2-(3-fluorophenyl)-3-(3-hydroxy-3-methylbutyl)-5,6-dimethylcyclohexa-2,5-diene-1,4-dione; 4-(2-(3-hydroxy-3-methylbutyl)-4,5-dimethyl-3,6-dioxocyclohexa-1,4-dienyl) benzonitrile; 2-(3,4-difluorophenyl)-3-(3-hydroxy-3-methylbutyl)-5,6-dimethyl-cyclohexa-2,5-diene-1,4-dione; 2-(2-fluorophenyl)-3-(3-hydroxy-3-methylbutyl)-5,6-dimethylcyclohexa-2,5-diene-1,4-dione; 2-(3-hydroxy-3-methylbutyl)-3-(3-methoxyphenyl)-5,6-dimethyl-cyclohexa-2,5-diene-1,4-dione; 2-(4-fluoro-2-methoxyphenyl)-3-(3-hydroxy-3-methylbutyl)-5,6-dimethylcyclohexa-2,5-diene-1,4-dione; 2-(benzo[d][1,3]dioxol-5-yl)-3-(3-hydroxy-3-methylbutyl)-5,6-dimethylcyclohexa-2,5-diene-1,4-dione; 2-(2,4-difluorophenyl)-3-(3-hydroxy-3-methylbutyl)-5,6-dimethylcyclohexa-2,5-diene-1,4-dione; 2-(3-hydroxy-3-methylbutyl)-3-(4-methoxyphenyl)-5,6-dimethylcyclohexa-2,5-diene-1,4-dione; 2-(3,5-bis(trifluoromethyl)phenyl)-3-(3-hydroxy-3-methylbutyl)-5,6-dimethylcyclohexa-2,5-diene-1,4-dione; 2-(4-chlorophenyl)-6-(3-hydroxy-3-methylbutyl)-3,5-dimethylcyclohexa-2,5-diene-1,4-dione; 2-(3-hydroxy-3-methylbutyl)-5,6-dimethyl-3-(2-(thiazol-2-yl)ethyl)cyclohexa-2,5-diene-1,4-dione; 2-(3-hydroxy-3-methylbutyl)-5,6-dimethyl-3-(2-(thiazol-5-yl)ethyl)cyclohexa-2,5-diene-1,4-dione; 2-(3-hydroxy-3-methylbutyl)-5,6-dimethyl-3-(2-(pyridin-2-yl)ethyl)cyclohexa-2,5-diene-1,4-dione; 2-(3-hydroxy-3-methylbutyl)-5,6-dimethyl-3-(2-(pyridazin-4-yl)ethyl)cyclohexa-2,5-diene-1,4-dione; 2-(3-hydroxy-3-methylbutyl)-5,6-dimethyl-3-(2-(thiophen-2-yl)ethyl)cyclohexa-2,5-diene-1,4-dione; 2-(3-hydroxy-3-methylbutyl)-5,6-dimethyl-3-(2-(thiophen-3-yl)ethyl)cyclohexa-2,5-diene-1,4-dione; 2-(2-(furan-2-yl)ethyl)-3-(3-hydroxy-3-methylbutyl)-5,6-dimethylcyclohexa-2,5-diene-1,4-dione; 2-(2-(furan-3-yl)ethyl)-3-(3-hydroxy-3-methylbutyl)-5,6-dimethylcyclohexa-2,5-diene-1,4-dione; 2-(2-(1H-pyrazol-5-yl)ethyl)-3-(3-hydroxy-3-methylbutyl)-5,6-dimethylcyclohexa-2,5-diene-1,4-dione; 2-(2-(1H-pyrazol-4-yl)ethyl)-3-(3-hydroxy-3-methylbutyl)-5,6-dimethyl-cyclohexa-2,5-diene-1,4-dione; 2-(2-(1H-pyrazol-1-yl)ethyl)-3-(3-hydroxy-3-methylbutyl)-5,6-dimethylcyclohexa-2,5-diene-1,4-dione; 2-(2-(1H-imidazol-5-yl)ethyl)-3-(3-hydroxy-3-methylbutyl)-5,6-dimethylcyclohexa-2,5-diene-1,4-dione; 2-(2-(1H-imidazol-2-yl)ethyl)-3-(3-hydroxy-3-methylbutyl)-5,6-dimethylcyclohexa-2,5-diene-1,4-dione; 2-(3-hydroxy-3-methylbutyl)-5,6-dimethyl-3-(2-(oxazol-5-yl)ethyl) cyclohexa-2,5-diene-1,4-dione; 2-(3-hydroxy-3-methylbutyl)-5,6-dimethyl-3-(2-(oxazol-2-yl)ethyl) cyclohexa-2,5-diene-1,4-dione; 2-(3-hydroxy-3-methylbutyl)-5,6-dimethyl-3-(2-(oxazol-4-yl)ethyl) cyclohexa-2,5-diene-1,4-dione; and 2-(2-(1H-indol-3-yl) ethyl)-3-(3-hydroxy-3-methylbutyl)-5,6-dimethylcyclohexa-2,5-diene-1,4-dione.

Compounds such as:

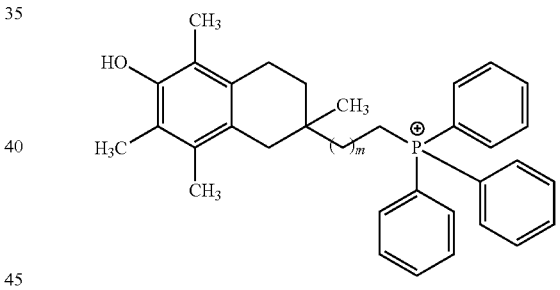

wherein m is —$C_1$-$C_{20}$ alkyl, —$C_1$-$C_{20}$ alkenyl, —$C_1$-$C_{20}$ alkynyl, or —$C_1$-$C_{20}$ containing at least one double bond and at least one triple bond, and the counterion is a pharmaceutically acceptable anion.

Compounds such as: 3-(4,5-dimethoxy-2-methyl-3,6-dioxo-1,4-cyclohexadien-1-yl)propyl triphenylphosphonium salts; 4-(4,5-dimethoxy-2-methyl-3,6-dioxo-1,4-cyclohexadien-1-yl)butyl triphenylphosphonium salts; 5-(4,5-dimethoxy-2-methyl-3,6-dioxo-1,4-cyclohexadien-1-yl)pentyl triphenylphosphonium salts; 6-(4,5-dimethoxy-2-methyl-3,6-dioxo-1,4-cyclohexadien-1-yl)hexyl triphenylphosphonium salts; 7-(4,5-dimethoxy-2-methyl-3,6-dioxo-1,4-cyclohexadien-1-yl)heptyl triphenylphosphonium salts; 8-(4,5-dimethoxy-2-methyl-3,6-dioxo-1,4-cyclohexadien-1-yl) octyl triphenylphosphonium salts; 9-(4,5-dimethoxy-2-methyl-3,6-dioxo-1,4-cyclohexadien-1-yl)nonyl triphenylphosphonium salts; 10-(4,5-dimethoxy-2-methyl-3,6-dioxo-1,4-cyclohexadien-1-yl)decyl triphenylphosphonium salts; 11-(4,5-dimethoxy-2-methyl-3,6-dioxo-1,4-cyclohexadien-1-yl)undecyl triphenylphosphonium salts; 12-(4,5-dimethoxy-2-methyl-3,6-dioxo-1,4-cyclohexadien-1- yl)dodecyl triphenylphosphonium salts; 13-(4,5-dimethoxy-2-methyl-3,6-dioxo-1,4-cyclohexadien-1-yl)propyldecyl triphenylphosphonium salts; 14-(4,5-dimethoxy-2-methyl-3,6-dioxo-1,4-cyclohexadien-1-yl)butyldecyl triphenylphosphonium salts; 15-(4,5-dimethoxy-2-methyl-3,6-dioxo-1,4-cyclohexadien-1-yl)pentadecyl triphenylphosphonium salts; 16-(4,5-dimethoxy-2-methyl-3,6-dioxo-1,4-cyclohexadien-1-yl)hexadecyl triphenylphosphonium salts; 17-(4,5-dimethoxy-2-methyl-3,6-dioxo-1,4-cyclohexadien-1-yl)heptadecyl triphenylphosphonium salts; 18-(4,5-dimethoxy-2-methyl-3,6-dioxo-1,4-cyclohexadien-1-yl) octadecyl triphenylphosphonium salts; 19-(4,5-dimethoxy-2-methyl-3,6-dioxo-1,4-cyclohexadien-1-yl)nonadecyl triphenylphosphonium salts; 20-(4,5-dimethoxy-2-methyl-3,6-dioxo-1,4-cyclohexadien-1-yl)icosyl triphenylphosphonium salts; 3-(4,5-dimethoxy-2-methyl-3,6-dihydroxyphenyl)propyl triphenylphosphonium salts; 4-(4,5-dimethoxy-2-methyl-3,6-dihydroxyphenyl)butyl triphenylphosphonium salts; 5-(4,5-dimethoxy-2-methyl-3,6-dihydroxyphenyl) pentyl triphenylphosphonium salts; 6-(4,5-dimethoxy-2-methyl-3,6-dihydroxyphenyl)hexyl triphenylphosphonium salts; 7-(4,5-dimethoxy-2-methyl-3,6-dihydroxyphenyl) heptyl triphenylphosphonium salts; 8-(4,5-dimethoxy-2-methyl-3,6-dihydroxyphenyl)octyl triphenylphosphonium salts; 9-(4,5-dimethoxy-2-methyl-3,6-dihydroxyphenyl) nonyl triphenylphosphonium salts; 10-(4,5-dimethoxy-2-methyl-3,6-dihydroxyphenyl)decyl triphenylphosphonium salts; 11-(4,5-dimethoxy-2-methyl-3,6-dihydroxyphenyl) undecyl triphenylphosphonium salts; 12-(4,5-dimethoxy-2-methyl-3,6-dihydroxyphenyl)dodecyl triphenylphosphonium salts; 13-(4,5-dimethoxy-2-methyl-3,6-dihydroxybenzyl)propyldecyl triphenylphosphonium salts; 14-(4,5-dimethoxy-2-methyl-3,6-dihydroxyphenyl)butyldecyl triphenylphosphonium salts; 15-(4,5-dimethoxy-2-methyl-3,6-dihydroxyphenyl)pentadecyl triphenylphosphonium salts; 16-(4,5-dimethoxy-2-methyl-3,6-dihydroxyphenyl)hexadecyl triphenylphosphonium salts; 17-(4,5-dimethoxy-2-methyl-3,6-dihydroxyphenyl)heptadecyl triphenylphosphonium salts; 18-(4,5-dimethoxy-2-methyl-3,6-dihydroxyphenyl)octadecyl triphenylphosphonium salts; 19-(4,5-dimethoxy-2-methyl-3,6-dihydroxyphenyl)nonadecyl triphenylphosphonium salts; 20-(4,5-dimethoxy-2-methyl-3,6-dihydroxyphenyl)icosyl triphenylphosphonium salts; wherein the counterion of the salt is a pharmaceutically acceptable anion such as bromide, methanesulfonate ethanesulfonate, propanesulfonate, benzenesulfonate, p-toluenesulfonate, or 2-naphthylene sulfonate.

Additionally, it is contemplated that co-administration of antioxidants could take the form of consuming foods known to have increased levels of beneficial antioxidants. Such foods include both regular foods and "superfoods" which contain antioxidants. These foods include fruits, vegetables, and other foodstuffs such as strawberries, blackcurrants, blackberries, oranges, blueberries, pomegranates, tea, coffee, olive oil, chocolate, cinnamon, herbs, red wine, grain cereals, eggs, meat, legumes, nuts, spinach, turnip, rhubarb, cocao beans, maize, beans, cabbage, and the like.

Delivery and Additional Formulations:

It is well known that triglycerides are the main constituents of vegetable oils and animal fats. It is also known that a triglyceride is an ester compound derived from glycerol and three fatty acids. Triglycerides are metabolized by enzymes such as lipases which hydrolyze ester bonds and release fatty acids and glycerol. Indeed, this metabolism releases fatty acids which can then be taken upon by cells via a fatty acid transporter protein. It is contemplated that PUFAs and PUFA mimetics that are useful in treating various diseases may be incorporated into fats such as triglycerides, diglycerides, and/or monoglycerides for administration to a patient.

The delivery of the PUFAs, PUFA mimetics, PUFA pro-drugs, and triglycerides containing PUFAs and/or PUFA mimetics could be through a modified diet. Alternatively, the PUFAs, PUFA mimetics, PUFA pro-drugs, and triglycerides containing PUFAs and/or PUFA mimetics can be administered as foods or food supplements, on their own or as complexes with 'carriers', including, but not limited to, complexes with albumin.

Other methods of delivering the reinforced PUFAs or their precursors, such as methods typically used for drug delivery and medication delivery, can also be employed. These methods include, but are not limited to, peroral delivery, topical delivery, transmucosal delivery such as nasal delivery, nasal delivery through cribriform plate, intravenous delivery, subcutaneous delivery, inhalation, or through eye drops.

Targeted delivery methods and sustained release methods, including, but not limited to, the liposome delivery method, can also be employed.

It is contemplated that the isotopically modified compounds described herein may be administered over a course of time, in which the cells and tissues of the subject will contain increasing levels of isotopically modified compounds over the course of time in which the compounds are administered.

Compositions containing the active ingredient may be in a form suitable for oral use, for example, as tablets, troches, lozenges, aqueous or oily suspensions, oil-in-water emulsions, dispersible powders or granules, emulsions, hard or soft capsules, or syrups or elixirs. Such compositions may contain excipients such as bulking agents, solubilization agents, taste masking agents, stabilizers, coloring agents, preservatives and other agents known to those ordinarily skilled in the art of pharmaceutical formulation. In addition, oral forms may include food or food supplements containing the compounds described herein. In some embodiments supplements can be tailor-made so that one type of PUFA, such as omega-3 or omega-6 fatty acids can be added to food or used as a supplement depending on the dominant fat that the food or the subject's diet contains. Moreover, compositions can be tailor-made depending on the disease to be treated. For example, an LDL related condition may require more D-linoleic acid because cardiolipin, which is made of linoleic acid, is oxidized. In other embodiments, such as retinal disease and neurological/CNS conditions may require more omega-3 fatty acids such as D-linolenic acid, because D-omega-3 fatty acids are more relevant for treating these diseases. In some aspects, when the disease is associated with FINE, then D-omega-6 fatty acids should be prescribed, whereas for HHE, D-omega-3 fatty acids should be prescribed.

Compositions may also be suitable for delivery by topical application, as a spray, cream, ointment, lotion, or as a component or additive to a patch, bandage or wound dressing. In addition the compound can be delivered to the site of the disease by mechanical means, or targeted to the site of the disease through the use of systemic targeting technologies such as liposomes (with or without chemical modification that provides them with affinity for the diseased tissue), antibodies, aptamers, lectins, or chemical ligands such as albumin, with affinity for aspects of the diseased tissue that are less abundant or not present on normal tissue. In some aspects, topical application of cosmetics may include the use of a carrier which is an isotopically modified compound or mimetic described herein for delivering through skin such as by a patch. Eye disorders may be treated with eyedrops.

A pharmaceutical composition may also be in a form suitable for administration by injection. Such compositions may be in the form of a solution, a suspension or an emulsion. Such compositions may include stabilizing agents, antimicrobial agents or other materials to improve the function of the medicament. Some aspects of the invention also encompass dry or desiccated forms of the compounds which can readily be formed or reconstituted into a solution suspension or emulsion suitable for administration by injection, or for oral or topical use. Delivery by injection may be suitable for systemic delivery, and also local delivery such as injection into the eye for treating disorders relating to the eye.

Dosages

In some embodiments, compounds are dosed at about 0.01 mg/kg to about 1000 mg/kg, about 0.1 mg/kg to about 100 mg/kg, and/or about 1 mg/kg to about 10 mg/kg. In other embodiments, compounds are dosed at about: 0.01, 0.1, 1.0, 5.0, 10, 25, 50, 75, 100, 150, 200, 300, 400, 500, and/or 1000 mg/kg.

EXAMPLES

Experimental: MALDI-TOF mass-spectra were recorded on a PE-ABI Voyager Elite delayed extraction instrument. Spectra were acquired with an accelerating voltage of 25 KV and 100 ms delay in the positive ion mode. Unless otherwise specified, the 1H NMR spectra were recorded on a Varian Gemini 200 MHz spectrometer. HPLC was carried out on a Waters system. Chemicals were from Sigma-Aldrich Chemical Company (USA), Avocado research chemicals (UK), Lancaster Synthesis Ltd (UK), and Acros Organics (Fisher Scientific, UK). Silica gel, TLC plates and solvents were from BDH/Merck. IR spectra were recorded with Vertex 70 spectrometer. $^1$H and $^{13}$C NMR spectra were obtained with a Bruker AC 400 instrument at 400 and 100 MHz respectively, in CDCl$_3$ (TMS at δ=0.00 or CHCl$_3$ at δ=7.26 for $^1$H and CHCl$_3$ at δ=77.0 for $^{13}$C as an internal standard).

One of ordinary skill in the art will recognize that the below described syntheses can be readily modified to prepare additional oxidation-resistant compounds. For example, one will recognize the ester of one type of stabilized compound can be cleaved to afford the corresponding carboxylic acid. Likewise, carboxylic acids can be readily converted into additional derivatives, such as esters. Additionally, one will appreciate that by varying the identity of the isotopically labeled starting materials, isotopic variants of the below described compounds may be prepared. In the below described syntheses, paraformaldehyde-d$_2$ is used as an isotopically labeled starting material. One will readily appreciate that the same synthetic transformations can be used with paraformaldehyde-d$_1$, formaldehyde-d$_1$, para-formaldehyde-d$_2$, formaldehyde-d$_2$, and carbon-13 labeled variants of the aforementioned compounds. Formaldehyde-d$_1$ is a well-characterized compound and is readily available from known sources such as formic acid-d$_1$, formic acid-d$_2$, and/or dichloromethane-d$_1$ using generally known and understood synthetic transformations. Furthermore, radioactive analogues of the compounds described herein can be prepared using tritium-containing starting materials. These compounds would be useful for determining incorporation in the cells and tissues of animals.

Example 1

Synthesis of 11,11-D2-linoleic acid

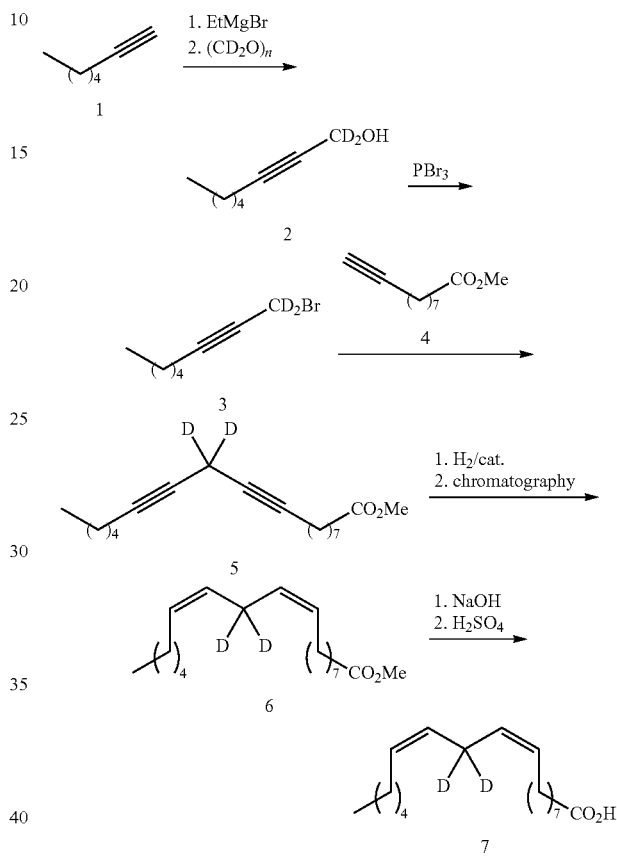

1,1-Dideutero-oct-2-yn-1-ol (2) To a solution of ethylmagnesium bromide prepared from bromoethane (100 ml), 1,2-dibromoethane (1 ml) and magnesium turnings (31.2 g) in dry THF (800 ml), heptyn-1 ((1); 170 ml) was added dropwise over 30-60 min under argon. The reaction mixture was stirred for 1 h, and then deuteroparaform (30 g) was carefully added in one portion. The reaction mixture was gently refluxed for 2 h, chilled to −10° C., and then 5-7 ml of water was slowly added. The mixture was poured into 0.5 kg slurry of crushed ice and 40 ml concentrated sulphuric acid and washed with 0.5 L of hexane. The organic phase was separated, and the remaining aqueous phase was extracted with 5:1 hexane:ethyl acetate (3×300 ml). The combined organic fraction was washed with sat. NaCl (1×50 ml), sat. NaHCO$_3$, (1×50 ml), and dried over Na$_2$SO$_4$. The solvent was evaporated in vacuo to yield 119.3 g (99%) of colorless oil which was used without further purification. HRMS, m/z calculated for C$_8$H$_{12}$D$_2$O: 128.1168; found: 128.1173. $^1$H NMR (CDCl$_3$, δ): 2.18 (t, J=7.0, 2H), 1.57 (s, 1H), 1.47 (q, J=7.0 Hz, 2H), 1.31 (m, 4H), 0.87 (t, J=7.0 Hz, 3H).

1,1-Dideutero-1-bromo-oct-2-yne (3) To a solution of (2) (3.48 g; 27.2 mmol) and pyridine (19 ml) in dry diethyl ether (300 ml), 36 ml of PBr$_3$ in 35 ml diethyl ether was added dropwise with stirring over 30 min at −15° C. under argon. The reaction mixture was allowed to gradually warm up to r.t. and then refluxed 3 h with stirring and 1 h without stirring. The reaction mixture was then cooled down to −10° C. and 500 ml of cold water was added. When the residue dissolved, saturated NaCl (250 ml) and hexane (250 ml) were added, and the organic layer was separated. The aqueous fraction was washed with hexane (2×100 ml), and the combined organic fractions were washed with NaCl (2×100 ml) and dried over $Na_2SO_4$ in presence of traces of hydroquinone and triethylamine. The solvent was removed by distillation at atmospheric pressure followed by rotary evaporation. The residue was fractionated by vacuum distillation (3 mm Hg) to give 147.4 g (82% counting per deutero-paraform) of pale yellow oil. B.p. 75° C. HRMS, m/z calculated for $C_8H_{11}D_2Br$: 190.0324; found: 189.0301, 191.0321. $^1H$ NMR ($CDCl_3$, δ): 2.23 (t, J=7.0 Hz, 2H, $CH_2$), 1.50 (m, 2H, $CH_2$), 1.33 (m, 4H, $CH_2$), 0.89 (t, J=6.9 Hz, 3H, $CH_3$), 11,11-Dideutero-octadeca-9,12-diynoic acid methyl ester (5) CuI (133 g) was quickly added to 400 ml of DMF (freshly distilled over $CaH_2$), followed by dry NaI (106 g), $K_2CO_3$ (143 g). Dec-9-ynoic acid methyl ester ((4); 65 g) was then added in one portion, followed by bromide (3) (67 g). Additional 250 ml of DMF was used to rinse the reagents off the flask walls into the bulk of reaction mixture, which was then stirred for 12 h. 500 ml of saturated aqueous $NH_4Cl$ was then added with stirring, followed in a few minutes by saturated aqueous NaCl and then by a 5:1 mixture of hexane:EtOAc (300 ml). The mixture was further stirred for 15 min and then filtered through a fine mesh Schott glass filter. The residue was washed with hexane:EtOAc mix several times. The organic fraction was separated, and the aqueous phase was additionally extracted (3×200 ml). The combined organic fraction was dried ($Na_2SO_4$), traces of hydroquinone and diphenylamine were added, and the solvent was evaporated in vacuo. The residue was immediately distilled at 1 mm Hg, to give 79 g (77%) of a 165-175° C. boiling fraction. HRMS, m/z calculated for $C_{19}H_{28}D_2O_2$: 292.2369; found: 292.2365. $^1H$ NMR ($CDCl_3$, δ): 3.67 (s, 3H,$OCH_3$),2.3 (t,J=7.5 Hz, 2H, $CH_2$),2.14(t, J=7.0 Hz, 4H, $CH_2$), 1.63 (m, 2H, $CH_2$), 1.47 (m, 4H, $CH_2$), 1.3 (m, 10H, $CH_2$), 0.88 (t, J=7.0 Hz, 3H, $CH_3$).

11,11-Dideutero-cis,cis-octadeca-9,12-dienoic acid methyl ester (6) A suspension of nickel acetate tetrahydrate (31.5 g) in 96% EtOH (400 ml) was heated with stirring to approx. 50-60° C. until the salt dissolved. The flask was flushed with hydrogen, and then 130 ml of $NaBH_4$ solution, (prepared by a 15 min stirring of $NaBH_4$ suspension (7.2 g) in EtOH (170 ml) followed by filtering) was added dropwise over 20-30 min with stirring. In 15-20 min ethylenediamine (39 ml) was added in one portion, followed in 5 min by an addition of (5) (75 g) in EtOH (200 ml). The reaction mixture was very vigorously stirred under hydrogen (1 atm). The absorption of hydrogen stopped in about 2 h. To the reaction mixture, 900 ml of hexane and 55 ml of ice cold AcOH were added, followed by water (15 ml). Hexane (400 ml) was added, and the mixture was allowed to separate. Aqueous fractions were extracted by 5:1 mix of hexane:EtOAc. The completion of extraction was monitored by TLC. The combined organic phase was washed with diluted solution of $H_2SO_4$, followed by saturated $NaHCO_3$ and saturated NaCl, and then dried over $Na_2SO_4$. The solvent was removed at reduced pressure. Silica gel (Silica gel 60, Merck; 162 g) was added to a solution of silver nitrate (43 g) in anhydrous MeCN (360 ml), and the solvent removed on a rotavap. The obtained impregnated silica gel was dried for 3 h at 50° C. (aspiration pump) and then 8 h on an oil pump. 30 g of this silica was used per gram of product. The reaction mixture was dissolved in a small volume of hexane and applied to the silver-modified silica gel, and pre-washed with a 1-3% gradient of EtOAc. When the non-polar contaminants were washed off (control by TLC), the product was eluted with 10% EtOAc and the solvent evaporated in vacuo to give 52 g of the title ester (6) as a colorless liquid. HRMS, m/z calculated for $C_{19}H_{32}D_2O_2$: 296.2682; found: 296.2676. IR ($CCl_4$): $\tilde{v}$=1740 $cm^{-1}$. $^1H$ NMR ($CDCl_3$, δ): 5.32 (m, 4H), 3.66 (s, 3H, $OCH_3$), 2.29 (t, J=7.5 Hz, 2H, $CH_2$), 2.02 (m, 4H, $CH_2$), 1.60 (m, 2H, $CH_2$), 1.30 (m, 14H, $CH_2$), 0.88 (t, J=7.0 Hz, 3H, $CH_3$).

11,11-Dideutero-cis,cis-octadeca-9,12-dienoic acid (7) A solution of KOH (46 g) in water (115 ml) was added to a solution of ester (6) (46 g) in MeOH (60 ml). The reaction mixture was stirred at 40-50° C. for 2 h (control by TLC) and then diluted with 200 ml of water. Two thirds of the solvent were removed (rotavap). Diluted sulphuric acid was added to the residue to pH 2, followed by diethyl ether with a little pentane. The organic layer was separated and the aqueous layer washed with diethyl ether with a little pentane. The combined organic fractions were washed with saturated aqueous NaCl and then dried over $Na_2SO_4$. The solvent was evaporated to give 43 g of (7) (99%). IR($CCl_4$): $\tilde{v}$=1741, 1711 $cm^{-1}$.

Example 2

Synthesis of 11,11,14,14-D4-linolenic acid

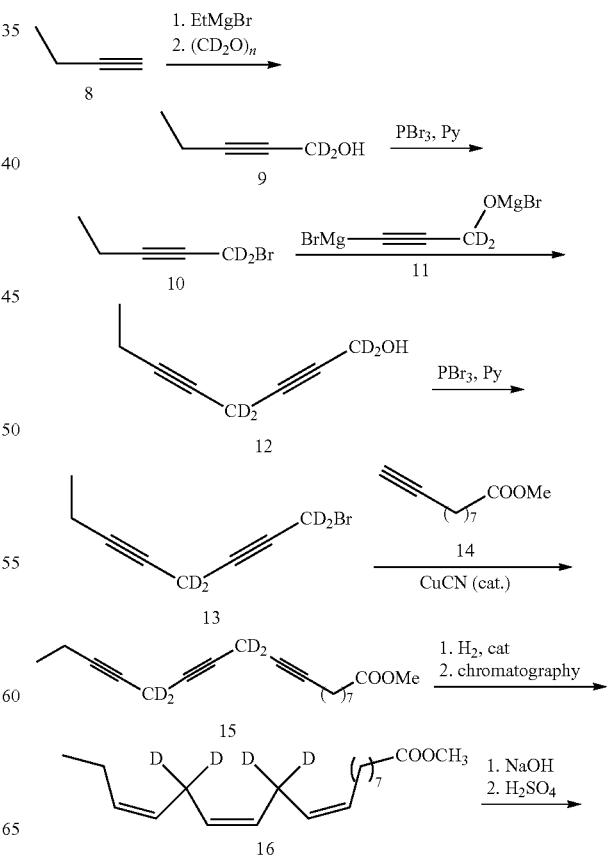

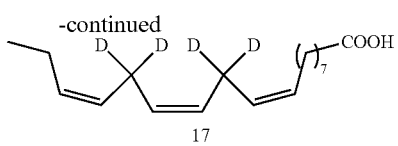

17

1,1-Dideutero-pent-2-yn-1-ol (9) But-1-yne (8) was slowly bubbled through a solution of ethylmagnesium bromide prepared from bromoethane (100 ml) and magnesium turnings (31.3 g) in dry THF (800 ml) on a bath (−5° C.). Every now and then the bubbling was stopped and the cylinder with but-1-yne was weighed to measure the rate of consumption. The supply of alkyne was stopped shortly after a voluminous precipitate formed (the measured mass of alkyne consumed was 125 g). The reaction mixture was warmed up to r.t. over 30 min, and then stirred for 15 min. The mixture was then heated up to 30° C., at which point the precipitate dissolved, and then stirred at r.t. for another 30 min. Deuteroparaform (28 g) was added in one portion and the mixture was refluxed for 3 h, forming a clear solution. It was cooled down to r.t. and poured into a mixture of crushed ice (800 g) and 50 ml conc. $H_2SO_4$. Hexane (400 ml) was added and the organic layer was separated. The aqueous phase was saturated with NaCl and extracted with a 4:1 mixture of hexane:EtOAc (1 L). The completion of extraction process was monitored by TLC. The combined organic phases were washed with saturated NaCl, $NaHCO_3$ and again NaCl, and dried over $Na_2SO_4$. The solvent was removed by distillation at the atmospheric pressure (max vapor temperature 105° C.). The residue (70.5 g; 94%) was used without further purification. HRMS, m/z calculated for $C_5H_6D_2O$: 86.0699; found: 86.0751. $^1$H NMR ($CDCl_3$, δ): 2.21 (q, J=7.5 Hz, 2H, $CH_2$), 1.93 (br s, 1H, OH), 1.12 (t, J=7.5 Hz, 3H, $CH_3$). $^{13}$C NMR ($CDCl_3$, δ): 87.7, 77.6, 13.7, 12.3 (signal of $CD_2$ is absent).

1,1-Dideutero-1-bromo-pent-2-yne (10) To a solution of (9) (70.5 g) and pyridine (16.5 ml) in dry diethyl ether (280 ml), 32.3 ml of $PBr_3$ in 50 ml diethyl ether was added dropwise with stirring over 30 min at −10° C. under argon. The reaction mixture was allowed to gradually warm up to r.t. over 1 h. A small amount of hydroquinone was added, and the mixture was then refluxed for 4.5 h. The reaction mixture was then cooled down to −10° C. and 350 ml of cold water was added. When the residue dissolved, saturated NaCl (350 ml) and hexane (300 ml) were added, and the organic layer was separated. The aqueous fraction was washed with diethyl ether (2×150 ml), and the combined organic fractions were washed with NaCl (2×50 ml) and dried over $Na_2SO_4$ in presence of traces of hydroquinone and triethylamine. The solvent was removed at atmospheric pressure, and then the 147-155° C. boiling fraction was distilled off. Alternatively, upon reaching 100° C., the distillation at atmospheric pressure was stopped and the product distilled off at 77-84° C. (25 mm Hg). Yield: 107 g of clear liquid. HRMS, m/z calculated for $C_5H_5D_2Br$: 147.9855; found: 146.9814, 148.9835. IR($CCl_4$): ṽ=2251 $cm^{-1}$. $^1$H NMR ($CDCl_3$, δ): 2.23 (q, J=7.5 Hz, 2H, $CH_2$), 1.11 (t, J=7.5 Hz, 3H, $CH_3$). $^{13}$C NMR ($CDCl_3$, δ): 89.3, 74.5, 13.4, 12.6 (signal of $CD_2$ is absent).

1,1,4,4-Tetradeutero-octa-2,5-diyn-1-ol (12) Ethylmagnesium bromide, prepared from ethyl bromide (53 ml) and magnesium turnings (15.8 g) in 400 ml of dry THF, was added in small portions to 350 ml of dry THF, simultaneously with acetylene bubbling through this mixture (at approx. 25 L/h rate) with vigorous stirring. The Grignard reagent solution was fed to the mixture at approx. 10 ml per 2-5 min. When all ethylmagnesium bromide was added (after approx. 2.5 h), acetylene was bubbled through the system for another 15 min. Deuteroparaform (17.3 g) and CuCl (0.2 g) were added under argon, and the reaction mixture was refluxed without stirring for 2.5 h, until deuteroparaform dissolved, to yield a solution of (11). Ethylmagnesium bromide solution, prepared from 14.8 g magnesium and 50 ml ethyl bromide in 250 ml of dry THF, was added dropwise to the reaction mixture over 20 min. When the gas emanation ceased, a condenser was attached and 250 ml of solvent were distilled off. The reaction mixture was then cooled to 30° C., and CuCl (1.4 g) was added followed by a dropwise addition, over 15 min, of bromide (10) (69 g). The reaction mixture was then refluxed for 5 h, cooled slightly (a precipitate will form if cooling is too fast), and poured into a slurry of crushed ice (1-1.2 kg) and 40 ml concentrated $H_2SO_4$. The mixture was washed with hexane (600 ml). The organic fraction was separated, and the aqueous fraction was additionally extracted with 5:1 hexane:EtOAc (2×400 ml). The combined organic fraction was washed, with saturated NaCl, followed by saturated $NaHCO_3$ and NaCl. The bulk of the solvent was removed at atmospheric pressure in presence of traces of hydroquinone and triethylamine. The residue was flushed through 100 ml of silica gel (eluent: 7:1 hexane:EtOAc). The bulk of the solvent was removed at the atmospheric pressure, and the remainder on a rotavap. 49.5 g (85%) of the title compound obtained was used without further purification. HRMS, m/z calculated for $C_8H_6D_4O$: 126.0979; found: 126.0899. IR($CCl_4$): ṽ=3622 $cm^{-1}$. $^1$H NMR ($CDCl_3$,δ):2.16(q, J=7.5Hz,2H, $CH_2$), 1.85 (br s, 1 H, OH), 1.11 (t, J=7.5 Hz, 3H, $CH_3$). $^{13}$C NMR ($CDCl_3$, δ): 82.3, 80.4, 78.3, 72.6, 13.7, 12.2

1,1,4,4-Tetradeutero-1-bromo-octa-2,5-diyne (13) was synthesized as described for bromide (3); 2 ml of pyridine, 14 ml $PBr_3$ and 250 ml of diethyl ether was used for 54.2 g of alcohol (12). The product was purified by distillation at 4 mm Hg. Yield: 53 g (65%) of (13); b.p. 100-110° C. HRMS, m/z calculated for $C_8H_5D_4Br$: 188.0135; found: 187.0136, 189.0143. IR($CCl_4$): ṽ=2255 $cm^{-1}$. $^1$H NMR ($CDCl_3$, δ): 2.13 (q, J=7.5 Hz, 2H, $CH_2$); 1.07 (t, J=7.5 Hz, 3H, $CH_3$). $^{13}$C NMR ($CDCl_3$, δ): 82.5, 81.8, 75.0, 72.0, 13.6, 12.2.

11,11,14,14-Tetradeutero-octadeca-8,12,15-triynoic acid methyl ester (15) was synthesized in a way similar to that described for 11,11-dideutero-octadeca-9,12-diynoic acid methyl ester (5). CuI (97 g) was quickly added to 400 ml of DMF (freshly distilled over $CaH_2$), followed by dry NaI (77.5 g), $K_2CO_3$ (104.5 g). Dec-9-ynoic acid methyl ester ((14); 47.5 g) was then added in one portion, followed by bromide (13) (48.5 g). Additional 250 ml of DMF was used to rinse the reagents off the flask walls into the bulk of reaction mixture, which was then stirred for 12 h. 500 ml of saturated aqueous $NH_4Cl$ was then added with stirring, followed in a few minutes by saturated aqueous NaCl (300 ml) followed by a 5:1 mixture of hexane:EtOAc (300 ml). The mixture was further stirred for 15 min and then filtered through a fine mesh Schott glass filter. The residue was washed with hexane:EtOAc mix several times. The organic fraction was separated, and the aqueous phase was additionally extracted (3×200 ml). The combined organic fraction was dried (Na$_2$SO$_4$), traces of hydroquinone and diphenylamine were added, and the solvent was evaporated in vacuo. The residue was immediately distilled at 1 mm Hg, to give 45.8 g (62%) of a 173-180° C. boiling fraction. An additional crystallization was carried out as follows. The ester (15) was dissolved in hexane (500 ml) and cooled down to −50° C. The crystals formed were washed in cold hexane. The yield of this step is 80%. HRMS, m/z calculated for C$_{19}$H$_{22}$D$_4$O$_2$: 290.2180; found: 290.2200. $^1$H NMR (CDCl$_3$, δ): 3.66 (s, 3H, OCH$_3$), 2.29 (t, J=7.5 Hz, 2H, CH$_2$), 2.15 (m, 4H, CH$_2$), 1.61 (m, 2H, CH$_2$), 1.47 (m, 2H, CH$_2$), 1.30 (m, 6H, CH$_2$), 1.11 (t, J=7.5 Hz, 3H, CH$_3$). $^{13}$C NMR (CDCl$_3$, δ): 174.1, 82.0, 80.6, 74.7, 74.6, 73.7, 73.0, 51.3, 33.9, 28.9, 28.6, 28.52, 28.49, 24.8, 18.5, 13.7, 12.2.

11,11,14,14-Tetradeutero-cis,cis,cis-octadeca-8,12,15-trienoic acid methyl ester (16) was synthesized in a way similar to that described for 11,11-Dideutero-cis,cis-octadeca-9,12-dienoic acid methyl ester ('6'). A suspension of nickel acetate tetrahydrate (42 g) in 96% EtOH (400 ml) was heated with stirring to approx. 50-60° C. until the salt dissolved. The flask was flushed with hydrogen, and then 130 ml of NaBH$_4$ solution, (prepared by a 15 min stirring of NaBH$_4$ suspension (7.2 g) in EtOH (170 ml) followed by filtering) was added dropwise over 20-30 min with stirring. In 15-20 min ethylenediamine (52 ml) was added in one portion, followed in 5 min by an addition of (15) (73 g) in EtOH (200 ml). The reaction mixture was very vigorously stirred under hydrogen (1 atm). The absorption of hydrogen stopped in about 2 h. To the reaction mixture, 900 ml of hexane and 55 ml of ice cold AcOH were added, followed by water (15 ml). Hexane (400 ml) was added, and the mixture was allowed to separate. Aqueous fractions were extracted by 5:1 mix of hexane:EtOAc. The completion of extraction was monitored by TLC. The combined organic phase was washed with diluted solution of H$_2$SO$_4$, followed by saturated NaHCO$_3$ and saturated NaCl, and then dried over Na$_2$SO$_4$. The solvent was removed at reduced pressure. Silica gel for purification was prepared as described for (6). 30 g of this silica was used per gram of product. The reaction mixture was dissolved in a small volume of hexane and applied to the silver-modified silica gel, and pre-washed with a 1-5% gradient of EtOAc. When the non-polar contaminants were washed off (control by TLC), the product was eluted with 10% EtOAc and the solvent evaporated in vacuo to give 42 g of the title ester (16) as a colorless liquid. HRMS, m/z calculated for C$_{19}$H$_{28}$D$_4$O$_2$: 296.2649; found: 296.2652. IR(CCl$_4$): $\tilde{\nu}$=1740 cm$^{-1}$. $^1$H NMR (CDCl$_3$, δ): 5.4 (m, 6H, CH-double bond), 3.68 (s, 3H, OCH$_3$), 2.33 (t, J=7.5 Hz, 2H, CH$_2$), 2.09 (m, 4H, CH$_2$), 1.62 (m, 2H, CH$_2$), 1.33 (m, 8H, CH$_2$), 0.97 (t, J=7.5 Hz, 3H, CH$_3$). $^{13}$C NMR (CDCl$_3$, δ): 174.1, 131.9, 130.2, 128.2, 128.1, 127.7, 126.9, 51.3, 34.0, 29.5, 29.04, 29.02, 27.1, 25.5, 24.9, 20.5, 14.2.

11,11,14,14-Tetradeutero-cis,cis,cis-octadeca-8,12,15-trienoic acid (17) A solution of KOH (1.5 g, 27 mmol) in water (2.6 ml was added to a solution of ester (16) (1.00 g, 3.4 mmol) in MeOH (15 ml). The reaction mixture was stirred at 40-50° C. for 2 h (control by TLC) and then diluted with 20 ml of water. Two thirds of the solvent were removed (rotavap). Diluted sulfuric acid was added to the residue to pH 2, followed by diethyl ether with a little pentane (50 ml). The organic layer was separated and the aqueous layer washed with diethyl ether with a little pentane (3×30 ml). The combined organic fractions were washed with saturated aqueous NaCl and then dried over Na$_2$SO$_4$. The solvent was evaporated to give 0.95 g of (17) (100%). IR(CCl$_4$): $\tilde{\nu}$=1741, 1711 cm$^{-1}$.

Example 3

Synthesis of 14,14-D2-linolenic acid

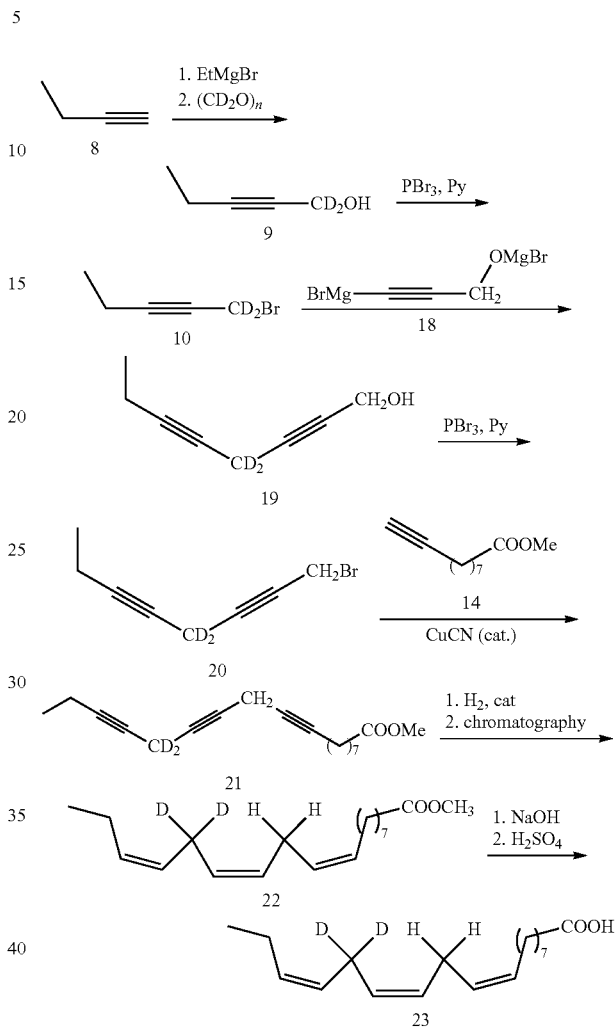

4,4-Dideutero-octa-2,5-diyn-1-ol (19) To a solution of ethylmagnesium bromide, prepared from ethyl bromide (9.2 ml, 123.4 mmol) and magnesium turnings (2.74 g, 112.8 mmol) in 40 ml of dry THF, on an ice bath with stirring, propargyl alcohol (3.16 g, 56.4 mmol) in THF (5 ml) was added dropwise over 10-15 min. The reaction mixture was allowed to warm up to r.t. and stirred for another 2 h, with occasional warming to 40° C. To thus generated dianion, 0.13 g of CuCl was added, followed by slow (over 15 min) addition of bromide (10) (6.9 g) in THF (20 ml). The reaction mixture was then stirred for 1 h at r.t. and then refluxed for 5 h. The reaction mixture was then refluxed for 5 h, cooled slightly (a precipitate will form if cooling is too fast), and poured into a slurry of crushed ice and 2.5 ml concentrated H2SO4. The mixture was washed with hexane (600 ml). The organic fraction was separated, and the aqueous fraction was additionally extracted with 5:1 hexane:EtOAc. The combined organic fraction was washed, with saturated NaCl, followed by saturated NaHCO3 and NaCl, and dried over Na2SO4. The bulk of the solvent was removed at atmospheric pressure in presence of traces of hydroquinone and triethylamine. The product was purified by CC (hexane:EtOAc=15:1) to give 3.45 g (59%) of the product 19. HRMS, m/z calculated for C8H8D2O: 124.0855; found: 124.0849. IR(CCl4): ṽ=3622 cm-1. 1H NMR (CDCl3, δ): 4.21 (m, 2H, CH2), 2.4 (m, 1H, OH), 2.16 (q, J=7.5 Hz, 2H, CH2), 1.11 (t, J=7.5 Hz, 3H, CH3). 13C NMR (CDCl3, δ): 82.3, 80.4, 78.3, 72.6, 51.0, 13.7, 12.2.

4,4-Dideutero-1-bromo-octa-2,5-diyne (20) was synthesized as described for (3), except all solvent was removed on a rotavap. From 3.4 g (27 mmol) of (19), 3.9 g (75%) of the bromide (20) was obtained, which was used without further purification. HRMS, m/z calculated for $C_8H_7D_2Br$: 186.0011; found: 185.0019, 187.0012. IR(CCl$_4$): ṽ=2255 cm$^{-1}$. $^1$H NMR (CDCl$_3$, δ): 3.88 (br s, 2H, CH$_2$), 2.13 (q, J=7.5 Hz, 2H, CH$_2$), 1.07 (t, J=7.5 Hz, 3H, CH$_3$). $^{13}$C NMR (CDCl$_3$, δ): 82.5, 81.8, 75.0, 72.0, 14.8, 13.6, 12.2.

14,14-Dideutero-octadeca-8,12,15-triynoic acid methyl ester (21) was synthesized as described for (5). The product obtained from 9.7 g CuI, 7.8 g NaI, 10.5 g K$_2$CO$_3$, 4.85 g of bromide (20), 4.75 g of methyl ester (14) and 40 ml of anhydrous DMF, was purified by CC (25:1 hexane:EtOAc) to give 4.5 g (60%) of the title compound. HRMS, m/z calculated for $C_{19}H_{24}D_2O_2$: 288.2056; found: 288.2046. $^1$H NMR (CDCl$_3$, δ): 3.66 (s, 3H, OCH$_3$), 3.12 (m, 2H, CH$_2$), 2.29 (t, J=7.5 Hz, 2H, CH$_2$), 2.15 (m, 4H, CH$_2$), 1.61 (m, 2H, CH$_2$), 1.47 (m, 2H, CH$_2$), 1.30 (m, 6H, CH$_2$), 1.11 (t, J=7.5 Hz, 3H, CH$_3$). $^{13}$C NMR (CDCl$_3$, δ): 174.1, 82.0, 80.6, 74.7, 74.6, 73.7, 73.0, 51.3, 33.9, 28.9, 28.6, 28.52, 28.49, 24.8, 18.5, 13.7, 12.2, 9.7.

14,14-Dideutero-cis,cis,cis-octadeca-8,12,15-trienoic acid methyl ester (22) was synthesized as described for the linoleic acid derivative (6). For a reduction of 4.5 g of (21), 2.6 g of nickel acetate tetrahydrate and 3.2 ml ethylenediamine was used. The product was purified on AgNO$_3$-impregnated silica gel as described for (6). HRMS, m/z calculated for $C_{19}H_{30}D_2O_2$: 294.2526; found: 294.2529. IR(CCl$_4$): ṽ=1740 cm$^{-1}$. $^1$H NMR (CDCl$_3$, δ): 5.37 (m, 6H, CH-double bond), 3.68 (s, 3H, OCH$_3$), 2.82 (m, 2H, CH$_2$), 2.33 (t, J=7.5 Hz, 2H, CH$_2$), 2.09 (m, 4H, CH$_2$), 1.62 (m, 2H, CH$_2$), 1.33 (m, 8H, CH$_2$), 0.97 (t, J=7.5 Hz, 3H, CH$_3$). $^{13}$C NMR (CDCl$_3$, δ): 174.1, 131.9, 130.2, 128.2, 128.1, 127.7, 126.9, 51.3, 34.0, 29.5, 29.1, 29.04, 29.02, 27.1, 25.5, 24.9, 20.5, 14.2.

14,14-Dideutero-cis,cis,cis-octadeca-8,12,15-trienoic acid (23) To a solution of (22) (1 g, 3.4 mmol) in MeOH (15 ml), a solution of KOH (1.5 g, 27 mmol) in water (2.6 ml) was added in one portion. The reaction mixture was then processed as described for (7) to yield 0.94 g (99%) of the title acid. IR(CCl$_4$): ṽ=1741, 1711 cm$^{-1}$.

Example 4

Synthesis of 11,11-D2-linolenic acid

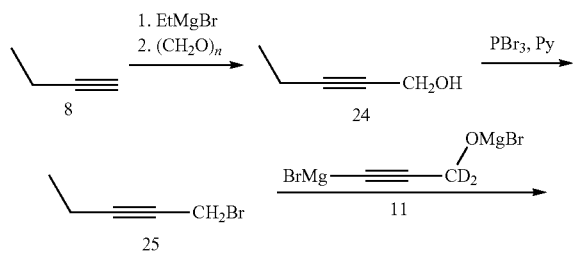

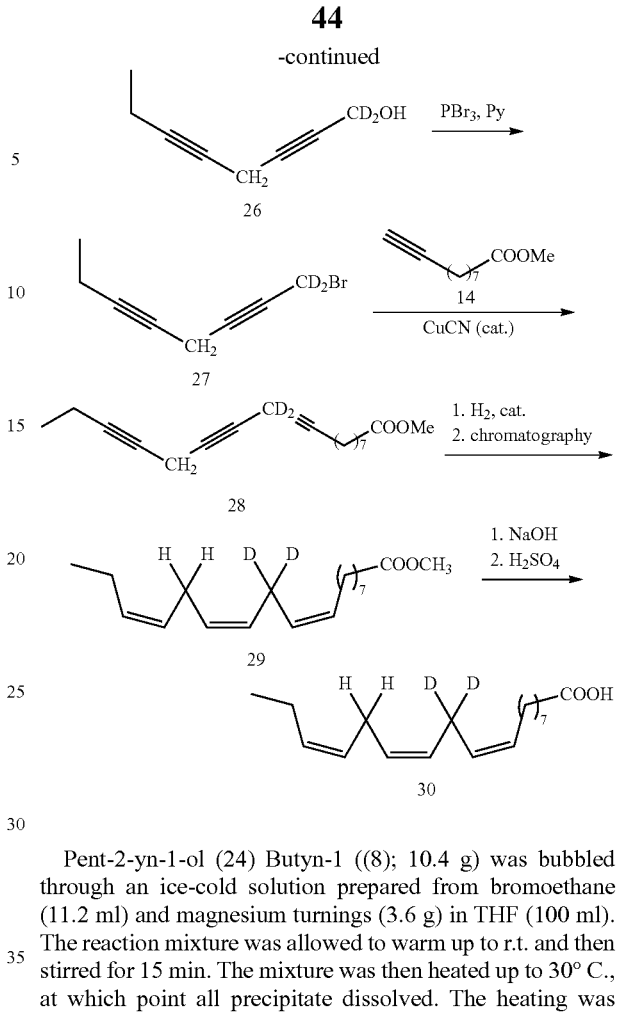

Pent-2-yn-1-ol (24) Butyn-1 ((8); 10.4 g) was bubbled through an ice-cold solution prepared from bromoethane (11.2 ml) and magnesium turnings (3.6 g) in THF (100 ml). The reaction mixture was allowed to warm up to r.t. and then stirred for 15 min. The mixture was then heated up to 30° C., at which point all precipitate dissolved. The heating was removed and the mixture stirred for another 30 min, and then paraform (3 g) was added in one portion. The reaction mixture was refluxed for 3 h (all paraform dissolved), then cooled to r.t., poured into a mixture of crushed ice (80 g) and 8 ml conc. H$_2$SO$_4$, and extracted with diethyl ether. The organic phase was washed with saturated NaHCO$_3$ and NaCl, and dried over Na$_2$SO$_4$. The solvent was removed on a rotavap, and the residue (7.56 g; 90%) was used without further purification. HRMS, m/z calculated for C$_5$H$_8$O: 84.0575; found: 84.0583.

1-Bromo-pent-2-yne (25) To a solution of (24) (11.7 g) and pyridine (2.66 ml) in dry diethyl ether (34 ml), 5.2 ml of PBr$_3$ in 5 ml diethyl ether was added dropwise with stirring over 30 min at −10° C. under argon. The reaction mixture was allowed to gradually warm up to r.t. over 1 h. A catalytic amount of hydroquinone was added, and the mixture was then refluxed for 4.5 h. The reaction mixture was then cooled down to −10° C. and 35 ml of cold water was added. When the residue dissolved, saturated NaCl (35 ml) and diethyl ether (30 ml) were added, and the organic layer was separated. The aqueous fraction was washed with diethyl ether (2×15 ml), and the combined organic fractions were washed with NaCl (2×400 ml) and dried over MgSO$_4$. The solvent was removed at atmospheric pressure, and then under reduced pressure (25 mm Hg), the 60-90° C. fraction was collected. Yield: 11.1 g (84%). HRMS, m/z calculated for C$_5$H$_7$Br: 145.9731; found: 144.9750, 146.9757.

1,1-Dideutero-octa-2,5-diyn-1-ol (26) was synthesized as described for (12) with 87% yield. HRMS, m/z calculated for C$_8$H$_8$D$_2$O: 124.0855; found: 124.0868. IR(CCl$_4$):

$\tilde{v}$=3622 cm$^{-1}$. $^1$H NMR (CDCl$_3$, δ): 2.65 (m, 2H, CH$_2$), 2.4 (m, 1H, OH), 2.1 (q, 2H, CH$_2$), 1.09 (t, 3H, CH$_3$).

1,1-Dideutero-1-bromo-octa-2,5-diyne (27) was synthesized as described for (3), except all solvent was removed on a rotavap. The product was purified by distillation at reduced pressure. Yield: 86% (b.p. 100-105° C. at 4 mm Hg). HRMS, m/z calculated for C$_8$H$_7$D$_2$Br: 186.0011; found: 184.9948, 187.9999. IR(CCl$_4$): $\tilde{v}$=2255 cm$^{-1}$. $^1$H NMR (CDCl$_3$, δ): 2.66 (m, 2H, CH$_2$), 2.1 (q, 2H, CH$_2$), 1.09 (t, 3H, CH$_3$).

11,11-Dideutero-octadeca-8,12,15-triynoic acid methyl ester (28) was synthesized as described for (5). The product obtained from 7.1 g CuI, 5.66 g NaI, 7.65 g K$_2$CO$_3$, 3.55 g of bromide (27), 3.47 g of methyl ester (14) and 30 ml of anhydrous DMF, was purified by CC (25:1 hexane:EtOAc) to give 3.7 g of the title compound. HRMS, m/z calculated for C$_{19}$H$_{24}$D$_2$O$_2$: 288.2056; found: 288.2069. $^1$H NMR (CDCl$_3$, δ): 3.7 (s, 3H, OCH$_3$), 3.15 (br. s, 2H, CH$_2$), 2.35 (m, 2H, CH$_2$), 2.17 (m, 4H, CH$_2$), 1.61 (m, 2H, CH$_2$), 1.48 (m, 2H, CH$_2$), 1.35 (m, 6H, CH$_2$), 1.11 (t, 3H, CH$_3$).

11,11-Dideutero-cis,cis,cis-octadeca-8,12,15-trienoic acid methyl ester (29) was synthesized as described for the linoleic acid derivative (6). For a reduction of 3.7 g of (28), 2.16 g of nickel acetate tetrahydrate and 2.62 ml ethylenediamine was used. The product was purified on AgNO$_3$-impregnated silica gel as described for (6) to give 1.5 g. HRMS, m/z calculated for C$_{19}$H$_{30}$D$_2$O$_2$: 294.2526; found: 294.2402. IR(CCl$_4$): $\tilde{v}$=1740 cm$^{-1}$. $^1$H NMR (CDCl$_3$, δ): 5.37 (m, 6H, CH-double bond), 3.6 (s, 3H, OCH$_3$), 2.82 (m, 2H, CH$_2$), 2.33 (t, o=7.5 Hz, 2H, CH$_2$), 2.09 (m 4H, CH$_2$), 1.62 (m, 2H, CH$_2$), 1.33 (m, 8H, CH$_2$), 0.97 (t, J=7.5 Hz, 3H, CH$_3$). $^{13}$C NMR (CDCl$_3$, δ): 174.1, 131.9, 130.2, 128.2, 128.1, 127.7, 126.9, 51.3, 34.0, 29.5, 29.1, 29.04, 29.02, 27.1, 25.5, 24.9, 20.5, 14.2.

11,11-Dideutero-cis,cis,cis-octadeca-8,12,15-trienoic acid (30) To a solution of (29) (1.5 g, 5.1 mmol) in MeOH (7.5 ml), a solution of KOH (1.5 g, 27 mmol) in water (3 ml) was added in one portion. The reaction mixture was then processed as described for (17) to yield 0.9 g of the title acid. IR(CCl$_4$): $\tilde{v}$=1741, 1711 cm$^{-1}$. $^1$H NMR (CDCl$_3$, δ): 11.2 (br s, 1H, COOH), 5.37 (m, 6H, CH-double bond), 2.83 (m, 2H, CH$_2$), 2.35 (t, J=7.5 Hz, 2H, CH$_2$), 2.06 (m 4H, CH$_2$), 1.63 (m, 2H, CH$_2$), 1.32 (m, 8H, CH$_2$), 0.97 (t, J=7.5 Hz, 3H, CH$_3$). $^{13}$C NMR (CDCl$_3$, δ): 180.4, 131.9, 130.2, 128.3, 128.1, 127.6, 127.1, 34.1, 29.5, 29.1, 29.03, 28.98, 27.2, 25.5, 24.6, 20.5, 14.2.

Example 5

Synthesis of 8,8-D$_2$-Linoleic Acid Methyl Ester

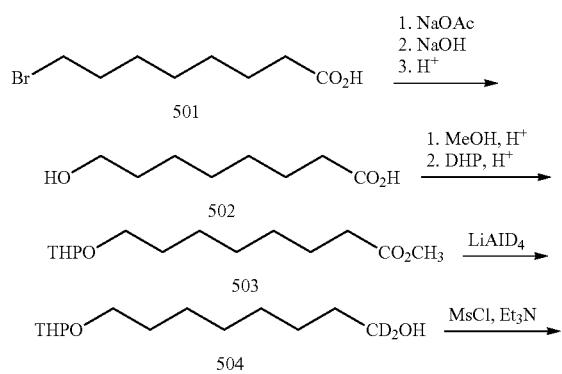

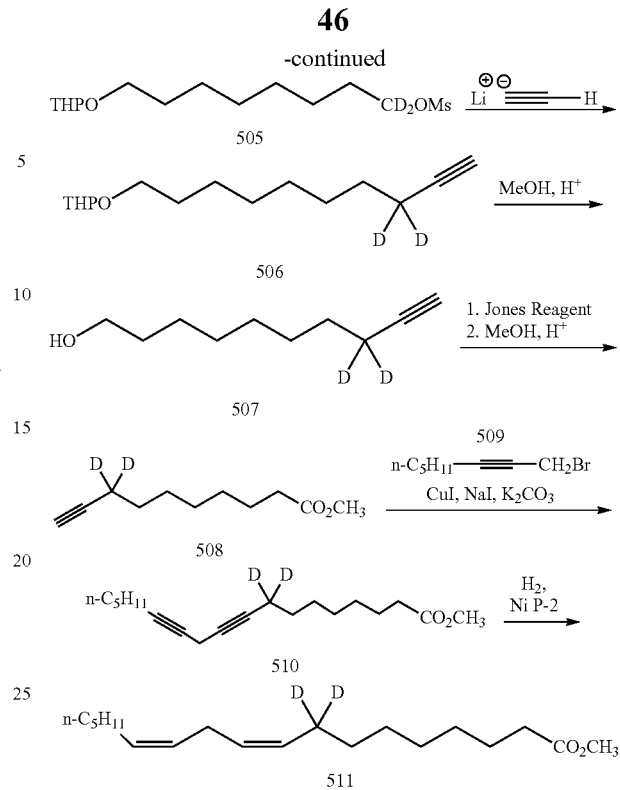

8-Hydroxyoctanoic acid (502). A solution of 8-bromo-caprylic acid (501, 37.5 g, 168 mmol), anhydrous sodium acetate (60.0 g, 732 mmol) and sodium iodide (1.0 g, 6.7 mmol) in DMF (200 ml) was stirred at 110-120° C. for 8 h. The reaction mixture was cooled to r.t., a solution of potassium hydroxide (28 g, 0.5 mol) in water (150 ml), was added, and the mixture was stirred at 100° C. for another hour. The reaction mixture was cooled to r.t. and poured into slurry of ice and concentrated sulfuric acid (45 ml). The solution obtained was saturated with NaCl and extracted (9×150 ml) with a mixture of EtOAc and petroleum ether (1:1). Combined organic fractions were washed twice with saturated NaCl and dried over Na$_2$SO$_4$. The solvent was evaporated to give 26.5 g (98%) of the product which was used without further purification. A small amount of the product was further purified by CC on silica (eluent: petroleum ether:EtOAc=2:1) and characterized. $^1$H NMR (400 MHz, CDCl$_3$) δ 1.27-1.39 (m, 6H), 1.50-1.68 (m, 4H), 2.32 (t, 2H, J=7.5 Hz), 3.62 (t, 2H, J=6.5 Hz), 6.87 (br. s., 2H).

Methyl 8-(tetrahydro-2H-pyran-2-yloxy)octanoate (503). 8-Hydroxyoctanoic acid (502; 26.3 g, 164 mmol) was dissolved in methanol (500 ml) containing acetyl chloride (3.5 ml). The reaction mixture was refluxed for 5 h and the solvent removed in vacuo. To the residue dissolved in CH$_2$Cl$_2$ (200 ml), 3,4-dihydro-2H-pyran (29 ml, 318 mmol) was added, and the reaction mixture was refluxed for 20 min. Upon addition of 5 ml of triethylamine, the solvent was removed in vacuo, and the residue was dissolved in petroleum ether (100 ml) and washed with water. The organic layer was flush-purified on a small silica column (silica, 100 ml; eluent: from petroleum ether to petroleum ether:EtOAc=20:1). The work-up yielded 38.2 g (90%) of the product which was used without further purification. A small amount of the product was further purified by CC on silica (eluent: petroleum ether: EtOAc=15:1) and characterized. IR(CCl$_4$): $\tilde{v}$=1741 cm$^{-1}$. $^1$H NMR (400 MHz, CDCl$_3$) δ 1.20-1.36 (m, 6H), 1.40-1.82 (m, 10H), 2.23 (t, 2H, J=7.5

Hz), 3.30 (dt, 1 H, J=9.5 Hz, 6.5 Hz), 3.39-3.46 (m, 1H), 3.59 (s, 3H), 3.65 (dt, 1 H, J=9.5 Hz, 7.0 Hz), 3.76-3.83 (m, 1H), 4.47-4.52 (m, 1H).

[1,1-$D_2$]-8-(tetrahydro-2H-pyran-2-yloxy)octan-1-ol (504). To a stirred solution of ester (503) (37.5 g, 145 mmol) in diethyl ether (100 ml) in an ice bath, a suspension of LiAlD$_4$ (4.0 g, 95 mmol) in diethyl ether (300 ml) was added drop wise over 1 h. To the cold reaction mixture, water (4 ml), 15% NaOH (4 ml) and water (12 ml) were added with stirring. The precipitate was filtered and washed with ethyl ether. Evaporation in vacuo gave 33.5 g (99%) of the product. A small amount of the product was further purified by CC on silica (eluent: petroleum ether: EtOAc=10:1) and characterized. IR(CCl$_4$): $\tilde{v}$=3638, 3499 cm$^{-1}$. $^1$H NMR (400 MHz, CDCl$_3$) δ 1.22-1.33 (m, 8H), 1.42-1.56 (m, 8H), 1.61-1.69 (m, 1H), 1.71-1.80 (m, 1H), 2.38 (br. s., 1H), 3.31 (dt, 1 H, J=9.5 Hz, 6.5 Hz), 3.40-3.46 (m, 1H), 3.66 (dt, 1 H, J=9.5 Hz, 7.0 Hz), 3.76-3.84 (m, 1H), 4.49-4.53 (m, 1H). $^{13}$C NMR (100 MHz, CDCl$_3$) δ 19.5, 25.3, 25.5, 26.0, 29.2, 29.3, 29.5, 30.6, 32.4, 62.1, 67.5, 98.7.

[1,1-$D_2$]-8-(tetrahydro-2H-pyran-2-yloxy)octyl methanesulfonate (505). To a solution of alcohol (504) (33.4 g, 144 mmol) and triethylamine (45 ml, 323 mmol) in diethyl ether (300 ml) at 0° C., a solution of MsCl (14.2 ml, 183 mmol) in diethyl ether (100 ml) was added drop wise over 1 h with stirring. The reaction mixture was warmed up to r.t. and treated with water. The organic phase, combined with washings (2×50 ml) of the aqueous phase with Et$_2$O, was washed twice with saturated NaCl, dried over Na$_2$SO$_4$, and decanted. This was flush-purified on a small silica column (silica, 100 ml; petroleum ether:EtOAc=10:1). The work-up yielded 43.7 g (98%) of methanesulfonate (505). IR(CCl$_4$): $\tilde{v}$=1739 cm$^{-1}$. $^1$H NMR (400 MHz, CDCl$_3$) δ 1.26-1.41 (m, 8H), 1.44-1.59 (m, 6H), 1.63-1.84 (m, 4H), 2.97 (s, 3H), 3.32 (dt, 1 H, J=9.5 Hz, 6.5 Hz), 3.42-3.50 (m,1H), 3.69 (dt, 1 H, J=9.5 Hz, 7.0 Hz) 3.78-3.86 (m, 1H), 4.52-4.56 (m, 1H). $^{13}$C NMR (100 MHz, CDCl$_3$) δ 19.6, 25.2, 25.4, 26.0, 28.7, 28.8, 29.1, 29.5, 30.7, 37.2, 62.3, 67.4, 98.8.

2-([8,8-$D_2$]-dec-9-yne-1-yloxy)tetrahydro-2H-pyran (506). Methanesulfonate (505) (43.5 g, 140 mmol) in DMSO (100 ml) was added dropwise with stirring over 1 h to a suspension of a ethylenediamine-lithium acetylenide complex (70 g, 0.76 mol) in DMSO (200 ml), and then the mixture was stirred for 90 min. Reaction mixture was poured on ice, extracted (Et$_2$O, 3×150 ml), dried over Na$_2$SO$_4$ and evaporated. This was flush-purified on a small silica column (silica, 100 ml; petroleum ether). Removal of solvent (rotavap) gave 25.3 g (75%) of the product. A small amount of the product was further purified by CC on silica (eluent: petroleum ether: EtOAc=25:1) and characterized. IR(CCl$_4$): $\tilde{v}$=3314 cm$^{-1}$. $^1$H NMR (400 MHz, CDCl$_3$) δ 1.21-1.38 (m, 8H), 1.42-1.57 (m, 8H), 1.62-1.70 (m, 1H), 1.73-1.83 (m, 1H), 1.89 (s, 1H), 3.32 (d.t., 1 H, J=9.5 Hz, 6.5 Hz), 3.42-3.50 (m, 1H), 3.68 (d.t., 1 H, J=9.5 Hz, 7.0 Hz) 3.78-3.86 (m, 1H), 4.51-4.54 (m, 1H). $^{13}$C NMR (100 MHz, CDCl$_3$) δ 19.6, 25.4, 26.1, 28.1, 28.5, 28.9, 29.2, 29.6, 30.6, 30.7, 62.1, 67.5, 68.0, 98.7.

[8,8-$D_2$]-dec-9-yne-1-ol (507). Ether (506) (25 g, 104 mmol) was dissolved in methanol (300 ml) containing pyridinium para-toluenesulfonate (0.2 g). Reaction mixture was refluxed for 3 h, quenched with Et$_3$N (1 ml), the solvent removed in vacuo, the residue dissolved in petroleum ether and filtered through a small amount of silica gel. The solvent was evaporated to give 15.4 g (95%) of the product. A small amount of the product was further purified by CC on silica (eluent: petroleum ether: EtOAc=15:1) and characterized. IR(CCl$_4$): $\tilde{v}$=3638, 3508, 3314 cm$^{-1}$. $^1$H NMR (400 MHz, CDCl$_3$) δ 1.22-1.40 (m, 8H), 1.42-1.56 (m, 4H), 1.91 (s, 1H), 2.29 (br. s., 1H), 3.59 (t, J=6.5 Hz, 2H). $^{13}$C NMR (100 MHz, CDCl$_3$) δ 25.6, 28.1, 28.5, 29.0, 29.2, 32.6, 62.8, 68.1, 84.6.

[8,8-$D_2$]-methyl dec-9-ynoate (508). To a solution of chromium trioxide (24 g, 0.24 mol) and concentrated sulfuric acid (21 ml) in water (100 ml) in a two-neck round bottom flask on water bath at 30° C. with stirring, a solution of alcohol (507) (15.5 g, 99 mmol) in acetone (150 ml) was added dropwise over 90 min. Upon addition, the reaction mixture was stirred for another 15 min, and the excess of oxidizer was quenched with isopropyl alcohol. The mixture was poured into cold water and extracted with diethyl ether (5×50 ml). Combined organic fractions were washed with saturated NaCl, dried over Na$_2$SO$_4$, filtered, and the solvent removed in vacuo. The residue was dissolved in methanol (200 ml) and upon addition of concentrated sulfuric acid (1 ml) refluxed for 90 min. The acid was quenched with triethylamine (6.5 ml, 47 mmol), the solvent removed in vacuo, and the residue purified by CC on silica (eluent: petroleum ether: EtOAc=50:1) to give 12.6 g (69% counting per alcohol (507)) of ester (508). and characterized. IR(CCl$_4$): $\tilde{v}$=3314, 1740 cm$^{-1}$. $^1$H NMR (400 MHz, CDCl$_3$) δ 1.19-1.38 (m, 6H), 1.41-1.48 (m, 2H), 1.51-1.61 (m, 2H), 1.88 (s, 1H), 2.25 (t, J=7.5 Hz, 2H), 3.60 (s, 3H). $^{13}$C NMR (100 MHz, CDCl$_3$) δ 24.7, 28.0, 28.3, 28.6, 28.8, 33.9, 51.3, 68.1, 84.4, 174.0.

[8,8-$D_2$]-methyl octadeca-9,12-diynoate (510). To DMF (20 ml) were added with stirring CuI (3.9 g, 20 mmol), followed by NaI (3.1 g, 21 mmol), K$_2$CO$_3$ (4.2 g, 30 mmol), ester (508) (1.9 g, 10.3 mmol), and bromide (509) (2.04 g, 10.8 mmol, synthesized as described in [2]). The reaction mixture was stirred at r.t. for 12 h. Saturated aqueous ammonium chloride (20 ml) was added to the mixture, followed by saturated NaCl (15 ml). The precipitate and the aqueous phase were washed with petroleum ether. The combined organic fractions were washed with saturated sodium chloride, dried over Na$_2$SO$_4$ and evaporated in vacuo. The residue was purified by CC on silica (eluent: petroleum ether: EtOAc=50:1) to give 2.47 g (82%) of the product. $^1$H NMR (400 MHz, CDCl$_3$) δ 0.86 (t, J=7.0 Hz, 3H), 1.22-1.36 (m, 10H), 1.40-1.50 (m, 4H), 1.55-1.64 (m, 2H), 2.09-2.15 (m, 2H), 2.28 (t, J=7.5 Hz, 2H), 3.09 (t, J=2.5 Hz, 2H), 3.64 (s, 3H). $^{13}$C NMR (100 MHz, CDCl$_3$) δ 9.6, 13.9, 18.6, 22.1, 24.8, 28.3, 28.4, 28.5, 28.7, 28.9, 31.0, 34.0, 51.4, 74.4, 74.5, 80.2, 80.4, 174.2.

[8,8-$D_2$]-octadeca-9,12-dienoate (511). A suspension of finely ground Ni(Ac)$_2$×4H$_2$O (0.8 g, 3.2 mmol) in 96% ethanol (25 ml) was heated with stirring to 50-60° C. until the salt was fully dissolved. The system was flushed with hydrogen, and then a solution of NaBH$_4$ (3.4 ml; obtained by 15 min stirring of NaBH$_4$ suspension (0.53 g, 14 mmol) in ethanol (12 ml) followed by filtering through a fine filter) was added over 10 min. Evolvement of hydrogen was observed. In 15-20 min, ethylenediamine (1.65 ml, 25 mmol) was added to the reaction mixture in one portion with stirring, followed by the solution of (510) (2.4 g, 8.2 mmol) in ethanol (10 ml). The reaction mixture was vigorously stirred under hydrogen until there was no further absorption of hydrogen, and then treated with acetic acid (2.3 ml), water (10 ml), and extracted with petroleum ether:EtOAc (5:1). Combined organic fractions were washed with 10% sulfuric acid (10 ml), then with saturated sodium chloride, dried over Na$_2$SO$_4$, and the solvent was removed in vacuo. The residue was purified by CC on silica (eluent: petroleum ether: EtOAc=50:1) to give 2.33 g (96%) of the product. The product was then purified again by CC on silica impregnated with 20% AgNO$_3$ (eluent: petroleum ether to petroleum ether:EtOAc=2:1). 1.75 g (72%) of the product was obtained (97% purity by GC). $^1$H NMR (400 MHz, CDCl$_3$) δ 0.88 (t, J=7.0 Hz, 3H), 1.20-1.40 (m, 14H), 1.55-1.66 (m, 2H), 1.97-2.09 (m, 2H), 2.29 (t, J=7.5 Hz, 2H), 2.72-2.79 (m, 2H), 3.66 (s, 3H), 5.28-5.41 (m, 4H). $^{13}$C NMR (100 MHz, CDCl$_3$) δ 14.0, 22.5, 24.9, 25.6, 27.2, 29.00, 29.08, 29.13, 29.3, 29.4, 31.5, 34.1, 51.4, 127.9, 128.0, 129.9, 130.2, 174.2.

Example 6

Synthesis of II-D-Linoleic Acid

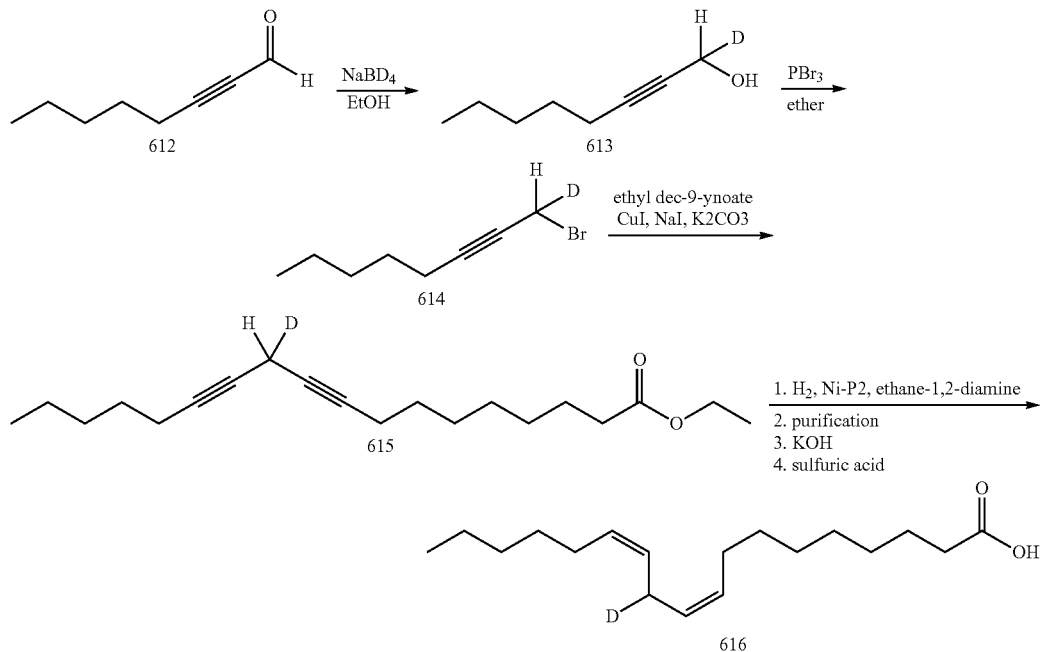

oct-2-yn-1-ol (13). To a solution of oct-2-ynal [See Corey, E. J.; Schmidt, G. *Tetrahedron Lett.* 1979, 20, 399; Meyer, M. P.; Klinman, J. P. *Tetrahedron Lett.* 2008, 49, 3600] ((612); 1.00 g, 8.1 mmol)) in ethanol (15 ml) cooled to 0° C., 0.11 g (2.6 mmol) of NaBD$_4$ was added in portions over 5 min. Upon addition, the solution was stirred for another 30 min, diluted with water (100 ml), and then extracted with Et$_2$O (4×20 ml). The combined organic fractions were washed with saturated NaCl, dried (Na$_2$SO$_4$), and the solvent was removed at reduced pressure. Alcohol 613 (0.85 g, 83%) was purified by column chromatography (silica gel, petroleum ether:EtOAc (15:1)). $^1$H NMR (400 MHz, CDCl$_3$) δ 0.88 (t, J=7.0 Hz, 3H), 1.32 (m, 4H, CH$_2$), 1.49 (quint, J=7.0 Hz, 2H, CH$_2$), 1.81 (br s, 1H, OH), 2.19 (td, J=7.0 Hz, 2.0 Hz, 2H, CH$_2$), 4.22 (m, 1H, CHD).

1-bromooct-2-yne (614) was synthesized as described in [See Hill, Sh.; Hirano, K.; Shmanai, V. V.; Marbois, B. N.; Vidovic, D.; Bekish, A. V.; Kay, B.; Tse, V.; Fine, J.; Clarke, C. F.; Shchepinov, M. S. *Free Radic. Biol. Med.*, 2011, 50 (1), 130-138.]. $^1$H NMR (400 MHz, CDCl$_3$) δ 0.89 (t, J=7.0 Hz, 3H, CH$_3$), 1.32 (m, 4H, CH$_2$), 1.50 (quint, J=7.0 Hz, 2H, CH$_2$), 2.22 (td, J=7.0 Hz, 2.0 Hz, 2H, CH$_2$), 3.91 (m, 1H, CHD).

[11-$^2$H]-ethyl octadeca-9,12-diynoate (615). was synthesized as described [See Meyer, M. P.; Klinman, J. P. *Tetrahedron Lett.* 2008, 49, 3600; Hill, Sh.; Hirano, K.; Shmanai, V. V.; Marbois, B. N.; Vidovic, D.; Bekish, A. V.; Kay, B.; Tse, V.; Fine, J.; Clarke, C. F.; Shchepinov, M. S. *Free Radic. Biol. Med.*, 2011, 50 (1), 130-138]. CuI (2 g, 10.5 mmol), NaI (1.58 g, 10.5 mmol), K$_2$CO$_3$ (2.1 g, 15 mmol), ethyl dec-9-ynoate (1.02 g, 5.2 mmol) and bromide 614 (1.03 g, 5.4 mmol) were added to DMF (10 ml) with stirring. The reaction mixture was stirred at RT for 12 h, then NH$_4$Cl (10 ml) and NaCl (8 ml) were added and the stirring continued for another 5 min. The precipitate was separated and washed with petroleum ether. Organic layers were separated, and the aqueous layer was extracted with petroleum ether. The combined organic fractions were washed with saturated NaCl, dried (Na$_2$SO$_4$), and the solvent was removed at reduced pressure. Column chromatography (silica gel, petroleum ether:EtOAc (15:1)) yielded 1.29 g (81%) of the product. $^1$H NMR (400 MHz, CDCl$_3$) δ 0.89 (t, J=7.0 Hz, 3H, CH$_3$), 1.25 (t, J=7.0 Hz, 3H, CH$_3$CH$_2$O), 1.31 (m, 10H, CH$_2$), 1.49 (m, 4H, CH$_2$), 1.61 (m, 2H, CH$_2$), 2.15 (td, J=7.0 Hz, 2.0 Hz, 2H, CH$_2$ in propargylic position), 2.28 (t, J=7.5 Hz, 2H, CH$_2$COOEt), 3.10 (m, 1H, CHD), 4.12 (q, J=7.0 Hz, 2H, OCH$_2$CH$_3$). $^{13}$C NMR (100 MHz, CDCl$_3$) δ 9.6 (t, J=19.0 Hz), 13.9, 14.1, 18.56, 18.57, 22.1, 24.8, 28.4, 28.6, 28.7, 28.9, 28.9, 31.0, 34.2, 60.0, 74.3, 74.5, 80.2, 80.3, 173.7.

[11-$^2$H]-linoleic acid (616) A suspension of triturated nickel acetate tetrahydrate (0.4 g, 1.6 mmol) in 96% ethanol (12 ml) was heated at 50-60° C. with stirring until the salt dissolved. The system was flushed with hydrogen, and then 1.7 ml of NaBH$_4$ (obtained by 15-min stirring of a NaBH$_4$ suspension (0.27 g, 14 mmol) in ethanol (6 ml) followed by filtering) was added over 10 min, with some gas bubbles evolving. In 15-20 min, ethylenediamine (0.8 ml, 12 mmol) was added in one portion with stirring, followed in 5 min by a solution of diyne 615 (1.2 g, 3.9 mmol) in ethanol (5 ml). The reaction mixture was stirred vigorously until there was no more absorption of hydrogen, and then treated with acetic acid (1.2 ml), water (10 ml) and extracted with a mixture of petroleum ether and EtOAc (5:1). The combined organic fractions were washed with 10% sulphuric acid (5 ml) and then with saturated NaCl, dried (Na₂SO₄), and the solvent was removed at reduced pressure. Column chromatography (silica gel, petroleum ether:EtOAc (50:1)) yielded 1.14 g (94%) of the product. The product was additionally purified [3] on a silver nitrate-impregnated silica (20% AgNO₃), with petroleum ether:EtOAc (2:1) as eluent to give 0.73 g (60%) of the linoleic acid ethyl ester (>96% purity by GC; GC-MS: MW 309 (GC-MS for a control non-deuterated linoleic acid ethyl ester: MW 308). $^1$H NMR (400 MHz, CDCl₃) δ 0.89 (t, J=7.0 Hz, 3H, CH₃), 1.25 (t, J=7.0 Hz, 3H, CH₃CH₂O), 1.30 (m, 14H, CH₂), 1.61 (m, 2H, CH₂), 2.04 (m, 2H), 2.28 (t, J=7.5 Hz, 2H, CH₂COOEt), 2.74 (m, 1H, CHD), 4.12 (q, J=7.0 Hz, 2H, OCH₂CH₃), 5.34 (m, 4H, CH=CH). $^{13}$C NMR (100 MHz, CDCl₃) δ 14.1, 14.2, 22.6, 25.0, 25.3 (t, J=19.5 Hz), 27.17, 27.19, 29.08, 29.09, 29.14, 29.3, 29.6, 31.5, 34.4, 60.1, 127.8, 128.0, 130.0, 130.2, 173.9.

To obtain the free [11-$^2$H]-linoleic acid (616), to the solution of the linoleic acid ethyl ester (0.704 g, 2.3 mmol) in ethanol (10 ml) a solution of KOH (0.4 g, 7.1 mmol) in water (0.8 ml) was added. The mixture was stirred at 50° C. for 10 min and then diluted with water (20 ml), treated with 10% solution of sulphuric acid (5 ml) and extracted with Et₂O (4×20 ml). The combined organic fractions were washed with saturated NaCl, dried over Na₂SO₄, and the solvent was removed at reduced pressure. The residue was flushed through a small volume of silica gel (2 ml; eluent: petroleum ether:EtOAc (2:1)) and the solvent removed in vacuo to yield 0.629 g (98%) of the indicated acid 616. $^1$H NMR (400 MHz, CDCl₃) δ 0.88 (t, J=7.0 Hz, 3H, CH₃), 1.30 (m, 14H, CH₂), 1.60 (m, 2H, CH₂), 2.03 (m, 4H, CH₂), 2.33 (t, J=7.5 Hz, 2H, CH₂COOEt), 2.74 (m, 1H, CHD), 5.32 (m, 4H, CH=CH), 11.6 (br s, 1H, COOH). $^{13}$C NMR (100 MHz, CDCl₃) δ 14.1, 22.6, 24.6, 25.3 (t, J=19.0 Hz), 27.16, 27.18, 29.00, 29.05, 29.12, 29.3, 29.6, 31.5, 34.0, 127.8, 128.0, 130.0, 130.2, 180.1.

Example 7

Synthesis of [11-$^{13}$C]-Linoleic Acid

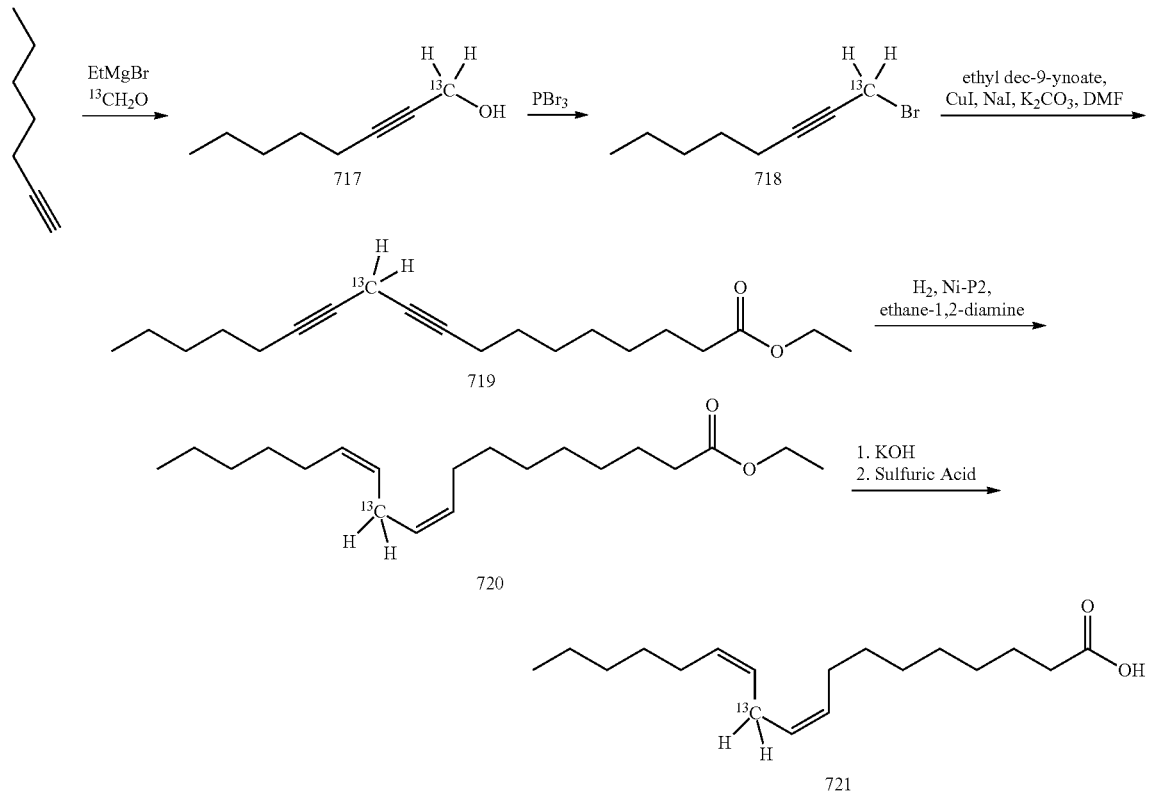

[1-$^{13}$C]-oct-2-yn-1-ol (717). The title compound has been synthesized according to the earlier described protocols (Hill, Sh.; Hirano, K.; Shmanai, V. V.; Marbois, B. N.; Vidovic, D.; Bekish, A. V.; Kay, B.; Tse, V.; Fine, J.; Clarke, C. F.; Shchepinov, M. S. Free Radic. Biol. Med., 2011, 50 (1), 130-138) using $^{13}$C-paraform, and used without further purification. $^1$H NMR (CDCl₃, δ): 4.22 (д, J=148 Hz, 2H), 2.18 (td, J₁=7.0, J₂=1 Hz, 2H), 1.91 (br s, 1H), 1.47 (quint, J=7.0 Hz, 2H), 1.31 (m, 4H), 0.87 (t, J=7.0 Hz, 3H).

[1-$^{13}$C]-1-bromooct-2-yne (718) was synthesized as described in (Hill, Sh.; Hirano, K.; Shmanai, V. V.; Marbois, B. N.; Vidovic, D.; Bekish, A. V.; Kay, B.; Tse, V.; Fine, J.; Clarke, C. F.; Shchepinov, M. S. Free Radic. Biol. Med., 2011, 50 (1), 130-138). Yield: 82% starting from $^{13}$C-paraform (per two steps). $^1$H NMR (CDCl₃, δ): 3.93 (dt, J₁=158 Hz, J₂=2 Hz, 2H), 2.23 (m, 2H), 1.50 (m, 2H), 1.33 (m, 4H), 0.89 (t, J=7 Hz, 3H).

[11-$^{13}$C]-ethyl octadeca-9,12-diynoate (719). was synthesized as previously described (See Meyer, M. P.; Klinman, J. P. Tetrahedron Lett. 2008, 49, 3600; Hill, Sh.; Hirano, K.; Shmanai, V. V.; Marbois, B. N.; Vidovic, D.; Bekish, A. V.; Kay, B.; Tse, V.; Fine, J.; Clarke, C. F.; Shchepinov, M. S. Free Radic. Biol. Med., 2011, 50 (1), 130-138). Yield: 93%. $^1$H NMR (CDCl₃, δ): 4.10 (q, J=7 Hz, 2H), 3.1 (dm, J=134

Hz, 2H), 2.27 (t, J=7.5 Hz, 2H), 2.13 (m, 4H), 1.60 (m, 2H), 1.47 (m, 4H), 1.3 (m, 10H), 1.24 (t, J=7 Hz, 3H), 0.88 (t, J=7.0 Hz, 3H).

[11-$^{13}$C]-linoleic acid ethyl ester (720) was synthesized as previously described (See Meyer, M. P.; Klinman, J. P. *Tetrahedron Lett.* 2008, 49, 3600; Hill, Sh.; Hirano, K.; Shmanai, V. V.; Marbois, B. N.; Vidovic, D.; Bekish, A. V.; Kay, B.; Tse, V.; Fine, J.; Clarke, C. F.; Shchepinov, M. S. *Free Radic. Biol. Med.*, 2011, 50 (1), 130-138). Yield: 56%. $^1$H NMR (CDCl$_3$, δ): 5.34 (m, 4H), 4.12 (q, J=7 Hz, 2H), 2.77 (dm, J=126 Hz, 2H), 2.28 (t, J=7.5 Hz, 2H), 2.04 (m, 4H), 1.61 (m, 2H), 1.30 (m, 14H), 1.25 (t, J=7 Hz, 3H), 0.88 (t, J=7.0 Hz, 3H).

[11-$^{13}$C]-linoleic acid (721) was synthesized as previously described (See Meyer, M. P.; Klinman, J. P. *Tetrahedron Lett.* 2008, 49, 3600; Hill, Sh.; Hirano, K.; Shmanai, V. V.; Marbois, B. N.; Vidovic, D.; Bekish, A. V.; Kay, B.; Tse, V.; Fine, J.; Clarke, C. F.; Shchepinov, M. S. *Free Radic. Biol. Med.*, 2011, 50 (1), 130-138); yield 98%. $^1$H NMR (CDCl$_3$, δ): 10.5 (br s, 1H), 5.34 (m, 4H), 2.77 (dm, J=126 Hz), 2.33 (t, J=7.5 Hz, 2H), 2.03 (m, 4H), 1.60 (m, 2H), 1.30 (m, 14H), 0.88 (t, J=7.0 Hz, 3H).

Example 8

General Preparation of Esters A-D

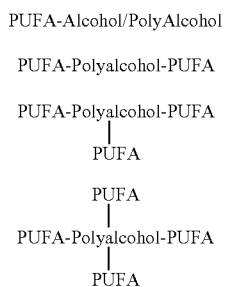

General Procedure for Compound A. Thionyl chloride (2 equivalents) is slowly added to a solution of PUFA (1 equivalent) in CHCl$_3$. The reaction mixture is heated to reflux for 1 hr, then it is allowed to cool to room temperature and the solvent is evaporated under reduced pressure to afford the carboxylic acid chloride derivative of the PUFA. The carboxylic acid chloride derivative is then dissolved in anhydrous pyridine and the alcohol (1 equivalent) dissolved in pyridine is slowly added (Note that the order of addition is reversed when the alcohol is a polyalcohol). Upon complete addition, the reaction mixture is allowed to stir at room temperature for 24 hr. The solvent is then removed under reduced pressure and the crude product is purified by column chromatography to afford Compound A.

11,11-Dideutero-cis,cis,cis-octadeca-8,12,15-trienoic acid (30); 14,14-Dideutero-cis,cis,cis-octadeca-8,12,15-trienoic acid (23); 11,11,14,14-Tetradeutero-cis,cis,cis-octadeca-8,12,15-trienoic acid (17); and 11,11-Dideutero-cis,cis-octadeca-9,12-dienoic acid (7) are each subjected to the above described procedure with the following alcohols: ethanol, glycerol, propylene glycol; glucose; 2-(2-ethoxyethoxy)ethanol; and estradiol to afford products corresponding to the general formula of Compound A.

General Procedure for Compound B. Thionyl chloride (2 equivalents) is slowly added to a solution of PUFA (1 equivalent) in CHCl$_3$. The reaction mixture is heated to reflux for 1 hr, then it is allowed to cool to room temperature and the solvent is evaporated under reduced pressure to afford the carboxylic acid chloride derivative of the PUFA. The carboxylic acid chloride derivative is then dissolved in anhydrous pyridine and the alcohol (Compound A, 1 equivalent) dissolved in pyridine is slowly added. Upon complete addition, the reaction mixture is allowed to stir at room temperature for 24 hr. The solvent is then removed under reduced pressure and the crude product is purified by column chromatography to afford Compound B.

The Compound A products that form from the condensation of 11,11-Dideutero-cis,cis,cis-octadeca-8,12,15-trienoic acid (30); 14,14-Dideutero-cis,cis,cis-octadeca-8,12,15-trienoic acid (23); 11,11,14,14-Tetradeutero-cis,cis,cis-octadeca-8,12,15-trienoic acid (17); and 11,11-Dideutero-cis,cis-octadeca-9,12-dienoic acid (7) with glycerol, propylene glycol; glucose; and estradiol are treated according to the above-described general procedure with 11,11-Dideutero-cis,cis,cis-octadeca-8,12,15-trienoic acid (30); 14,14-Dideutero-cis,cis,cis-octadeca-8,12,15-trienoic acid (23); 11,11,14,14-Tetradeutero-cis,cis,cis-octadeca-8,12,15-trienoic acid (17); and 11,11-Dideutero-cis,cis-octadeca-9,12-dienoic acid (7) as the PUFAs to afford products corresponding to the general formula of Compound B.

General Procedure for Compound C. Thionyl chloride (2 equivalents) is slowly added to a solution of PUFA (1 equivalent) in CHCl$_3$. The reaction mixture is heated to reflux for 1 hr, then it is allowed to cool to room temperature and the solvent is evaporated under reduced pressure to afford the carboxylic acid chloride derivative of the PUFA. The carboxylic acid chloride derivative is then dissolved in anhydrous pyridine and the alcohol (Compound B, 1 equivalent) dissolved in pyridine is slowly added. Upon complete addition, the reaction mixture is allowed to stir at room temperature for 24 hr. The solvent is then removed under reduced pressure and the crude product is purified by column chromatography to afford Compound C.

The Compound B products that form from the condensation of Compound A products with glycerol and glucose are treated according to the above-described general procedure with 11,11-Dideutero-cis,cis,cis-octadeca-8,12,15-trienoic acid (30); 14,14-Dideutero-cis,cis,cis-octadeca-8,12,15-trienoic acid (23); 11,11,14,14-Tetradeutero-cis,cis,cis-octadeca-8,12,15-trienoic acid (17); and 11,11-Dideutero-cis,cis-octadeca-9,12-dienoic acid (7) as the PUFAs to afford products corresponding to the general formula of Compound C.

General Procedure for Compound D. Thionyl chloride (2 equivalents) is slowly added to a solution of PUFA (1 equivalent) in CHCl$_3$. The reaction mixture is heated to reflux for 1 hr, then it is allowed to cool to room temperature and the solvent is evaporated under reduced pressure to afford the carboxylic acid chloride derivative of the PUFA. The carboxylic acid chloride derivative (4 equivalents) is then dissolved in anhydrous pyridine and the alcohol (1 equivalent) dissolved in pyridine is slowly added. Upon complete addition, the reaction mixture is allowed to stir at room temperature for 24 hr. The solvent is then removed under reduced pressure and the crude product is purified by column chromatography to afford Compound D.

The Compound C products that form from the condensation of Compound B products with glucose are treated according to the above-described general procedure with 11,11-Dideutero-cis,cis,cis-octadeca-8,12,15-trienoic acid (30); 14,14-Dideutero-cis,cis,cis-octadeca-8,12,15-trienoic acid (23); 11,11,14,14-Tetradeutero-cis,cis,cis-octadeca-8, 12,15-trienoic acid (17); and 11,11-Dideutero-cis,cis-octadeca-9,12-dienoic acid (7) as the PUFAs to afford products corresponding to the general formula of Compound D.

Example 9

Figure 2A:
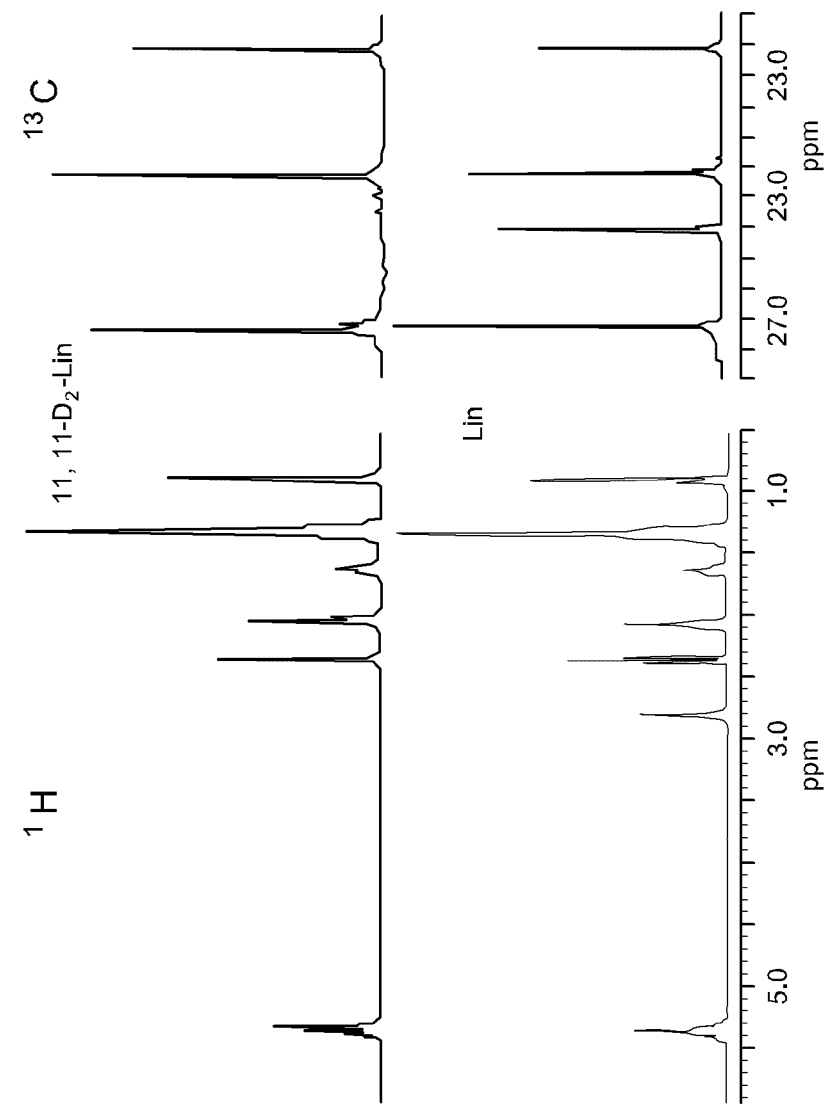
FIGS. 2A and 2B. $^1H$— and $^{13}C$—NMR analysis of deuterated PUFAs described in Examples 1-4.
Figure 2B:
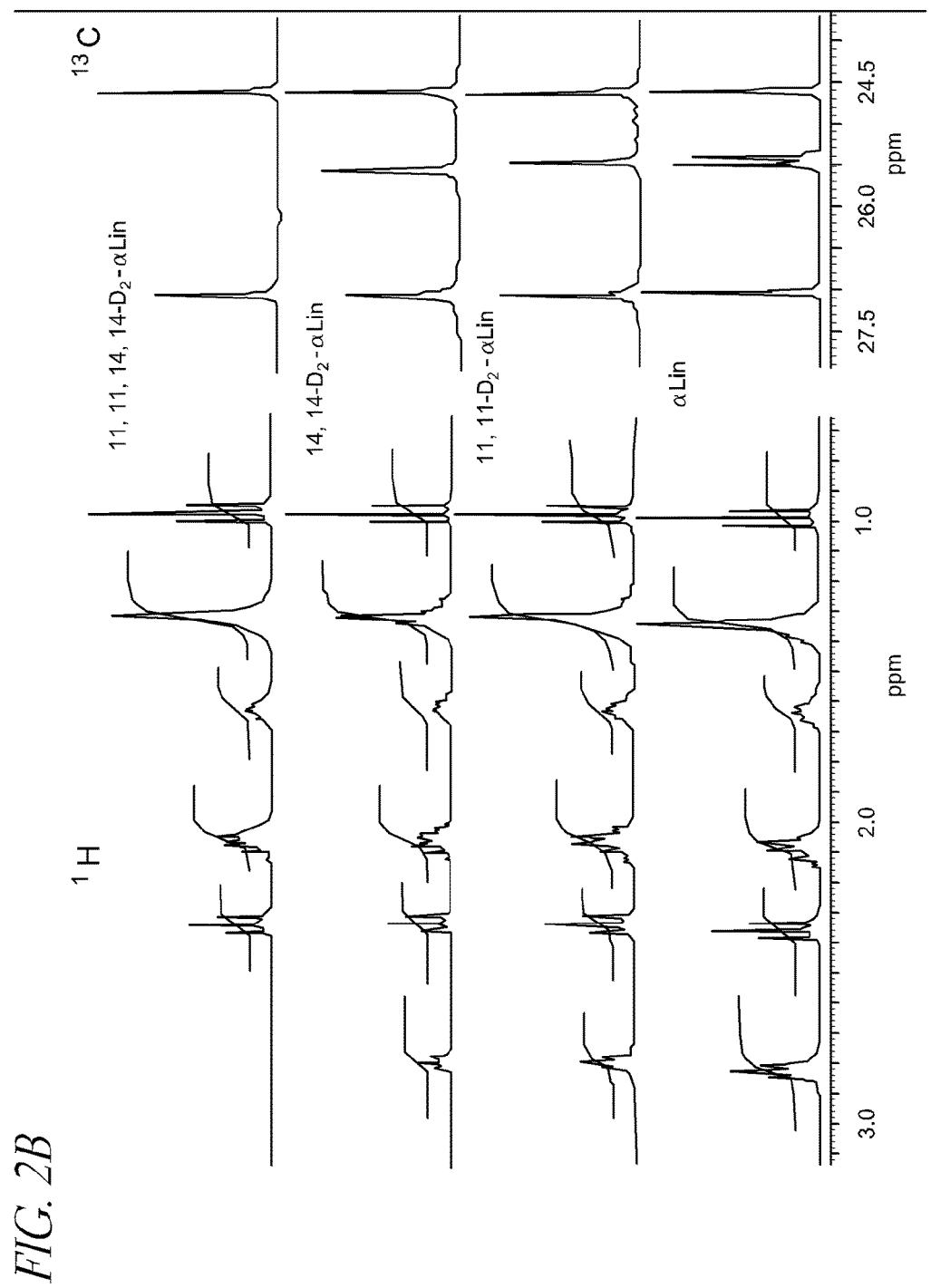

$^1$H- and $^{13}$C-NMR Analysis of Deuterated PUFAs Described in Examples 1-4 (FIG. 2)

Characteristic areas of $^1$H and $^{13}$C spectra, all values in ppm. (Panel A) Deuteration of Lin acid at pos. 11 is confirmed by the disappearance of peaks in $^1$H and $^{13}$C NMR spectra. Disappearance of the peak at $\delta_H$ 2.764 is expected due to absence of H atoms ($^1$H NMR). Disappearance of the peak at $\delta_C$ 25.5 in is due to combination of Nuclear Overhauser Effect, and splitting of this particular carbon atom into a quintet by two D atoms in the deuterated form of Lin acid. (Panel B) The $^1$H NMR spectrum shows that the H atoms at C11 and C14 positions of site-specifically deuterated αLnn coincide ($\delta_H$ 2.801) thus deuteration at either site (11,11-H$_2$, 14,14-D$_2$ or 11,11-D$_2$, 14,14-H$_2$) leads to a 50% decrease in integration of this peak, while deuteration of both sites (11,11,14,14-D$_4$) leads to the complete disappearance of the peak at $\delta_H$ 2.801. However, $^{13}$C NMR experiments can clearly distinguish between the three deuterated forms, as the observed peaks for C11 and C14 positions are separated by a small but detectable difference. Thus, deuteration at either C11 or C14 positions leads to disappearance of the peak at $\delta_C$ 25.68 or $\delta_C$ 25.60, respectively, while deuteration at both sites leads to disappearance of the two corresponding peaks.

Example 10

Isotope Reinforcement can Shut Down PUFA Peroxidation

Q-less yeast (coq mutants) provide an ideal system to assess in vivo autoxidation of fatty acids. Coenzyme Q (ubiquinone or Q) serves as a small lipophilic antioxidant as well as an electron shuttle in the respiratory chain of the mitochondrial inner membrane. Ten *S. cerevisiae* genes (COQ1-COQ10) are required for coenzyme Q biosynthesis and function, and the deletion of any results in respiratory deficiency (Tran U C, Clarke C F. *Mitochondrion* 2007; 7S,S62). It was shown that the coq yeast mutants are exquisitely sensitive to autoxidation products of PUFAs (Do T Q et al, *PNAS USA* 1996; 93:7534-7539; Poon W W, Do T Q, Marbois B N, Clarke C F. *Mol. Aspects. Med.* 1997; 18, s121). Although *S. cerevisiae* do not produce PUFAs (Paltauf F, Daum G. *Meth. Enzymol.* 1992; 209:514-522), they are able to utilize PUFAs when provided exogenously, allowing their content to be manipulated (Paltauf F, Daum G. Meth. Enzymol. 1992; 209:514-522). Less than 1% of Q-less (coq2, coq3, and coq5) yeast mutants are viable following a four hour treatment with linolenic acid (Do T Q et al, *PNAS USA* 1996; 93:7534-7539; Poon W W, Do T Q, Marbois B N, Clarke C F. *Mol. Aspects. Med.* 1997; 18, s121). In contrast, 70% of wild-type (the parental genetic background is strain W303-1B) cells subjected to this treatment remain viable. The Q-less yeast are also hypersensitive to other PUFAs that readily autoxidize (such as arachidonic acid), but behave the same as the wild-type parental strain to treatment with the monounsaturated oleic acid (Do T Q et al, *PNAS USA* 1996; 93:7534-7539). The hypersensitivity of the Q-less yeast mutants is not a secondary effect of the inability to respire, because cor1 or atp2 mutant yeast (lacking either the bc1 complex or the ATP synthase, respectively) show wild-type resistance to PUFA treatment (Do T Q et al, *PNAS USA* 1996; 93:7534-7539; Poon W W, Do T Q, Marbois B N, Clarke C F. *Mol. Aspects. Med.* 1997; 18, s121).

Figure 3:
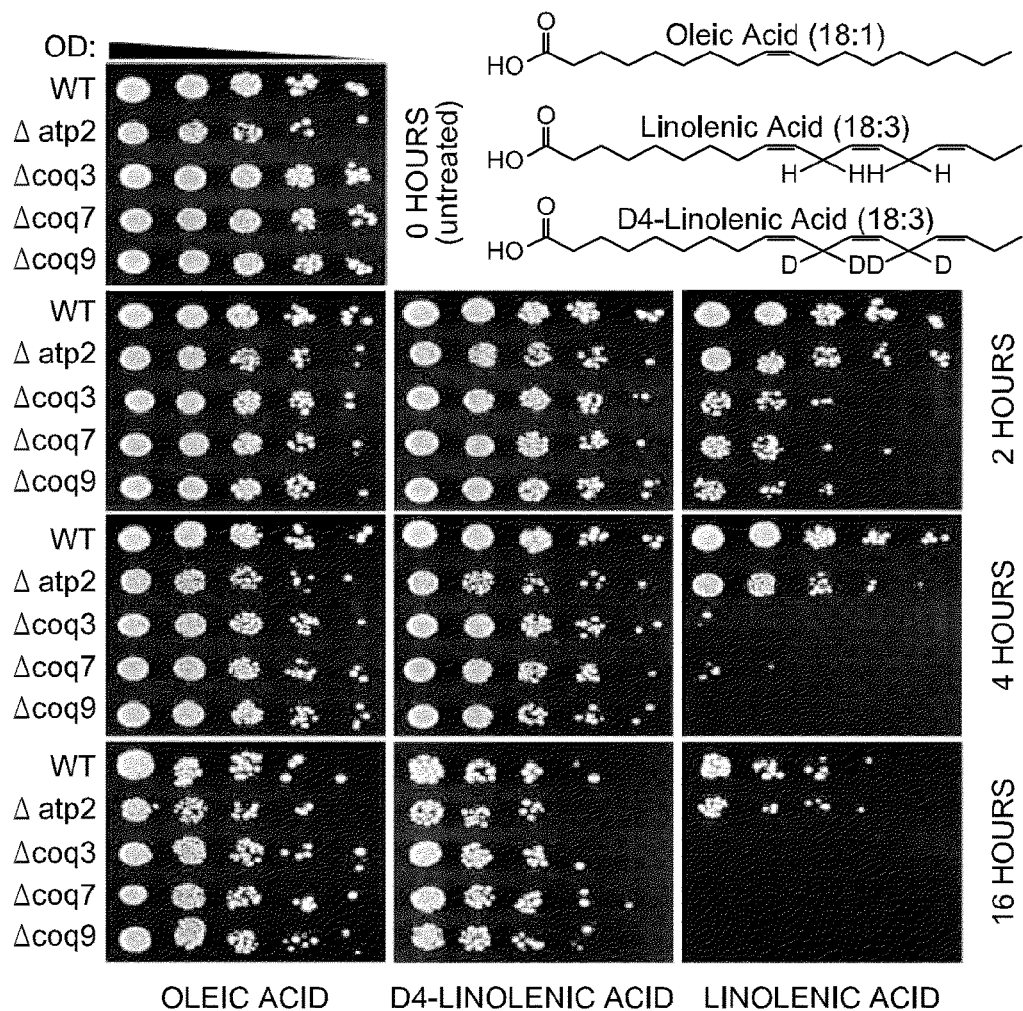
FIG. 3. Sensitivity of coq null mutants to treatment with linolenic acid is abrogated by isotope-reinforcement. Yeast coq3, coq7 and coq9 null mutants were prepared in the W303 yeast genetic background (WT). Yeast strains were grown in YPD medium (1% Bacto-yeast extract, 2% Bacto-peptone, 2% dextrose) and harvested while in log phase growth ($OD_{600\ nm}$=0.1-1.0). Cells were washed twice with sterile water and resuspended in phosphate buffer (0.10 M sodium phosphate, pH 6.2, 0.2% dextrose) to an $OD_{600\ nm}$=0.2. Samples were removed and 1:5 serial dilutions starting at 0.20 OD/ml were plated on YPD plate medium, to provide a zero time untreated control (shown in top left panel). The designated fatty acids were added to 200 µM final concentration to 20 ml of yeast in phosphate buffer. At 2 h, 4 h, and 16 h samples were removed, 1:5 serial dilutions prepared, and spotted onto YPD plate medium. Pictures were taken after 2 days of growth at 30° C. This panel is representative of two independent assays, performed on different days.

A plate dilution assay can be used to assess PUFA sensitivity. This assay can be performed by spotting serial five-fold dilutions of aliquots onto YPD plate media (FIG. 3). The sensitivity of the different strains can be observed by visual inspection of the density of cells in each spot.

Figure 4:
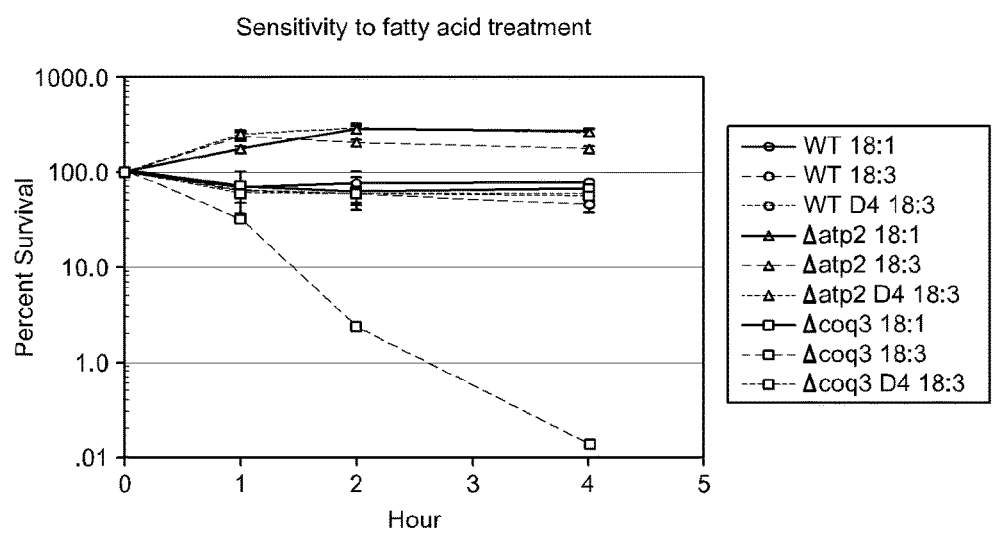
FIG. 4. Yeast coq mutants treated with isotope-reinforced D4-linolenic acid are resistant to PUFA-mediated cell killing. The fatty acid sensitive assay was performed as described in FIG. 3, except that 100 µl aliquots were removed at 1, 2, and 4 h and, following dilution, spread onto YPD plates. Pictures were taken after 2 to 2.5 days, and the number of colonies counted. Yeast strains include Wild type (circles), atp2 (triangles), or coq3 (squares). Fatty acid treatments include oleic C18:1 (solid line), linolenic, C18:3, n-3 (dashed line) or 11,11,14,14-D4-linolenic, C18:3, n-3, (dotted line).

Treatment with linolenic acid causes a dramatic loss of viability of the coq null mutants. In stark contrast, coq mutants treated with the D4-linolenic acid were not killed, and retained viabilities similar to yeast treated with oleic acid. Quantitative colony counting revealed that the viability of cells treated with oleic and D4-linolenic was similar (FIG. 4), while the viability of the coq mutants was reduced more than 100-fold following treatment with the standard linolenic acid for 4 h. These results indicated that isotope-reinforced linolenic acid was much more resistant to autoxidation than was the standard linolenic acid, as evidenced by the resistance of the hypersensitive coq mutants to cell killing.

Example 11

GC-MS can Detect Fatty Acids and PUFAs in Yeast Cells

Figure 5:
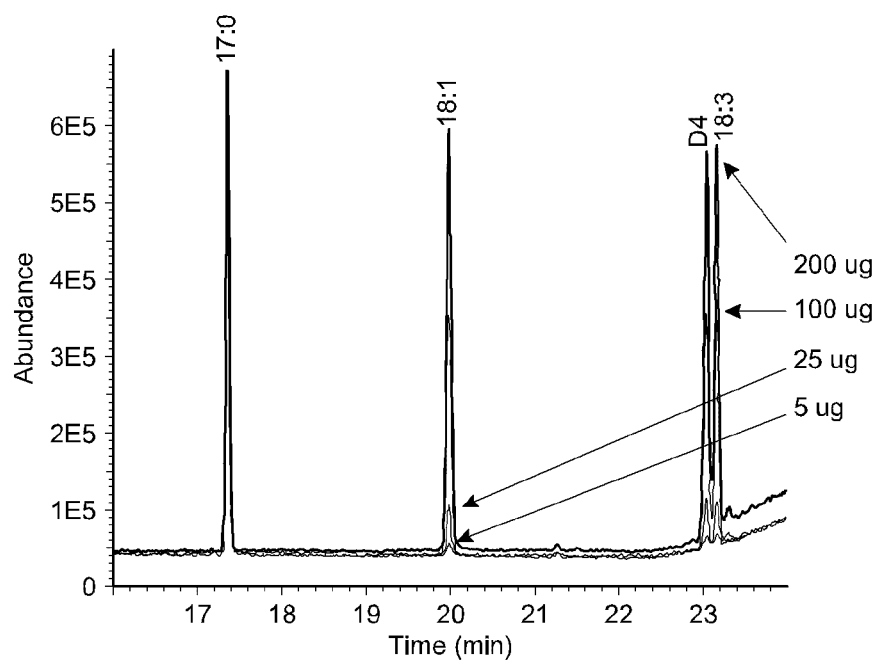
FIG. 5. Separation and detection of fatty acid methyl ester (FAME) standards by GC-MS. FAMEs were prepared as described (Moss C W, Lambert M A, Merwin W H. Appl. Microbiol. 1974; 1, 80-85), and the indicated amounts of free fatty acids and 200 µg of C17:0 (an internal standard) were subjected to methylation and extraction. Samples analyses were performed on an Agilent 6890-6975 GC-MS with a DB-wax column (0.25 mm×30 m×0.25-m film thickness) (Agilent, catalog 122-7031).

Yeast do not synthesize PUFAs, however they do incorporate exogenously supplied linoleic and linolenic acids (Avery S V, et al. *Applied Environ. Microbiol.* 1996; 62, 3960; Howlett N G, et al. *Applied Environ. Microbiol.* 1997; 63, 2971). Therefore, it seems likely that yeast would also incorporate exogenously supplied D4-linolenic acid. However, it is possible that the differential sensitivity to linolenic and D4-linolenic might be attributed to differences in integration into the cell rather than autoxidation. To test whether this is the case, the extent of uptake of this fatty acid was monitored. First the conditions of separation of fatty acid methyl esters (FAME) of C18:1, C18:3, D4-18:3 and C17:0 (to be used as an internal standard) were determined. The GC-MS chromatogram shown in FIG. 5 establishes both separation and sensitivity of detection of these fatty acid methyl ester standards.

Figure 6:
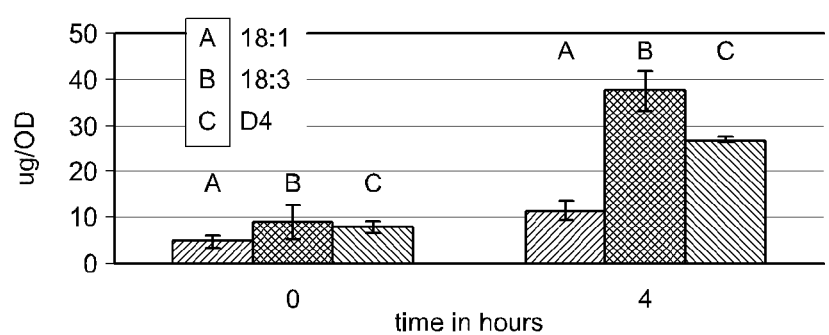
FIG. 6. Uptake of exogenously supplied fatty acids by yeast. WT (W303) yeast were harvested at log phase and incubated in the presence of 200 µM of the designated fatty acid for either 0 or 4 h. Yeast cells were harvested, washed twice with sterile water and then subjected to alkaline methanolysis and saponification, and lipid extraction as described (Moss C W, Lambert M A, Merwin W H. Appl. Microbiol. 1974; 1, 80-85; (Shaw, 1953 Shaw, W. H. C.; Jefferies, J. P. Determination of ergosterol in yeast. Anal Chem 25:1130; 1953). Each designated fatty acid is given as µg per $OD_{600\ nm}$ yeast, and was corrected for the recovery of the C17:0 internal standard.

Wild-type yeast were harvested during log phase growth and incubated in the presence of exogenously added fatty acid (for 0 or 4 h) in the presence of phosphate buffer plus 0.20% dextrose, as described for the fatty acid sensitivity assay. Cells were harvested, washed twice with 10 ml sterile water, and the yeast cell pellets were then processed by alkaline methanolysis as described above. The fatty acids are detected as methylesters (FAMEs) following GC-MS with C17:0 added as an internal standard (FIG. 6). The amounts of 18:3 and D4 detected after 4 h incubation were extrapolated from the calibration curve. These results indicate yeast avidly incorporate both linolenic and D4-linolenic acid during the 4 h incubation period. Based on these results, it is obvious that the enhanced resistance of the coq mutant yeast to treatment with D4-C18:3 was not due to lack of uptake.

D2-linolenic, 11, 11-D2-linolenic acid and 14, 14-D2-linolenic acid, were also used on this yeast model and rendered comparable protection.

Example 12

Figure 7:
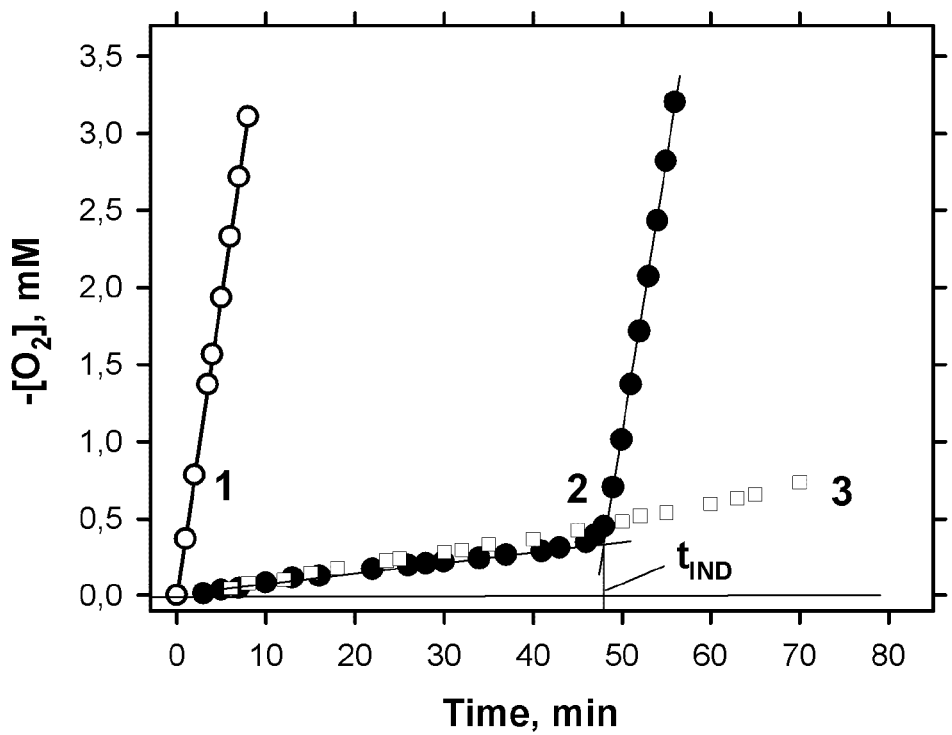
FIG. 7. Kinetics of $O_2$ consumption accompanied the oxidation of 0.71 M LA (plots 1 and 2) and 0.71 M D2-LA (plot 3) in chlorobenzene initiated by 40 mM AMVN at 37° C. Plot 2-0.23 mM HPMC was added to 0.71 M LA.

Kinetic Isotope Effect in Non-Enzymatic Oxidation of D2-LA in a Chain Reaction Format The kinetics of oxygen consumption during the oxidation of LA and D2-LA was studied with a glass capillary microvolumeter (FIG. 7). The rate of oxidation, $R_{OX}$, was measured as a slope of $[O_2]$ traces. The rate of initiation, $R_{IN}$, was determined by the inhibitor method with HPMC ("6-hydroxy-2,2,5,7,8-pentamethylbenzochroman") as a reference inhibitor. $R_{IN}$ was calculated from the induction period of inhibited oxidation, $t_{IND}$: $R_{IN}=2 \cdot [HPMC]/t_{IND}$. The rate of oxidation of 0.71 M LA (FIG. 7) was found to be $6.1 \times 10^{-6}$ M/s. When the process was inhibited by 0.23 mM chain-breaking antioxidant HPMC, the duration of the induction period, $t_{IND}$, was about 48 min, with the $R_{IN}$ value of around $0.16 \times 10^{-6}$ M/s. The length of the kinetic chain calculated from these data was: $v=R_{OX}/R_{IN}=38 \pm 3$. Based on this data, the calculated oxidizability of LA was $0.0215 \pm 0.008$ $M^{-0.5}s^{-0.5}$ (n=5) [Cosgrave J. P, et. al. *Lipids*, 1987, 22, 299-304]. For D2-LA, the reduction of $R_{OX}$ to $0.18 \times 10^{-6}$ M/s was observed (FIG. 7). In contrast to LA, addition of HPMC did not result in the decrease in $R_{OX}$ and the appearance of any detectable induction period (data not shown). The latter precludes a direct determination of $R_{IN}$. For a $R_{IN}$ value for D2-LA oxidation being comparable to that of LA it follows that D2-LA oxidation was not a chain process ($v=0.18 \times 10^{-6}/0.16 \times 10^{-6} \approx 1.1$). An estimated kinetic isotope effect ("KIE"), from comparison of $R_{OX}$ for LA and D2-LA, was around $6.1 \times 10^{-6}/0.18 \times 10^{-6} \approx 35$. A similar KIE was determined during the oxidation of LA and 11,11-$d_2$-LA in Triton X-100 aqueous micelles (data not shown). For comparative purposes, the theoretical KIE is 6.9 at 25° C. See Carpenter, "Determination of Organic Reaction Mechanisms" (John Wiley & Sons, 1984), p. 89.

Example 13

Small Amounts of D2-LA Protect LA Against Peroxidation

Figure 8:
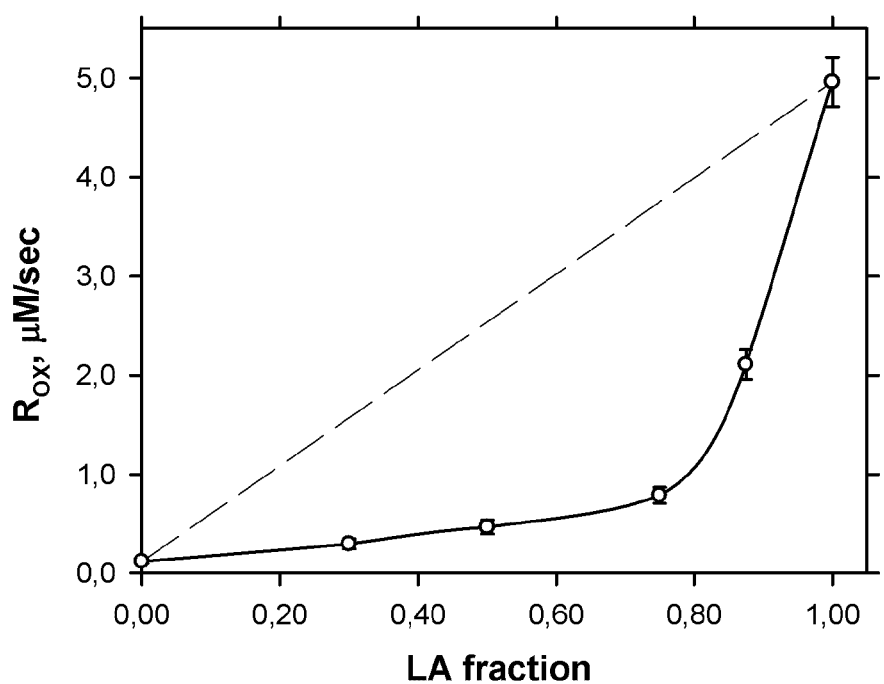
FIG. 8. Dependence of the rate of oxidation of the mixture of LA and D2-LA in chlorobenzene solution on mixture composition. Conditions: [LA]+[11,11-d$_2$-LA]=0.775 M; [AMVN]=0.0217 M; 37° C. R$_{IN}$=(1.10±0.08)×10$^{-7}$ M/sec.

To simulate the likely in vivo conditions, the kinetics of the oxidation of the mixtures of D2-LA and LA were studied (FIG. 8). In the experiments, the concentration of LA plus 11,11-d2-LA was 0.775 M; the concentration of AMVN was 0.0217 M; and the reactions were carried out at 37° C. The results afforded an $R_{IN}$ of $1.10 \pm 0.08 \times 10^{-7}$ M/sec. Additionally, the rate of oxidation of the mixtures was found to be non-additive and much lower than the additive value of $R_{OX}$ for the individual compounds. Surprisingly, D2-LA essentially 'protects' the non-deuterated LA against autoxidation. A qualititatively similar effect was also observed during the oxidation of the mixture of 11,11-D2-LA with non-deuterated methyl linoleate (data not shown). These results suggest that even a partial replacement of non-deuterated LA by D2-LA may substantially slow down PUFA peroxidation.

Example 14

Small Amounts of D2-LA Protect LA Against Peroxidation In Vivo

Figure 9:
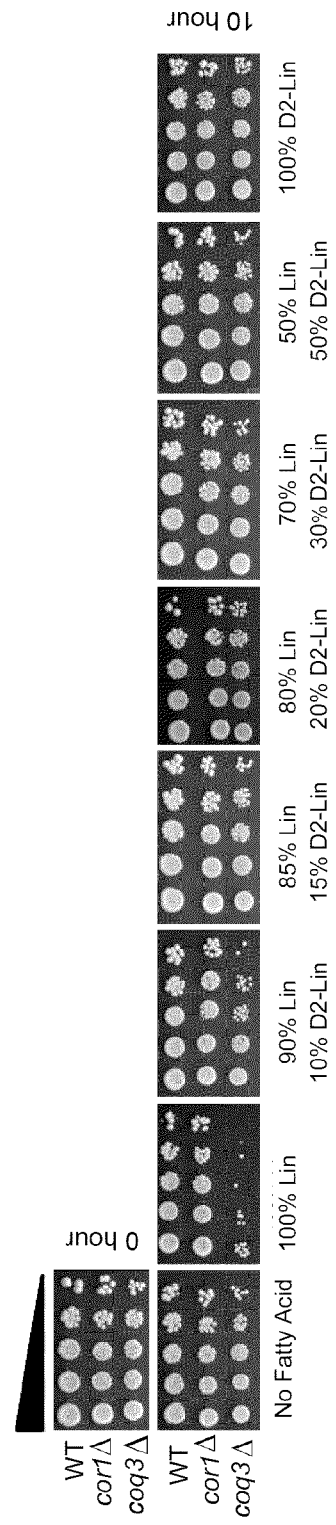
FIG. 9. Isotope reinforcement at the bis-allylic position of polyunsaturated fatty acids attenuates lipid autoxidation. Wild-type, yeast Q-less coq3, or respiratory deficient cor1 null mutants were incubated in the presence of 200 μM of LA and D2-LA at different ratios of PUFAs. Serial dilutions (1:5) starting at 0.2 OD/ml were spotted on YPD solid plate medium. A zero-time untreated control is shown on the top left. Growth at 30° C.

The results described in Example 13 were reproduced in vivo using Q-less coq3 yeast strains and different ratios of LA to D2-LA (FIG. 9). Wild-type, yeast Q-less coq3, or respiratory deficient cor1 null mutants were incubated in the presence of 200 µM of LA and D2-LA at different ratios of PUFAs, as indicated in FIG. 9. Serial dilutions (1:5) starting at 0.2 OD/ml were spotted on YPD solid plate medium. Additionally, a zero-time untreated control was utilized and the results are shown on the top left of FIG. 9. Growth was at 30° C. The results indicate that approximately 10-15% of D2-LA was a sufficiently minimal amount to cancel the toxicity of LA. A similar incubation with the mono-deuterated PUFA, 11,11-D,H-LA, afforded no detectable loss in cell viability after 3 hours of treatment (data not shown). These results suggest that both D2-LA and 11,11-D,H-LA were resistant to lipid peroxidation.

Wild-type yeast cells were treated as described above except yeast were treated with 200 µM of the designated fatty acid for 2 hours, washed with sterile water, and were either not treated (triangles) or treated with 50 µM $CuSO_4$ (squares) at room temperature. After 60 min of copper treatment cells were treated with 8 µM C11-Bodipy 581/591 for 30 min at room temperature. Four 100 µl aliquots were plated in a 96-well plate and the fluorescence was measured. Wild-type yeast cells treated with copper in the absence or presence of PUFA have significantly higher levels of lipid peroxidation as compared to yeast not treated with copper. However, copper-stressed wild-type yeast cells treated with 11,11-$D_2$-LA have lower levels of lipid peroxidation similar to yeast not treated with PUFA. Mono-deuterated 11,11-D, H-LA offered similar protection.

Example 15

Small Amounts of D4-ALA Protect ALA Against Peroxidation In Vivo

Figure 10:
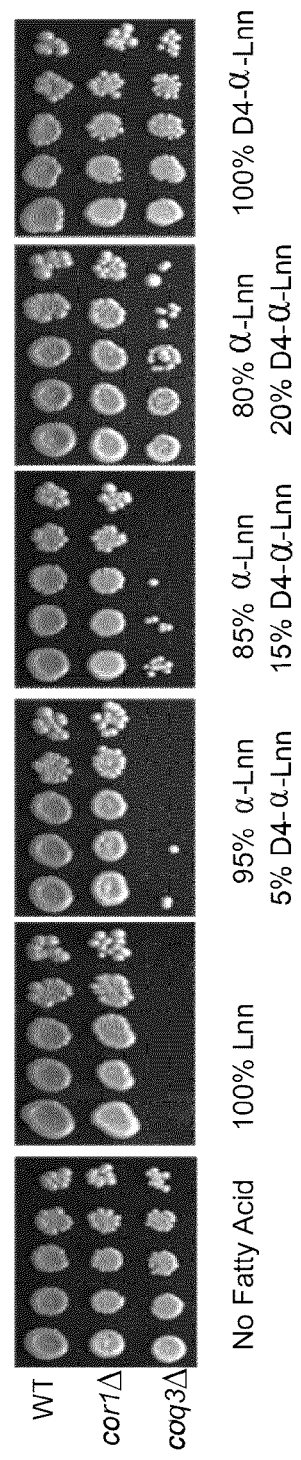
FIG. 10. Isotope reinforcement at the bis-allylic position of polyunsaturated fatty acids attenuates lipid autoxidation. Wild-type, yeast Q-less coq3, or respiratory deficient cor1 null mutants were incubated in the presence of 200 μM of ALA and D4-LA at different ratios of PUFAs. Serial dilutions (1:5) starting at 0.2 OD/ml were spotted on YPD solid plate medium. Growth at 30° C.

The experimental protocol described for Example 14 was also reproduced in vivo using Q-less coq3 yeast strains (FIG. 10) and different ratios of ALA to D4-ALA. Wild-type, yeast Q-less coq3, or respiratory deficient cor1 null mutants were incubated in the presence of 200 µM of ALA and D4-Lnn (Linolenic acid) at different ratios of PUFAs, as indicated in FIG. 10. Serial dilutions (1:5) starting at 0.2 OD/ml were spotted on YPD solid plate medium. Growth was at 30° C. The results indicate that approximately 15-20% of D2-Lnn was a sufficiently minimal amount to cancel the toxicity of ALA. Moreover, results indicate that the content of PUFA taken up by yeast cells roughly reflects the ratios added and suggests that yeast cells do not discriminate among the PUFAs provided.

Example 16

Figure 11:
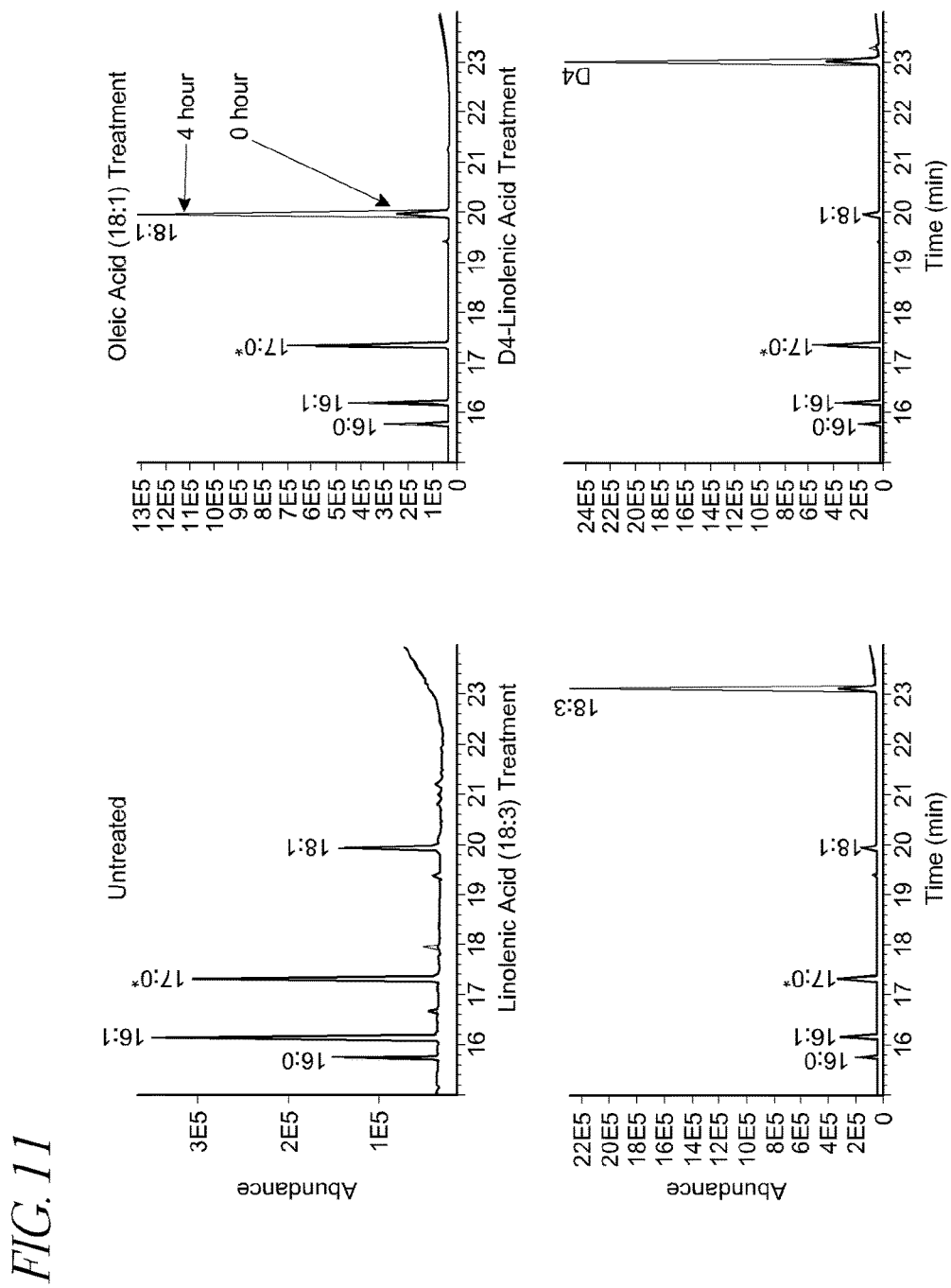
FIG. 11. Chromatograms of the yeast extracts subjected to GC-MS analyses. The different traces represent the 0 and 4 h incubations, respectively. The peak area of Each FAME (C18:1, C18:3 and D4-linolenic) was divided by the peak area of the C17:0 standard, quantified with a calibration curve. The endogenous 16:0 and 16:1 change very little, while the exogenously added fatty acids increased significantly.

D-PUFA Mitigates Oxidative Stress and Increases Survival in Retinal Cells Implicated in AMD and Diabetic Retinopathy Pathology Several cell types, including microvascular endothelium (MVEC), retinal pigment epithelium (RPE) and retinal neurons (retinal ganglion cells) were tested for survival in cell culture. Cells were kept in the medium containing either hydrogenated (control) or deuterated D2-linoleic (ω-6; LA) and D4-linolenic (ω-3; ALA) acids (20 µM; ratio of ω-6 to ω-3: 1:1 or 2:1) for 72 hrs. The incorporation of PUFAs into cells was monitored by GC (FIG. 11). PUFAs were shown to be readily taken up by cells according to the Table 1, showing incorporation of PUFAs into MVECs.

TABLE 1

|  |  | Area unlabelled | Area labelled | ratio |
|---|---|---|---|---|
| control | linoleate | 78392976 | 4556042 | 0.058 |
|  | linolenate | 1488866 | 149411 | 0.100 |
| PUFA | linoleate | 96026830 | 5525295 | 0.058 |
|  | linolenate | 2347729 | 113468 | 0.048 |
| Deuterated PUFA | linoleate | 34957060 | 2599969 | 0.074 |
|  | linolenate | 747128 | 134824 | 0.180 |

Figure 12:
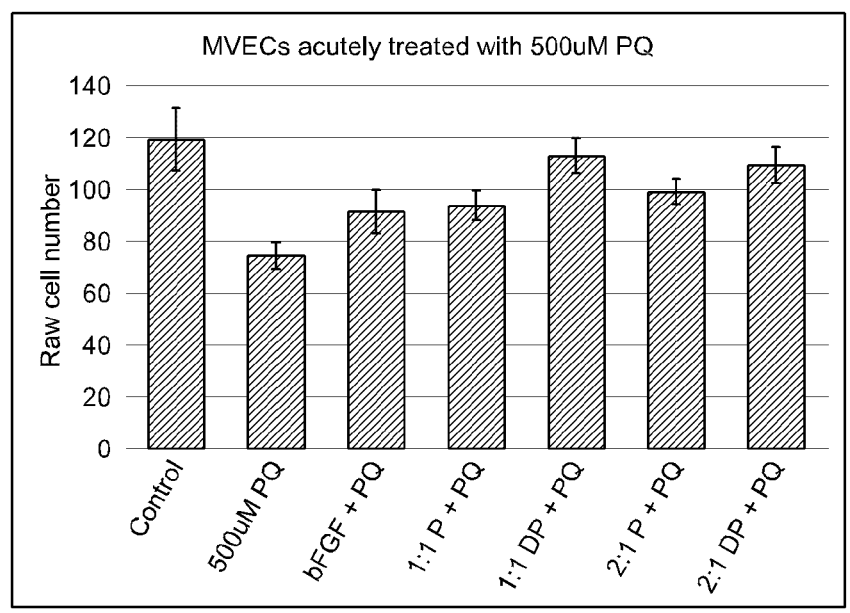
FIG. 12. Survival of H— and D-PUFA treated MVEC cells after acute intoxication by paraquat. For all cell types tested, D-PUFA had protective effect compared to controls, similar to that shown on Figure for MVEC cells.

The cells were then treated with paraquat (PQ; 500 μM), a common oxidative stress-generating compound. For survival measurement, cells were counted using haemocytometer and trypan blue exclusion method. FIG. 12 shows the survival of H— and D-PUFA treated MVEC cells after acute intoxication by paraquat. For all cell types tested, D-PUFA had protective effect compared to controls, similar to that shown in FIG. 8 for MVEC cells.

Example 17

Toxicology Studies of Mice Supplemented with D-PUFA Reveal No Anomalies in Major Blood Biomarkers With a more protracted dosing paradigm (i.e. 3 weeks of dietary replacement), chemical analysis of blood serum of H-PUFA- and D-PUFA-supplemented mice (performed at UC Davis) revealed no difference in major biomarkers of renal function, liver function, blood lipids, etc for H-PUFA/D-PUFA saline treated mice. In this example, D-PUFA is a 2:1 mixture of D2-linoleic acid: D4-linolenic acid.

Tested parameters included measurements of triglycerides; total protein; total bilirubin; phosphorus; free fatty acids; HDL; glucose; creatine; cholesterol; calcium; blood urea nitrogen; alkaline phosphatase; albumin; aspartate aminotransferase; and others in Table 2.

TABLE 2

| Mouse ID # | Sample volume | Alanine Aminotransferase U/L | Aspartate Aminotransferase U/L | Albumin g/dl | Alkaline Phosphatase U/L | Blood Urea Nitrogen mg/dl | Calcium mg/dl | Cholesterol mg/dl | Creatinine mg/dl |
|---|---|---|---|---|---|---|---|---|---|
| 4 | 100 | 273.0 | 3008.7 | 3.09 | 81.7 | 19.1 | 7.96 | 148.3 | 0.189 |
| 5 | 110 | 5726.7 | 8478.9 | 3.42 | 31.1 | 25.4 | 7.40 | 185.1 | 0.356 |
| 7 | 100 | 156.0 | 1470.6 | 2.82 | 35.1 | 18.9 | 7.64 | 151.2 | 0.154 |
| 10 | 60 | 518.4 | 4653.0 | 3.02 | QNS | 20.1 | 6.78 | 184.0 | 0.151 |
| 11 | 70 | 144.0 | 1635.3 | 3.63 | 72.7 | 20.3 | 8.75 | 170.8 | 0.179 |
| 13 | 14 | 3518.1 | 15669.0 | QNS | <0.1 | 31.5 | QNS | 166.5 | 1.126 |
| 14 | 75 | 216.9 | 2107.8 | 3.03 | 42.4 | 24.4 | 7.46 | 173.6 | 0.170 |
| 25 | 75 | 589.5 | 4707.0 | 3.20 | 18.8 | 18.0 | 5.97 | 193.4 | 0.126 |
| 27 | 100 | 727.2 | 6015.6 | 2.63 | <0.1 | 36.2 | 5.71 | 166.7 | 1.453 |
| 28 | 100 | 468.9 | 4018.5 | 2.93 | 49.3 | 21.2 | 6.90 | 164.4 | 0.232 |
| 29 | 29 | 1898.1 | 12510.0 | QNS | QNS | 24.9 | QNS | 208.8 | 0.111 |
| 30 | 100 | 2963.7 | 5371.2 | 3.38 | 50.3 | 18.2 | 6.29 | 174.7 | 0.225 |
| Mean D-PUFA | 76 | 1508 | 5289 | 3.17 | 52.6 | 22.8 | 7.67 | 168.5 | 0.332 |
| SD D-PUFA | 33 | 2225 | 5189 | 0.30 | 23.0 | 4.6 | 0.66 | 14.5 | 0.357 |
| Mean H-PUFA | 81 | 1329 | 6524 | 3.04 | 39.5 | 23.7 | 6.22 | 181.6 | 0.429 |
| SD D-PUFA | 31 | 1078 | 3428 | 0.33 | 17.9 | 8 | 0.51 | 19.0 | 0.575 |

| Mouse ID # | Glucose mg/dl | High Density Lipoprotein mg/dl | Non-esterified Fatty Acid mEq/L | Phosphorus mg/dl | Total Bilirubin mg/dl | Total Protein g/dl | Triglyceride mg/dl |
|---|---|---|---|---|---|---|---|
| 4 | 160.2 | 104.49 | 1.08 | 13.07 | 0.185 | 5.32 | 38.9 |
| 5 | 355.6 | 134.37 | 1.07 | 18.59 | 0.275 | 6.56 | 57.9 |
| 7 | 174.6 | 107.39 | 1.11 | 10.14 | 0.192 | 5.26 | 82.7 |
| 10 | 136.5 | 138.15 | 1.06 | QNS | 0.272 | 6.07 | 46.1 |
| 11 | 107.9 | 139.86 | 1.18 | 9.33 | 0.162 | 5.72 | 33.5 |
| 13 | 176.4 | 135.09 | 0.99 | QNS | QNS | QNS | 31.5 |
| 14 | 93.3 | 47.78 | 1.06 | 10.41 | 0.235 | 6.07 | 43.8 |
| 25 | 164.5 | 147.96 | 1.01 | 18.39 | 0.269 | 6.74 | 41.0 |
| 27 | 88.3 | 98.46 | 0.87 | 24.57 | 0.301 | 6.26 | 26.9 |
| 28 | 224.9 | 50.54 | 1.02 | 14.16 | 0.231 | 5.87 | 49.6 |
| 29 | QNS | 77.58 | 0.20 | QNS | QNS | QNS | 27.9 |
| 30 | 227.4 | 131.04 | 1.17 | 21.42 | 0.349 | 6.28 | 46.7 |
| Mean D-PUFA | 172.1 | 115.30 | 1.08 | 12.31 | 0.220 | 5.83 | 47.8 |
| SD D-PUFA | 87.0 | 33.21 | 0.06 | 3.78 | 0.048 | 0.50 | 17.7 |
| Mean H-PUFA | 176.3 | 101.12 | 0.85 | 19.64 | 0.288 | 6.29 | 38 |
| SD D-PUFA | 65.5 | 39.40 | 0.38 | 4.44 | 0.050 | 0.36 | 11 |

Example 18

Histopathologic Studies

Microscopic changes were coded by the most specific topographic and morphologic diagnosis, and the Systematized Nomenclature of Medicine (SNOMED) and the National Toxicology Program's Toxicology Data Management System (TDMS) terminology manuals were used as guidelines. Data were recorded in Labcat® Histopathology module 4.30. A four-step grading system (minimal, mild, moderate, and marked) was used to define gradable changes.

C57BL6 male mice were dosed orally in the diet with PUFAs on Study Days 1 through 14, and were necropsied on Study Day 15. Group 1 consisted of 4 mice and received hydrogenated PUFAs. Group 2 consisted of 5 mice and received deuterated PUFAs (D2-LA and D4-ALA) On Study Day 8, all mice received intraperitoneal (IP) saline. Complete sets of protocol-specified tissues [liver (3 to 7 sections), lungs with bronchi (2 to 5 lobes), spleen, heart, and kidneys] from all submitted mice were examined histopathologically. No difference was observed between the H-PUFA and D-PUFA groups.

Example 19

Evaluation of Tissue-Specific Deuteration

WT mice were housed at 12 animals (males separate from females) per cage and fed for 90 days ad libitum (typically, 5-6 g/day) on the AIN 93 diet, as pellets, with 6% total fat. Approximately 10% of that total fat was made up of 1:1 mixture of D2-LA/D4-ALA (group 1), D2-LA/ALA (group 2), or LA/ALA (control group). The animals were sacrificed, organs harvested and stored at low temperature prior to analysis without the use of preservation agents. Lipid fractions were separated, pre-treated and analyzed by LC-MS according to standard protocols using LA, D2-LA, ALA and D4-ALA as controls.

Figure 13:
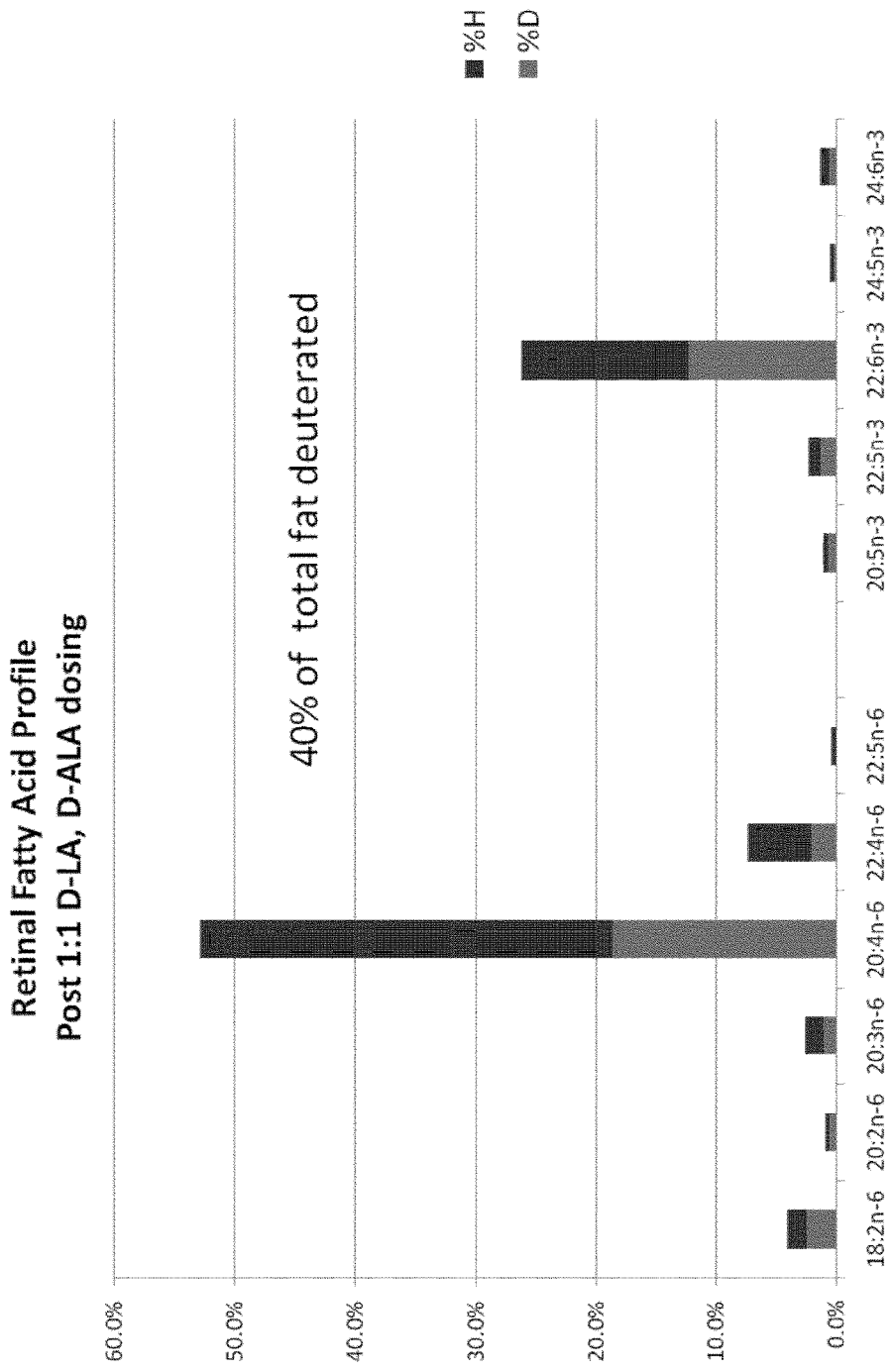
FIG. 13. Animal dosage studies of 1:1 D2-LA/D4-ALA indicating tissue enrichment with deuterium.
Figure 14:
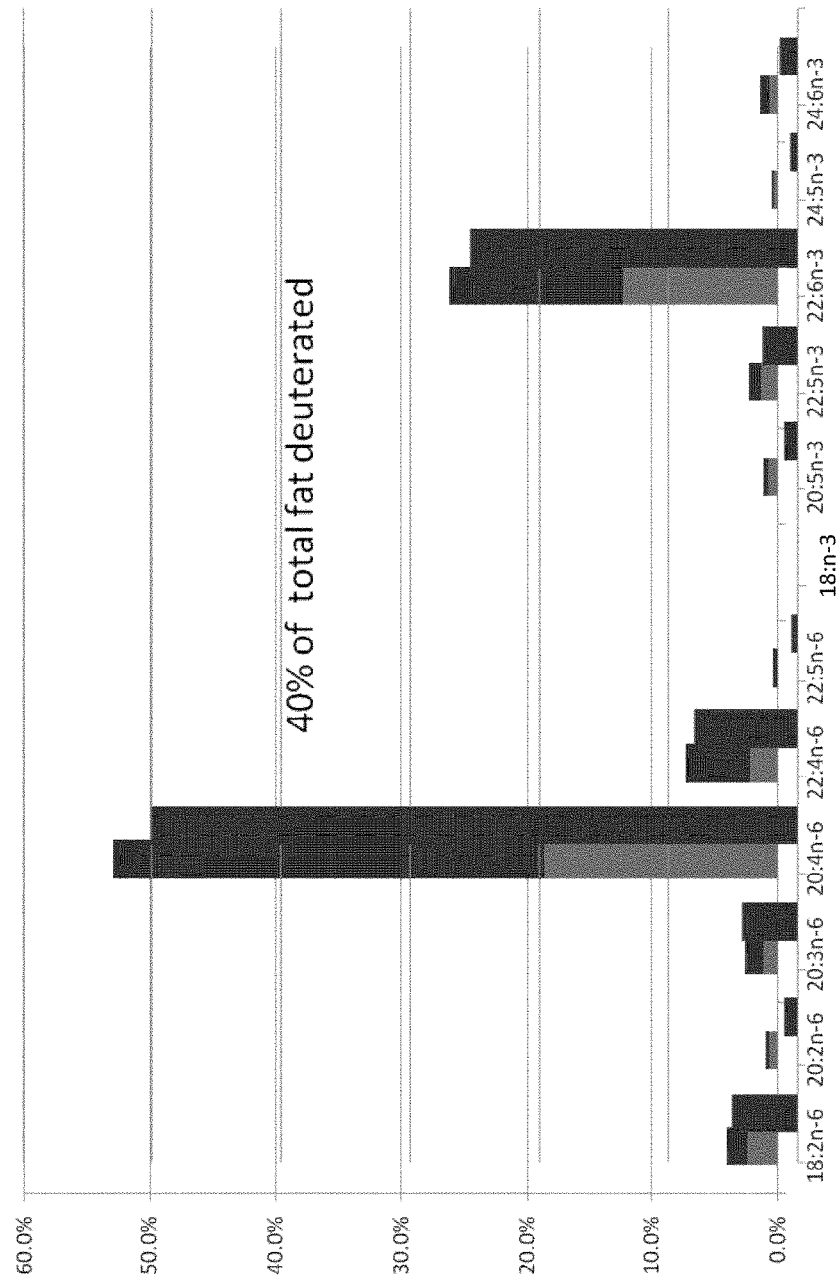
FIG. 14. Animal dosage studies of 1:1 D2-LA/D4-ALA comparing any changes in fat distribution.
Figure 15:
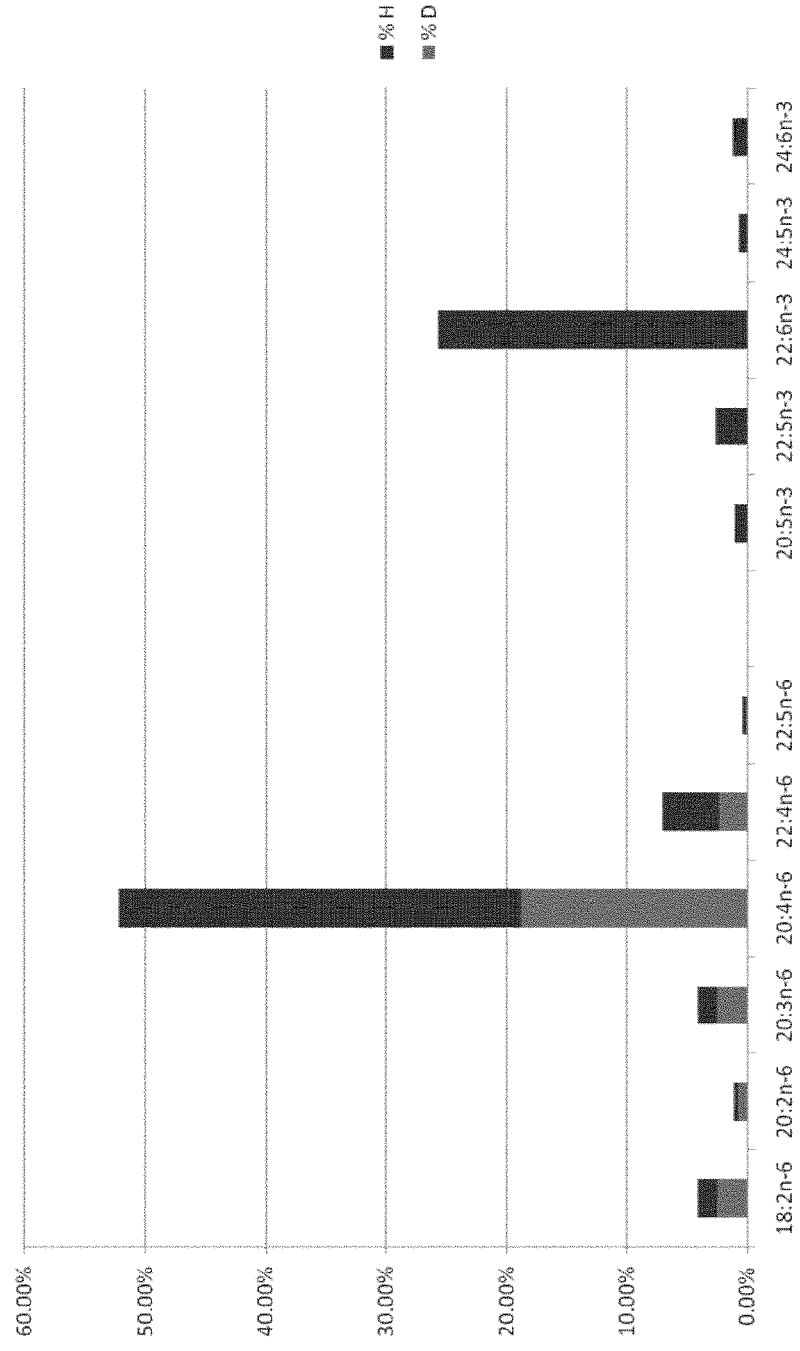
FIG. 15. Animal dosage studies of 1:1 D2-LA/ALA indicating tissue enrichment with deuterium.

Dosage studies of 1:1 D2-LA/D4-ALA indicated that tissues became highly enriched in deuterium, with about 40% of the total fat being deuterated (FIG. 13). Moreover, these studies indicated that fat distribution remained relatively unchanged by the tested dosage (FIG. 14). After dosage studies of 1:1 D2-LA/ALA, it was determined that about 27% of the total fat was deuterated (FIG. 15).

Figure 16:
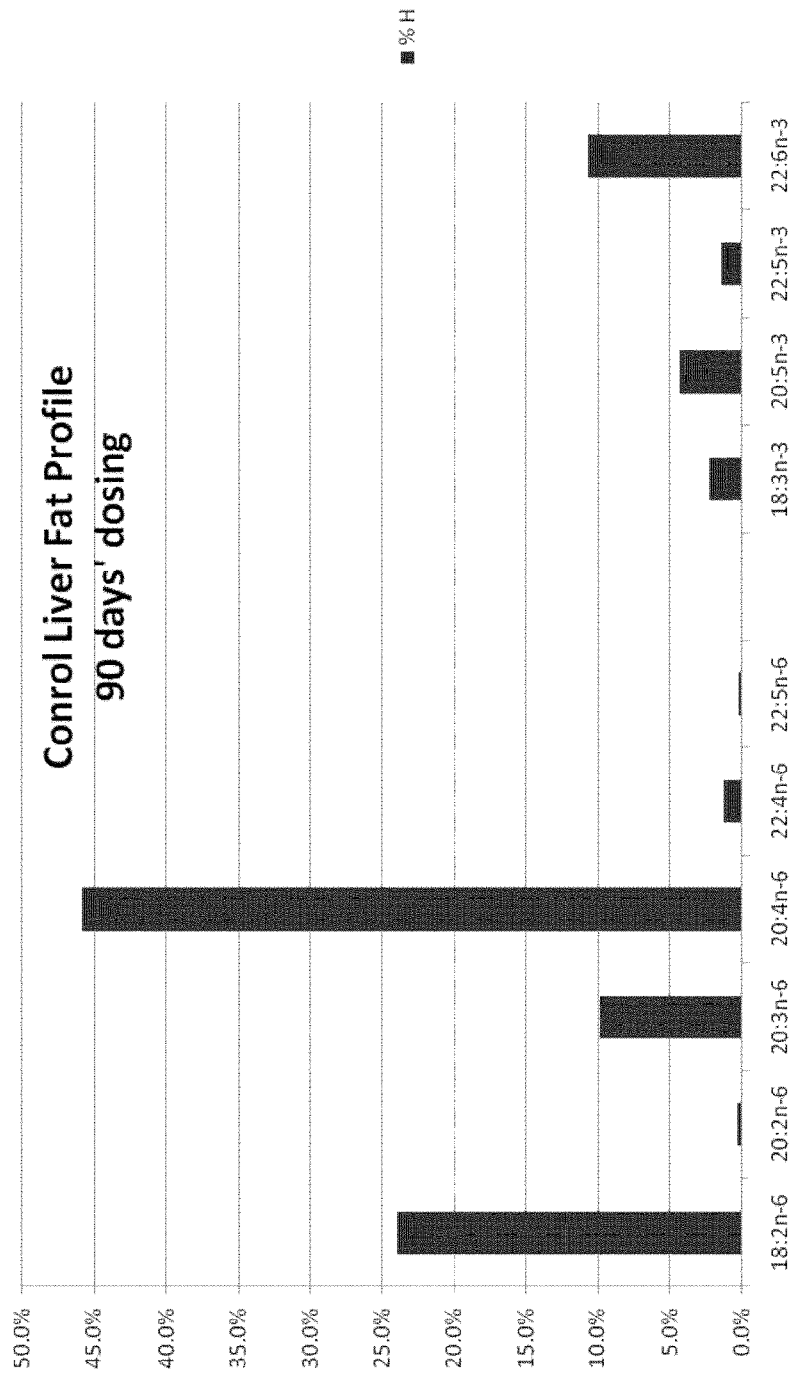
FIG. 16. Control liver fat profile after 90-day animal dosage study.
Figure 17:
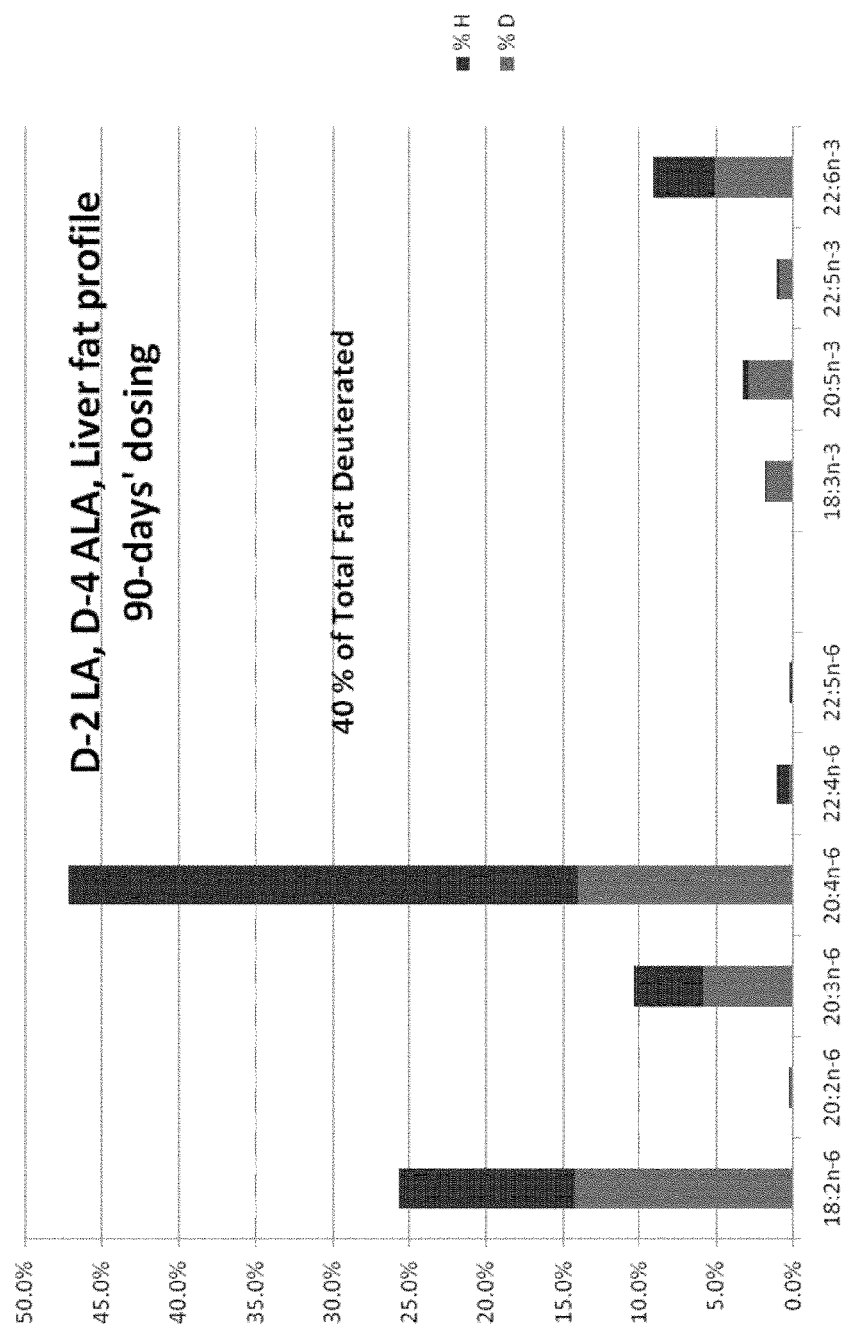
FIG. 17. Animal dosage studies of 1:1 D2-LA/D4-ALA indicating liver fat profile and enrichment with deuterium.
Figure 18:
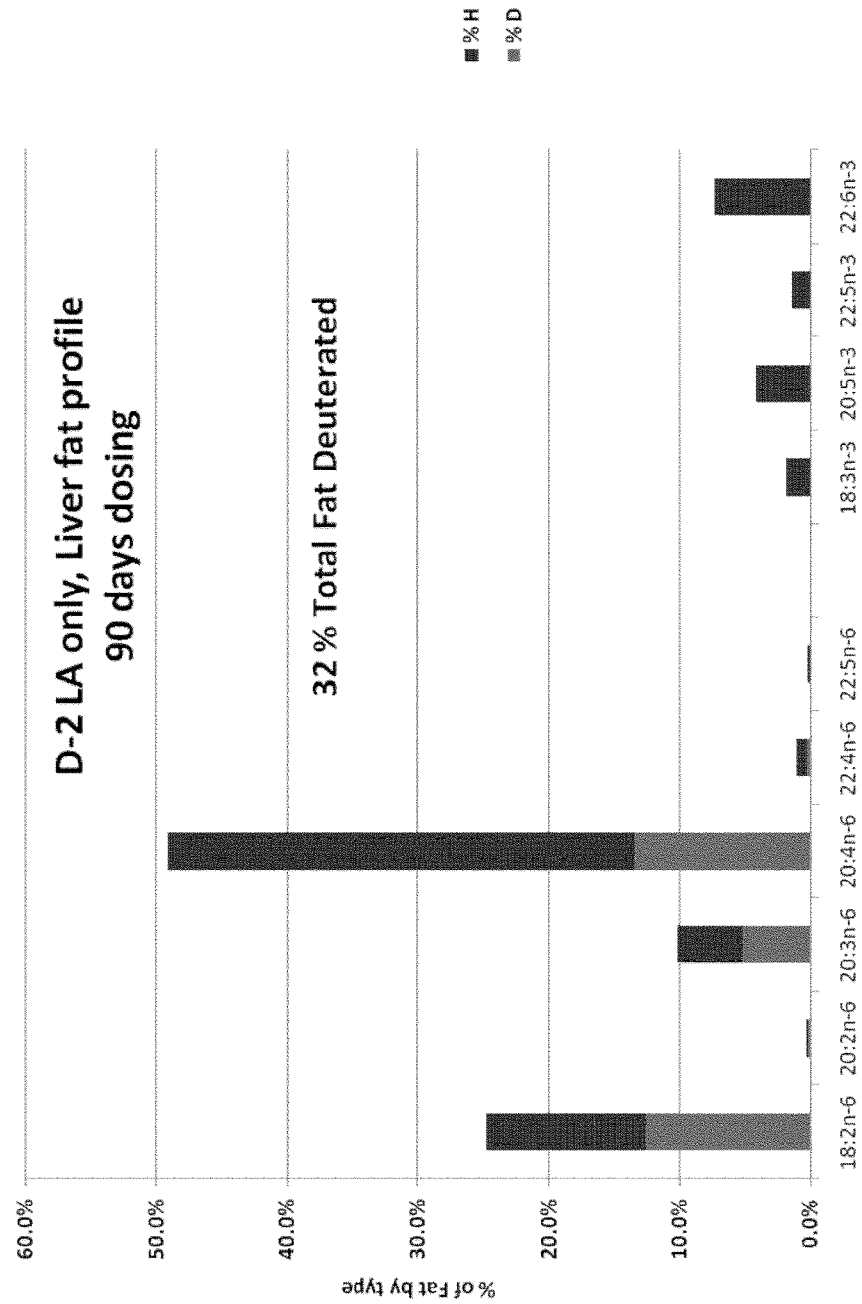
FIG. 18. Liver fat profile after 90-day animal dosage study with D2-LA.
Figure 19:
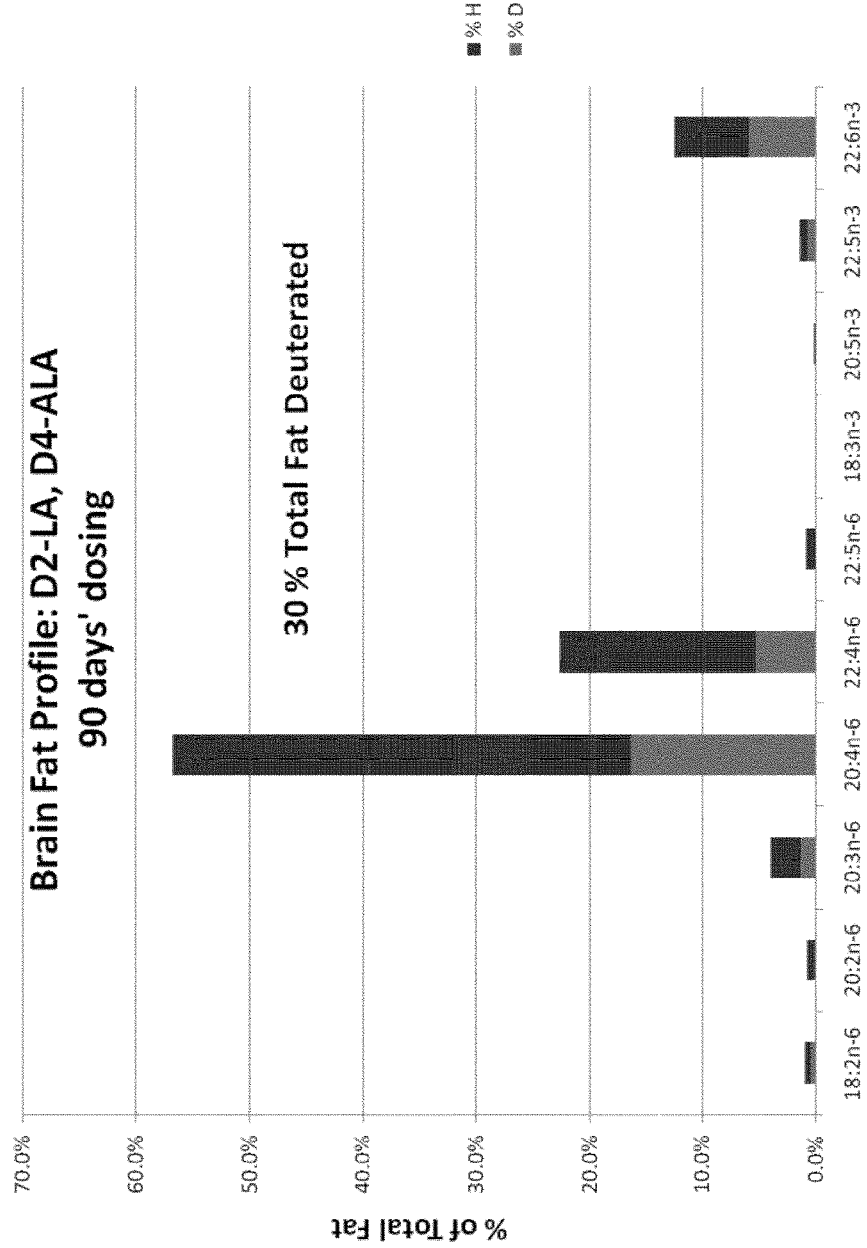
FIG. 19. Animal dosage studies of 1:1 D2-LA/D4-ALA indicating brain fat profile and enrichment with deuterium.
Figure 20:
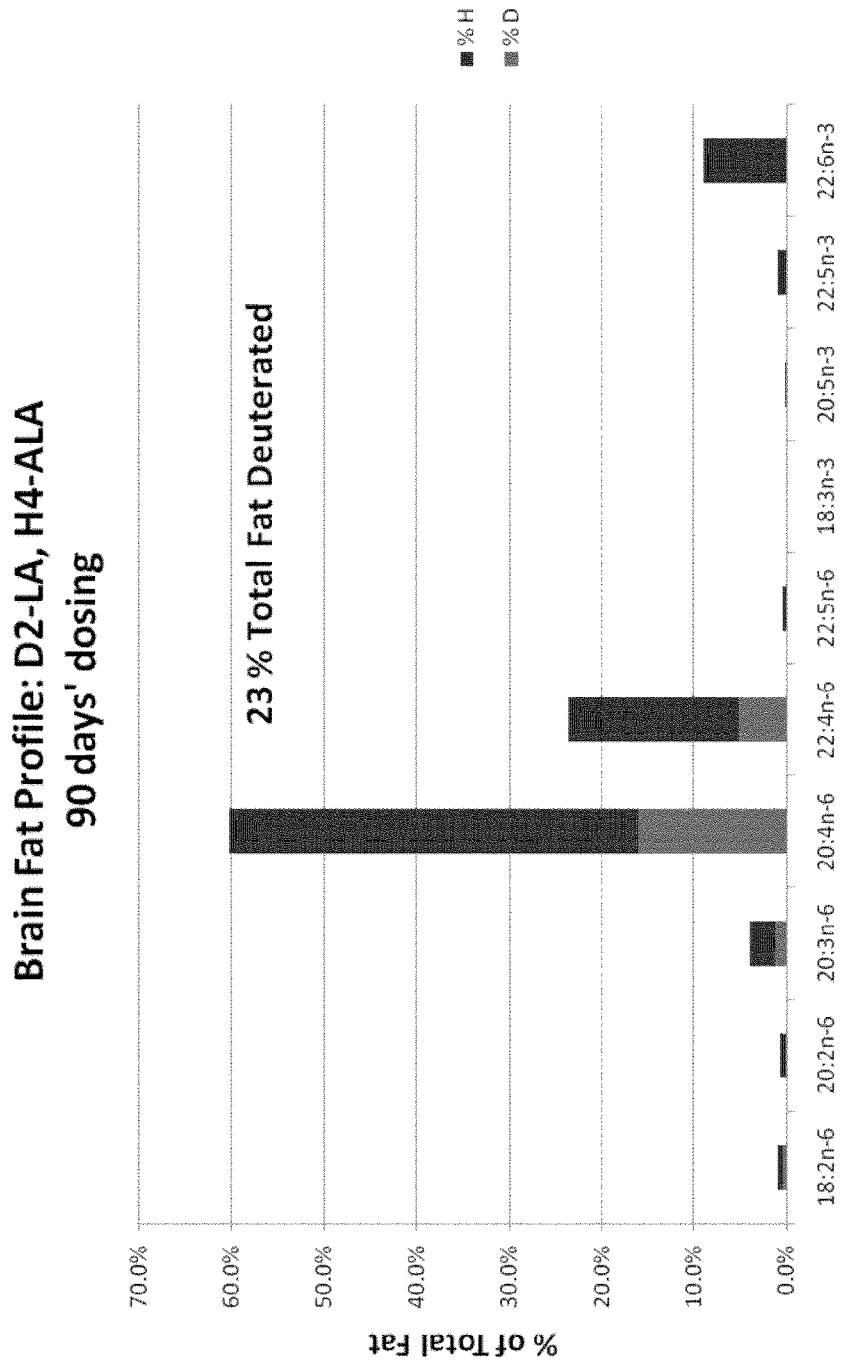
FIG. 20. Animal dosage studies of 1:1 D2-LA/ALA indicating brain fat profile and enrichment with deuterium.
Figure 21:
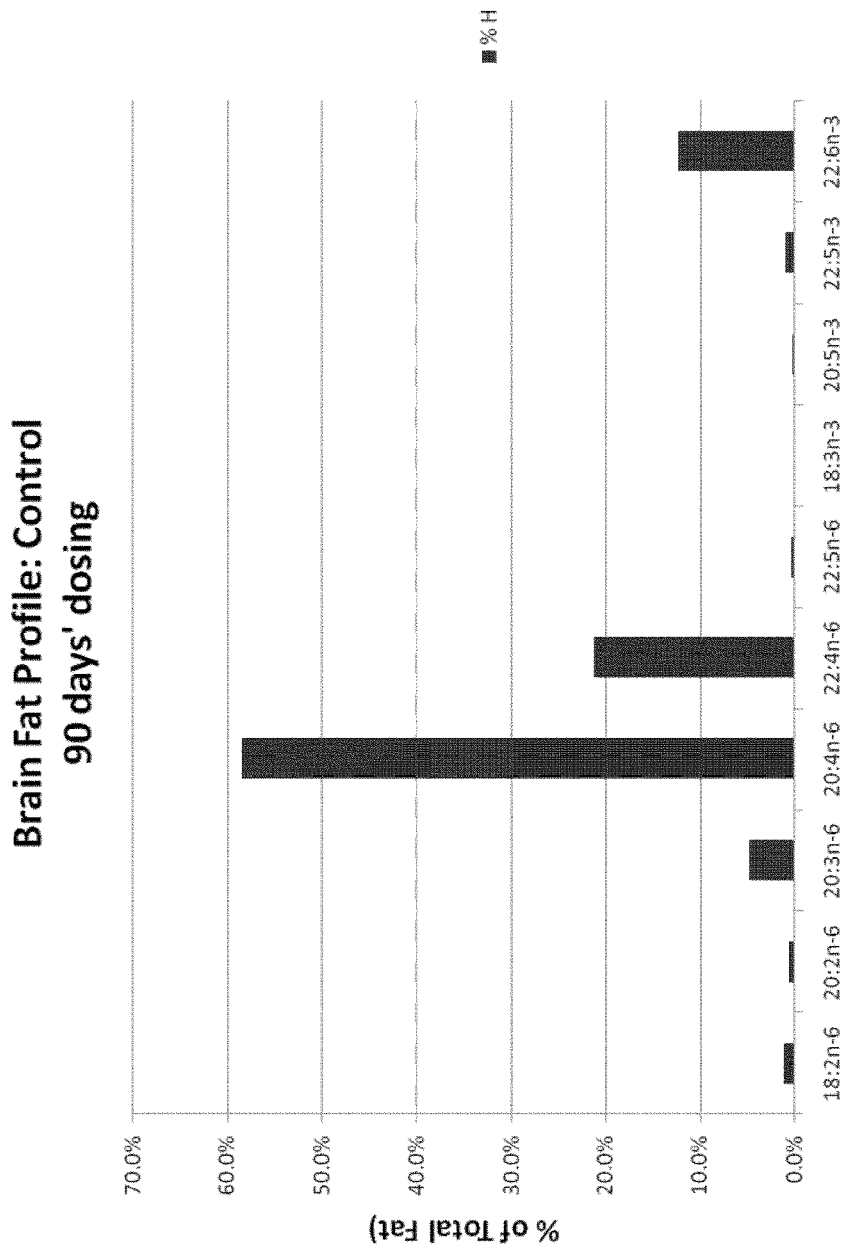
FIG. 21. Control brain fat profile after 90-day animal dosage study.

Specific organs, such as the liver and brain, were also evaluated (FIGS. 16-21). While the liver had a different fat profile than previous tissues studied (FIG. 16), 90 day dosage studies with D2-LA/D4-ALA demonstrated that tissues became highly enriched in deuterium, with about 40% of the total fat being deuterated (FIG. 17). Moreover, the liver study indicated that fat distribution remained relatively unchanged by the tested dosage (FIG. 16-17). Additionally, 90 day dosage studies with D2-LA only illustrated a similar fat profile as previous studies, along with about 32% total fat being deuterated (FIG. 18). Consequently, fat profiles and deuteration profiles in the liver were maintained regardless of the administered deuterated component. Like the liver, the brain also had a different fat profile than previous tissues studied (FIGS. 19-21). 90 day dosage studies with D2-LA/D4-ALA demonstrated that tissues became highly enriched in deuterium, with about 30% of the total fat being deuterated (FIG. 19). Moreover, the brain study indicated that fat distribution remained relatively unchanged by the tested dosage (FIGS. 19-21). Additionally, 90 day dosage studies with D2-LA/ALA illustrated a similar fat profile as previous studies, along with about 23% total fat being deuterated (FIG. 20). Consequently, fat profiles and deuteration profiles in the brain were maintained regardless of the administered deuterated component.

Example 20

Testing for Efficacy Against Impaired Energy Processing Disorders and Mitochondrial Deficiencies Several readily measurable clinical markers are useful for assessing the metabolic state of patients with mitochondrial disorders. These markers can also be used as indicators of the efficacy of a given therapy, as the level of a marker is moved from the pathological value to the healthy value. These clinical markers include, but are not limited to, one or more energy biomarkers such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH(NADH+H+) or NADPH(NADPH+H+) levels; NAD or NADP levels; ATP levels; anaerobic threshold; reduced coenzyme Q (CoQred) levels; oxidized coenzyme Q (CoQox) levels; total coenzyme Q (CoQtot) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers can be routinely measured in exercise physiology laboratories, and provide convenient assessments of the metabolic state of a subject.

Several metabolic biomarkers have already been used to evaluate efficacy of Coenzyme Q10, and these metabolic biomarkers can be monitored as energy biomarkers for use in the methods disclosed herein. Pyruvate, a product of the anaerobic metabolism of glucose, is removed by reduction to lactic acid in an anaerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (See Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7):695-7 (1994)) is, therefore, widely used as a noninvasive test for detection of mitochondrial cytopathies (See Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)) and toxic mitochondrial myopathies (Chariot et al., Arthritis Rheum. 37(4):583-6 (1994)). Changes in the redox state of liver mitochondria can be investigated by measuring the arterial ketone body ratio (acetoacetate/3-hydroxybutyrate: AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2):287-91 (1997); Honda et al., Leuk. Res. 24(6):461-8 (2000); Pilger et al., Free Radic. Res. 35(3):273-80 (2001); Kim et al. Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., Neurology 62(8):1297-302 (2004)). Phosphorous MRS (31P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242(7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-VO2 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Lactic acid (lactate) levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of NADH+H+, NADPH+H+, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, including, but not limited to, the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, NADH(NADH+H+) or NADPH(NADPH+H+) can be measured by a variety of fluorescent, enzymatic, or electrochemical techniques, e.g., the electrochemical assay described in US 2005/0067303, which is incorporated herein by reference.

Oxygen consumption (vO2 or VO2), carbon dioxide output (vCO2 or VCO2), and respiratory quotient (VCO2/VO2): vO2 is usually measured either while resting (resting vO2) or at maximal exercise intensity (vO2 max). Optimally, both values will be measured. However, for severely disabled patients, measurement of vO2 max may be impractical. Measurement of both forms of vO2 is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, reduced Cytochrome C, and ratio of oxidized Cytochrome C to reduced Cytochrome C: Cytochrome C parameters, such as oxidized cytochrome C levels (Cyt Cox), reduced cytochrome C levels (Cyt Cred), and the ratio of oxidized cytochrome C/reduced cytochrome C ratio (Cyt Cox)/(Cyt Cred), can be measured by in vivo near infrared spectroscopy. See, e.g., Rolfe, P., "In vivo near-infrared spectroscopy," Ann. Rev. Biomed. Eng. 2:715-54 (2000) and Strangman et al., "Non-invasive neuroimaging using near-infrared light" Biol. Psychiatry 52:679-93 (2002).

Exercise tolerance/Exercise intolerance: Exercise intolerance is defined as "the reduced ability to perform activities that involve dynamic movement of large skeletal muscles because of symptoms of dyspnea or fatigue" (Piñ a et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q (CoQred) levels, oxidized coenzyme Q (CoQox) levels, total coenzyme Q (CoQtot) levels, oxidized cytochrome C levels, reduced cytochrome C levels, oxidized cytochrome C/reduced cytochrome C ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to evaluate efficacy of the compounds and methods of the invention.

Any one or any combination of the energy biomarkers described herein provide conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

For example, subjects are screened either by genetic testing or by questionnaire for Co-enzyme Q deficiency; Complex I-V Deficiency, Diabetes mellitus and deafness (DAD), and Maternally Inherited Diabetes and Deafness (MIDD); Friedreich's ataxia (FA); Leber's congenital amaurosis; Leber's hereditary optic neuropathy (LHON); Leigh syndrome; Mitochondrial myopathy, encephalopathy, lactic acidosis, and stroke (MELAS) syndrome; Mitochondrial neurogastrointestinal encephalomyopathy (MNGIE); Myoclonus Epilepsy Associated with Ragged-Red Fibers (MERRF) syndrome; Myoneurogenetic gastrointestinal encephalopathy (MNGIE) and neuropathy; Neuropathy, ataxia, retinitis pigmentosa, and ptosis (NARP); optic neuropathies and opthalmoplegias; Wolff-Parkinson-White syndrome and other cardiomyopathies; X-linked Adrenoleukodystrophy (X-ALD), as well as diseases of musculoskeletal system (lipid myopathies, chronic fatigue, fibromyalgia syndrome); kidney (Fanconi's syndrome and glomerulonephropathies); blood (Pearson's syndrome), and brain (migraines, seizures, and strokes). Subjects testing positive for one or more genetic defects (or with a maternal relative carrying such defects) and/or diagnosed with one of the described conditions are tested for the level of one or more energy biomarkers such as lactic acid (lactate) levels; pyruvic acid (pyruvate) levels; lactate/pyruvate ratios; phosphocreatine levels; NADH(NADH+H+) levels; NADPH (NADPH+H+) levels; NAD levels; NADP levels; ATP levels; reduced coenzyme Q (CoQ red) levels; oxidized coenzyme Q (CoQ ox) levels; total coenzyme Q (CoQ tot) levels; oxidized cytochrome C levels; reduced cytochrome C levels; oxidized cytochrome C/reduced cytochrome C ratio; acetoacetate levels; β-hydroxy butyrate levels; acetoacetate/β-hydroxy butyrate ratio, 8-hydroxy-2'-deoxyguanosine (8-OHdG) levels; levels of reactive oxygen species; levels of oxygen consumption (VO2); or levels of carbon dioxide output (VCO2). Additionally, subjects are tested for energy biomarkers by the following measures: respiratory quotient (VCO2/VO2); exercise tolerance; or anaerobic threshold. Subjects testing positive for a genetic defect (or with a maternal relative carrying such defect), but negative for an abnormal energy biomarker (or level thereof), are treated with D-PUFA (0.01, 0.1, 1.0, 10.0, and 100 mg/kg of D2-LA, D4-ALA, and 1:1 combinations of both D2-LA and D4-ALA) daily over a six month period. Subjects testing positive for one or more genetic defects (or with a maternal relative carrying such defects) and positive for an abnormal level of energy biomarker are treated with D-PUFA (0.01, 0.1, 1.0, 10.0, and 100 mg/kg of D2-LA, D4-ALA, and 1:1 combinations of both D2-LA and D4-ALA) daily over a six month period. One or more of the above described energy biomarkers are monitored weekly. D2-LA and D4-ALA are expected to improve the subject's energy biomarker levels. Similarly, Compounds disclosed herein are also screened in cells from CoQ10 deficient patients and the results of the screening are used to determine a compound's efficacy. For example, an initial screen is performed using D-PUFA (0.01, 0.1, 1.0, 10.0, and 100 μM of D2-LA, D4-ALA, and 1:1 combinations of both D2-LA and D4-ALA) administered daily over a six month period to identify effectiveness for ameliorating redox disorders. Test compounds, one or more reference compounds (e.g. Idebenone, decylubiquinone, Trolox and α-tocopherol acetate), and appropriate controls H-PUFA (0.01, 0.1, 1.0, 10.0, and 100 μM of LA, ALA, and 1:1 combinations of both LA and ALA) are tested for the ability to rescue FRDA fibroblasts stressed by the addition of L-buthionine-(S,R)-sulfoximine (BSO), as a modification of the procedure described in Jauslin et al., *Hum. Mol. Genet.* 11(24):3055 (2002), Jauslin et al., *FASEB J.* 17:1972-4 (2003), and International Patent Application WO 2004/003565, which are incorporated herein by reference. Cells from CoQ10 deficient patients are expected to be hypersensitive to inhibition of the de novo synthesis of glutathione (GSH) with L-buthionine-(S,R)-sulfoximine (BSO), a specific inhibitor of GSH synthetase (Jauslin et al., *Hum. Mol. Genet.* 11(24):3055 (2002)). This specific BSO-mediated cell death is expected to be prevented by administration of antioxidants or molecules involved in the antioxidant pathway, such as α-tocopherol, selenium, or small molecule glutathione peroxidase mimetics. However, antioxidants will likely differ in their potency, i.e. the concentration at which they are able to rescue BSO-stressed cells from CoQ10 patients. D2-LA and D4-ALA are expected to rescue BSO-stressed cells from CoQ10 patients to a greater degree than LA or ALA. Similarly, compounds can be screened against human fibroblasts from LHON Patients and FA patients as described above. D2-LA and D4-ALA are expected to afford similar results to the previously described method.

To further determine a compound's efficacy, the following methodology can be used: cell lines derived from X-ALD patients and X-ALD mice are grown in MEM (fibroblasts) or RPMI (lymphoblastoid cells) supplemented with fetal calf serum (10%), penicillin (100 U/ml), streptomycin (100 U/ml) and glutamine (2 mM). On day 0, cells are divided into separate tissue culture flasks, and D-PUFA (0.01, 0.1, 1.0, 10.0, and 100 μM of D2-LA, D4-ALA, and 1:1 combinations of both D2-LA and D4-ALA) or H-PUFA (0.01, 0.1, 1.0, 10.0, and 100 μM of LA, ALA, and 1:1 combinations of both LA and ALA) are added. After 24, 48, and 72 hours, cells are harvested, washed twice with sterile water and then subjected to alkaline methanolysis and saponification, and lipid extraction as described (Moss C W, Lambert M A, Merwin W H. *Appl. Microbial.* 1974; 1, 80-85; (Shaw, 1953 Shaw, W. H. C.; Jefferies, J. P. Determination of ergosterol in yeast. *Anal Chem* 25:1130; 1953). Total lipids are extracted, converted to methyl esters, purified by TLC and subjected to capillary GC analysis. Following similar procedures, C24:0 β-oxidation activity of human and mouse fibroblasts and human lymphoblastoid cells are determined by measuring their capacity to degrade [1-$^{14}$C]-C24:0 fatty acid to water-soluble products. Phytanic acid oxidation is also measured after incubating cells with [2,3-$^3$H]-phytanic acid for 24 hours and monitoring the release of $^3$H—H$_2$O into the aqueous medium. See U.S. Pat. No. 6,355,677, which is incorporated herein by reference. D2-LA and D4-ALA are expected to reduce the amount of oxidized fatty acids that are detected in these assays.

Example 21

Model for Testing Incorporation into Cells

Isotope ratio Mass-spectrometry can be used to confirm incorporation of D-PUFA into the phospholipid membranes of various tissues. When delivering D2-LA and D4-ALA through dietary supplementation, incorporation into animal tissues can be monitored using an isotope ratio mass-spectrometry technique that will allow for measurement of the total increase in deuterium composition in lipid membranes, thus reporting on incorporation of D2-LA, D4-ALA, and any other PUFA derived from these compounds. Using this method, a substantial uptake of D-PUFA into animal tissue can be detected. For example, mice are supplemented with D-PUFA (0.01, 0.1, 1.0, 10.0, and 100 mg/kg of D2-LA, D4-ALA, and 1:1 combinations of both D2-LA and D4-ALA) or H-PUFA (0.01, 0.1, 1.0, 10.0, and 100 mg/kg of LA, ALA, and 1:1 combinations of both LA and ALA) as the only PUFA source for 6 days, exposed acutely to a known oxidant or saline vehicle and continued on the same diet for an additional 6 days. Brain, liver, heart, and lung tissue are removed, and homogenate samples from control mice and test compound-treated mice are analyzed for deuterium content as described for Example 7 above. D2-LA and D4-ALA are expected to be found in the tissues and cells analyzed.

Example 22

Testing for Efficacy Against Autism and Related Disorders

D-PUFA (0.01, 0.1, 1.0, 10.0, and 100 mg/kg of D2-LA, D4-ALA, and 1:1 combinations of both D2-LA and D4-ALA) or H-PUFA (0.01, 0.1, 1.0, 10.0, and 100 mg/kg of LA, ALA, and 1:1 combinations of both LA and ALA) are screened for their ability to rescue Autistic Syndrome Disorder (ASD) fibroblasts stressed by addition stressed by the addition of L-buthionine-(S,R)-sulfoximine (BSO), as described in Jauslin et al., Hum. Mol. Genet. 11(24):3055 (2002), Jauslin et al., FASEB J. 17:1972-4 (2003), and International Patent Application WO 2004/003565, which are incorporated herein by reference. ASD fibroblasts are likely to be hypersensitive to inhibition of the de novo synthesis of glutathione (GSH) with L-buthionine-(S,R)-sulfoximine (BSO), a specific inhibitor of GSH synthetase (Jauslin et al., Hum. Mol. Genet. 11(24):3055 (2002)). BSO-mediated cell death should be prevented and/or lessened by the administration of D-PUFAs.

Example 23

Testing for Efficacy Against Schizophrenia or Bipolar Disorder

Patients with schizophrenia and free of antipsychotic medication are selected for the study. Controlling for dietary PUFA sources, D-PUFA (0.01, 0.1, 1.0, 10.0, and 100 mg/kg of D2-LA, D4-ALA, and 1:1 combinations of both D2-LA and D4-ALA) or H-PUFA (0.01, 0.1, 1.0, 10.0, and 100 mg/kg of LA, ALA, and 1:1 combinations of both LA and ALA) are administered daily over a six month period. Each week, patients are evaluated for frequency and duration of schizophrenic episodes. Additionally, blood samples are taken each week and biomarkers of oxidative stress, such as the biomarkers described above, are measured. D2-LA and D4-ALA are expected to reduce the frequency and/or duration of schizophrenic episodes and reduce the levels of biomarkers associated with oxidative stress.

A similar study can be performed with patients suffering from Bipolar Disorder. D2-LA and D4-ALA are expected to reduce the frequency and/or duration of mood changes such as depression and mania and reduce the levels of biomarkers associated with oxidative stress.

A similar study can be performed with patients suffering from Huntington's disease. D2-LA and D4-ALA are expected to reduce neuronal cell death and the levels of biomarkers associated with oxidative stress.

Example 24

Testing for Efficacy in a Down's Syndrome Model

Down's Syndrome cortical neuron cultures are known in the art. D-PUFA (0.01, 0.1, 1.0, 10.0, and 100 µM of D2-LA, D4-ALA, and 1:1 combinations of both D2-LA and D4-ALA) or H-PUFA (0.01, 0.1, 1.0, 10.0, and 100 µM of LA, ALA, and 1:1 combinations of both LA and ALA) are administered to DS cortical cultures and cell-viability is measured at 24, 48, and 72 hours using known methods. D2-LA and D4-ALA are expected to enhance the survival of DS cortical neurons.

Example 25

Figure 22:
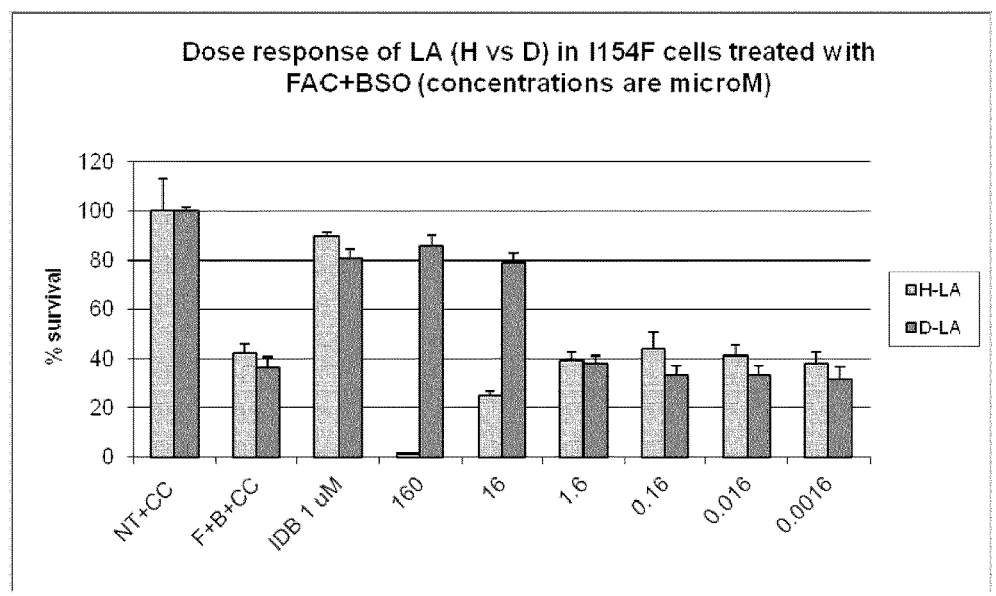
FIG. 22. Dose response of LA (H v. D) in m-fibroblasts having a mutated form of human frataxin (I154F).

Testing for Efficacy in a Friedreich's Ataxia Model m-Fibroblasts (Frda$^{L3/L-;\ h-I54F}$) have both frataxin alleles deleted and over-express a mutated form of human frataxin (I154F) that is associated with the disease. Treatment of cells with FAC (iron ammonium citrate) and BSO (Buthionine sulphoximine—an inhibitor of glutathione synthesis) resulted in loss of cell viability. Cells were plated in 48 well-plates and treated with FAC and BSO for 48 h and 24 h respectively. H/D-PUFA were added 2 hours after BSO treatment. At the end of the experiment, cell viability was assessed by the Promega Cell-Glow kit and measured in Arbitrary Luminescence Units (ALU) also expressed as % survival (FIG. 22). In FIG. 22, NT stands for not treated; F stands for iron ammonium citrate; B stands for buthionine sulphoximine; CC stands for carrier control DMSO (dimethylsulfoxide) used to bring the final concentration in the assay to 0.5%; and IDB stands for idebenone. The results indicated a dose-dependent rescue of viability by administering D-LA. Similar results (not shown) were also obtained using D-ALA with the experimental protocol described above.

Figure 23:
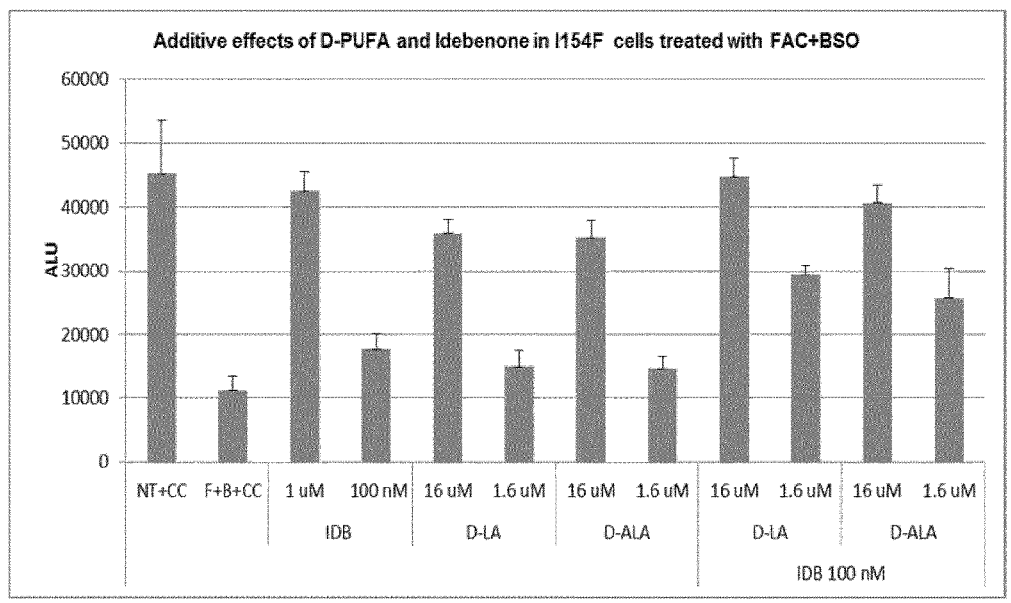
FIG. 23. Dose response of D-PUFA, Idebenone, and combinations thereof in m-fibroblasts having a mutated form of human frataxin (I154F).

Likewise, an investigation was undertaken to measure the effects of co-administering idebenone with D-PUFAs (FIG. 23). Using the above-described experimental protocol, the results indicated that co-administering idebenone with either D-LA or D-ALA resulted in increased cell survival as compared with individual administration of idebenone, D-LA, or D-ALA.

Figure 24:
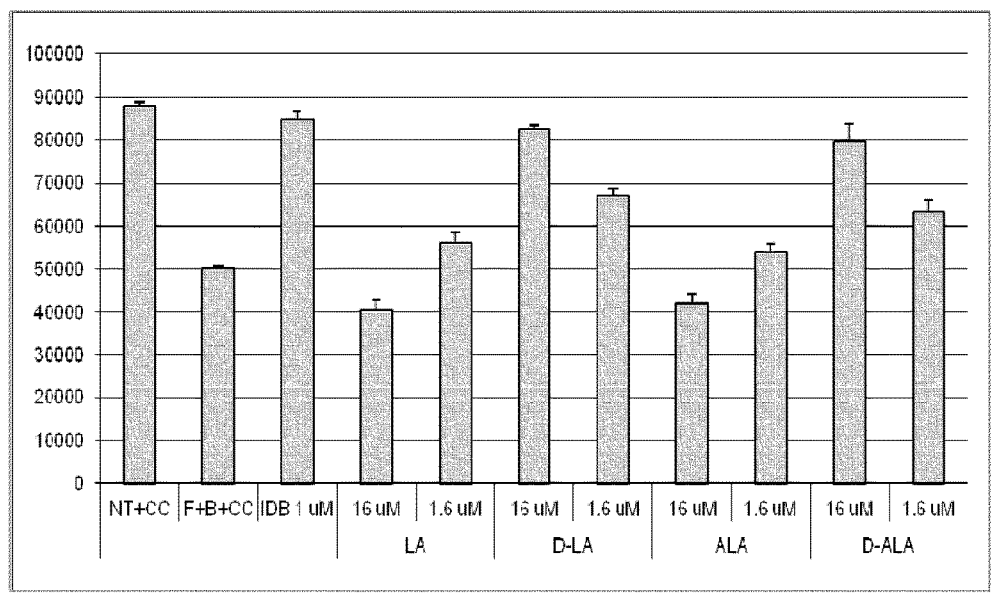
FIG. 24. D-PUFA pre-treatment dose response for m-fibroblasts having a mutated form of human frataxin (I154F).

To determine the effect of pre-treatment upon D-PUFA activity, a similar experimental protocol was used in which cells were treated with FAC and H/D-PUFAs for 48 hours, followed by BSO addition 24 hours later with cell viability measured another 24 hours later (FIG. 24). The results indicated a dose-dependent effect on cell survival by pre-treating cells with D-PUFAs.

Additional experiments were also performed to study the effects of co-administering different D-PUFAs (data not shown). I154F cells were treated with either 100% D-LA, 75% D-LA/25% D-ALA, 50% D-LA/50% D-ALA, and 100% D-ALA. The results indicated that co-administering mixing amounts of different D-PUFAs does not affect relative cell survival.

CONCLUSION

While the invention has been described with reference to the specific embodiments thereof, it should be understood by those skilled in the art that various changes may be made and equivalents may be substituted without departing from the true spirit and scope of the invention. This includes embodiments which do not provide all of the benefits and features set forth herein. In addition, many modifications may be made to adapt a particular situation, material, composition of matter, process, process step or steps, to the objective, spirit and scope of the present invention. All such modifications are intended to be within the scope of the claims appended hereto. Accordingly, the scope of the invention is defined only by reference to the appended claims.

What is claimed is:

1. A method of treating or inhibiting progression of an impaired energy processing disorder or mitochondrial deficiency, comprising:

treating a patient having an impaired energy processing disorder or mitochondrial deficiency over a time period by repeatedly administering an effective amount of a polyunsaturated fatty acid or fatty acid ester during a treatment period, wherein the polyunsaturated fatty acid or fatty acid ester is deuterated at one or more bis-allylic positions, wherein the amount of deuterated polyunsaturated fatty acid or fatty acid ester administered to or ingested by the patient is in the range of about 5% to about 75% of the total amount of polyunsaturated fatty acid or fatty acid ester administered to or ingested by the patient, such that over the treatment period the body of the patient incorporates significant amounts of deuterated polyunsaturated fatty acid or fatty acid ester and undeuterated polyunsaturated fatty acid or fatty acid ester, wherein the amount of deuterated polyunsaturated fatty acid or fatty acid ester in the patient's body is sufficient to reduce or prevent autoxidation and cancel toxicity of undeuterated polyunsaturated fatty acid or fatty acid ester in the patient's body.

2. The method of claim 1, wherein the stabilization comprises at least one deuterium atom at a bis-allylic position, wherein the at least one deuterium atom is present at a level greater than 0.02%.

3. The method of claim 2, wherein over the treatment period the stabilized fatty acid or fatty acid ester comprise between about 10% and about 50% of the total amount of fatty acids or fatty acid esters in the patient's body.

4. The method of claim 2, wherein over the treatment period the stabilized fatty acid or fatty acid ester comprise between about 10% and about 30% of the total amount of fatty acids or fatty acid esters in the patient's body.

5. The method of claim 2, wherein over the treatment period the isotopically stabilized fatty acid or fatty acid ester comprise about 20% to about 50% of the total amount of fatty acids or fatty acid esters in the patient's body.

6. The method of claim 2, wherein a cell or tissue of the patient maintains a sufficient concentration of the fatty acid or fatty acid ester to prevent autooxidation of the naturally occurring polyunsaturated fatty acid or fatty acid ester.

7. The method of claim 2, wherein the deuterated polyunsaturated fatty acid or fatty acid ester is an omega-3 fatty acid or fatty acid ester, or an omega-6 fatty acid or fatty acid ester.

8. The method of claim 7, wherein the deuterated polyunsaturated fatty acid or fatty acid ester is selected from the group consisting of 11,11-D2-linolenic acid, 14,14-D2-linolenic acid, 11,11,14,14-D4-linolenic acid, 11,11-D2-linoleic acid, 11-D-linolenic acid, 14-D-linolenic acid; 11,14-D2-linolenic acid, and 11-D-linoleic acid.

9. The method of claim 7, wherein the deuterated polyunsaturated fatty acid or fatty acid ester is further deuterated at at least one saturated methylene group that is adjacent to a second saturated methylene group.

10. The method of claim 1, wherein the deuterated polyunsaturated fatty acid ester is a triglyceride, diglyceride, or monoglyceride.

11. The method of claim 1 further comprising co-administering an antioxidant.

12. The method of claim 11, wherein the antioxidant is idebenone, mitoquinone, mitoquinol, vitamin C, or vitamin E.

13. The method of claim 1, wherein the deuterated polyunsaturated fatty acid or fatty acid ester is administered orally.

14. The method of claim 1, wherein the deuterated polyunsaturated fatty acid or fatty acid ester is arachidonic acid or an ester thereof.

15. The method of claim 1, wherein the deuterated fatty acid or fatty acid ester is eicosapentaenoic acid or an ester thereof.

16. The method of claim 1, wherein the deuterated fatty acid or fatty acid ester is docosahexaenoic acid or an ester thereof.

17. The method of claim 1, wherein the deuterated fatty acid or fatty acid ester is a linoleic acid or an ester thereof.

18. The method of claim 1, wherein the deuterated fatty acid or fatty acid ester is a linolenic acid or an ester thereof.

19. The method of claim 1, wherein the deuterated fatty acid or fatty acid ester is an ethyl ester.

20. The method of claim 1, wherein the amount of deuterated polyunsaturated fatty acid or fatty acid ester administered to or ingested by the patient is in the range of about 0.1 mg/kg to about 100 mg/kg per day.

21. The method of claim 1, wherein the deuterated polyunsaturated fatty acid or fatty acid ester is 11,11-D2-linoleic acid or ethyl ester thereof.

22. The method of claim 1, wherein the deuterated polyunsaturated fatty acid or fatty acid ester is 11,11,14,14-D4-linolenic acid or ethyl ester thereof.

* * * * *

UNITED STATES PATENT AND TRADEMARK OFFICE
CERTIFICATE OF CORRECTION

| | |
|---|---|
| PATENT NO. | : 10,058,612 B2 |
| APPLICATION NO. | : 14/113546 |
| DATED | : August 28, 2018 |
| INVENTOR(S) | : Mikhail S. Shchepinov |

It is certified that error appears in the above-identified patent and that said Letters Patent is hereby corrected as shown below:

On the Title Page

Item (56) Column 2 at Line 48, Under Other Publications, after "Research," insert --2005,--.

In the Drawings

Sheet 22 of 25 (FIG. 21) at Line 1 (Y-axis), Change "Fat)" to --Fat--.

In the Specification

In Column 2 at Line 49, Change "cyclogenases" to --cyclogenesis--.

In Column 3 at Line 39, Change "autooxidation" to --autoxidation--.

In Column 3 at Line 50, Change "II-D-" to --11-D- --.

In Column 3 at Line 51, Change "II-D-" to --11-D- --.

In Column 6 at Line 31, Change "neuro gastrointestinal" to --neurogastrointestinal--.

In Column 7 at Line 19, Change "opthalmoplegias;" to --ophthalmoplegias;--.

In Column 9 at Line 5, Change "Aspectes" to --Aspects--.

In Column 9 at Line 39, Change "Biocehmica" to --Biochimica--.

In Column 15 at Line 48 (Approx.), Change "Acids Include:" to --acids include:--.

In Column 20 at Line 12 (Approx.), Change "Cl.," to --Cl,--.

Signed and Sealed this
Eleventh Day of December, 2018

Andrei Iancu
*Director of the United States Patent and Trademark Office*

CERTIFICATE OF CORRECTION (continued)
U.S. Pat. No. 10,058,612 B2

In Column 22 at Line 50, Change "sulfinylamindes," to --sulfinylamides,--.

In Column 23 at Line 27, Change "parafin;" to --paraffin;--.

In Column 23 at Line 31, Change "soribitan" to --sorbitan--.

In Column 24 at Line 50, Change "berylium," to --beryllium,--.

In Column 25 at Line 49-50, Change "autooxidation." to --autoxidation.--.

In Column 25 at Line 56 (Approx.), Change "autooxidation" to --autoxidation--.

In Column 25 at Line 57 (Approx.), Change "autooxidation" to --autoxidation--.

In Column 26 at Line 2, Change "berylium," to --beryllium,--.

In Column 29 at Line 24 (Approx.), Change "haloakyl," to --haloalkyl,--.

In Column 30 at Line 40, Change "-tetramethy 1-" to -- -tetramethyl- --.

In Column 33 at Line 57, Change "cocao" to --cocoa--.

In Column 34 at Line 52, Change "FINE," to --HNE,--.

In Column 37 at Line 19, Change "CH$_3$)," to --CH$_3$).--.

In Column 37 at Line 41, Change "OCH$_3$),2.3" to --OCH$_3$), 2.3--.

In Column 37 at Line 41, Change "CH$_2$),2.14(t," to --CH$_2$), 2.14 (t,--.

In Column 40 at Line 38, Change "δ):2.16(q," to --δ): 2.16 (q,--.

In Column 40 at Line 41, After "12.2" insert --.--.

In Column 48 at Line 22, Change "(508)." to --(508)--.

In Column 49 at Line 14 (Approx.), Change "II-D-" to --11-D- --.

In Column 55 at Line 49, Change "Aspects." to --Aspects--.

In Column 55 at Line 58, Change "Aspects." to --Aspects--.

In Column 56 at Line 4, Change "Aspects." to --Aspects--.

In Column 57 at Line 53, Change "qualititatively" to --qualitatively--.

CERTIFICATE OF CORRECTION (continued)
U.S. Pat. No. 10,058,612 B2

In Column 64 at Line 27, Change "(Piñ a" to --(Piña--.

In Column 65 at Line 14, Change "opthalmoplegias;" to --ophthalmoplegias;--.

In Column 65-66 at Line 54-67 (Column 65) 1-22 (Column 66), Delete "Compounds disclosed herein are also screened in cells from CoQ10 deficient patients and the results of the screening are used to determine a compound's efficacy. For example, an initial screen is performed using D-PUFA (0.01, 0.1, 1.0, 10.0, and 100 μM of D2-LA, D4-ALA, and 1:1 combinations of both D2-LA and D4-ALA) administered daily over a six month period to identify effectiveness for ameliorating redox disorders. Test compounds, one or more reference compounds (e.g. Idebenone, decylubiquinone, Trolox and α-tocopherol acetate), and appropriate controls H-PUFA (0.01, 0.1, 1.0, 10.0, and 100 μM of LA, ALA, and 1:1 combinations of both LA and ALA) are tested for the ability to rescue FRDA fibroblasts stressed by the addition of L-buthionine-(S,R)-sulfoximine (BSO), as a modification of the procedure described in Jauslin et al., *Hum. Mol. Genet.* 11(24):3055 (2002), Jauslin et al., *FASEB J.* 17:1972-4 (2003), and International Patent Application WO 2004/003565, which are incorporated herein by reference. Cells from CoQ10 deficient patients are expected to be hypersensitive to inhibition of the de novo synthesis of glutathione (GSH) with L-buthionine-(S,R)-sulfoximine (BSO), a specific inhibitor of GSH synthetase (Jauslin et al., *Hum. Mol. Genet.* 11(24):3055 (2002)). This specific BSO-mediated cell death is expected to be prevented by administration of antioxidants or molecules involved in the antioxidant pathway, such as α-tocopherol, selenium, or small molecule glutathione peroxidase mimetics. However, antioxidants will likely differ in their potency, i.e. the concentration at which they are able to rescue BSO-stressed cells from CoQ10 patients. D2-LA and D4-ALA are expected to rescue BSO-stressed cells from CoQ10 patients to a greater degree than LA or ALA. Similarly, compounds can be screened against human fibroblasts from LHON Patients and FA patients as described above. D2-LA and D4-ALA are expected to afford similar results to the previously described method." and insert the same on Column 65, Line 53, as a continuation of the same paragraph.

In Column 66 at Line 37, Change "Microbial." to --Microbiol.--.

In the Claims

In Column 70 at Line 10 (Approx.), In Claim 8, change "acid;" to --acid,--.